United States Patent
Yang et al.

(10) Patent No.: US 12,377,103 B2
(45) Date of Patent: Aug. 5, 2025

(54) USE OF BROMODOMAIN-CONTAINING PROTEIN 9 INHIBITORS TO TREAT AND/OR PREVENT UTERINE LEIOMYOSARCOMA

(71) Applicant: The University of Chicago, Chicago, IL (US)

(72) Inventors: Qiwei Yang, Bolingbroke, IL (US); Ayman Al-Hendy, Hinsdale, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 18/345,461

(22) Filed: Jun. 30, 2023

(65) Prior Publication Data

US 2024/0000787 A1    Jan. 4, 2024

Related U.S. Application Data

(60) Provisional application No. 63/357,886, filed on Jul. 1, 2022.

(51) Int. Cl.
*A61K 31/519* (2006.01)

(52) U.S. Cl.
CPC .................. *A61K 31/519* (2013.01)

(58) Field of Classification Search
CPC .................................................. A61K 31/519
See application file for complete search history.

(56) References Cited

U.S. PATENT DOCUMENTS

2021/0230190 A1*  7/2021  Ruppel ............... A61K 47/545

OTHER PUBLICATIONS

Sima X, He J, Peng J, Xu Y, Zhang F, Deng L (2019) The genetic alteration spectrum of the SWI/SNF complex: The oncogenic roles of BRD9 and ACTL6A. PLoS ONE 14(9): e0222305. https://doi.org/10.1371/journal.pone.0222305 (Year: 2019).*
Caroline Hana and Gina Z. D'Amato, Uterine sarcomas, insight into its risk factors: A systematic review—abstract—Journal of Clinical Oncology, vol. 38, No. 15_suppl, May 25, 2020 (Year: 2020).*
Felix AS, et al., The etiology of uterine sarcomas: a pooled analysis of the epidemiology of endometrial cancer consortium. Br J Cancer. Feb. 19, 2013;108(3):727-34. doi: 10.1038/bjc.2013.2. Epub Jan. 24, 2013. PMID: 23348519; PMCID: PMC3593566 (Year: 2013).*
The Oxford English Dictionary—prevent definition (printed Feb. 1, 2024) (Year: 2024).*
Shi at al., PNAS, Published online Jul. 18, 2016, https://www.pnas.org/doi/epdf/10.1073/pnas.1608319113 (Year: 2016).*
Supporting Information Shi et al. 10.1073/pnas.1608319113 (Year: 2016).*

(Continued)

*Primary Examiner* — Clinton A Brooks
*Assistant Examiner* — Zabela Schmidt
(74) *Attorney, Agent, or Firm* — Leydig, Voit & Mayer, Ltd.

(57) ABSTRACT

In aspects, the present disclosure provides a method of treating or preventing a uterine leiomyosarcoma in a female mammal, the method comprising, consisting essentially of, or consisting of administering to the female mammal an effective amount of an inhibitor of bromodomain-containing protein 9 (BRD9).

12 Claims, 27 Drawing Sheets

Specification includes a Sequence Listing.

(56) References Cited

OTHER PUBLICATIONS

Karim et al., J. Med. Chem. 2020, 63, 3227-3237 (Year: 2020) (Year: 2020).*
Sima X, He J, Peng J, Xu Y, Zhang F, Deng L (2019) The genetic alteration spectrum of the SWI/SNF complex: The oncogenic roles of BRD9 and ACTL6A. PLoS ONE 14(9): e0222305. https://doi.org/10.1371/journal.pone.0222305 (Year: 2019) (Year: 2019).*
Caroline Hana and Gina Z. D'Amato, Uterine sarcomas, insight into its risk factors: A systematic review—abstract—Journal of Clinical Oncology, vol. 38, No. 15_suppl, May 25, 2020 (Year: 2020) (Year: 2020).*
Felix AS, et al., The etiology of uterine sarcomas: a pooled analysis of the epidemiology of endometrial cancer consortium. Br J Cancer. Feb. 19, 2013;108(3):727-34. doi: 10.1038/bjc.2013.2. Epub Jan. 24, 2013. PMID: 23348519; PMCID: PMC3593566 (Year: 2013) (Year: 2013).*
Jungmin Choi, et. al., Integrated mutational landscape analysis of uterine leiomyosarcomas, Proceedings of the National Academy of Sciences vol. 118, Issue Apr. 15, 2021 (Year: 2021) (Year: 2021).*
The Oxford English Dictionary—prevent definition (printed Feb. 1, 2024) (Year: 2024) (Year: 2024).*
Shi at al., PNAS, Published online Jul. 18, 2016, https://www.pnas.org/doi/epdf/10.1073/pnas.1608319113 (Year: 2016) (Year: 2016).*
Supporting Information Shi et al. 10.1073/pnas.1608319113 (Year: 2016) (Year: 2016).*
Gülnur Yorulmaz et. al., Wien Klin Wochenschr (2007) 119/17-18: 557-560 (Year: 2007).*
Andrew R. Reynolds et. al., Cancer Discov (2023) 13 (5): 1058-1083 (Year: 2023).*
Suzanne George et al., Soft Tissue and Uterine Leiomyosarcoma. JCO 36, 144-150(2018). DOI:10.1200/JCO.2017.75.9845 (Year: 2018).*
Jungmin Choi, et. al., Integrated mutational landscape analysis of uterine leiomyosarcomas, Proceedings of the National Academy of Sciences vol. 118, Issue Apr. 15, 2021 (Year: 2021).*
Karim et al., J. Med. Chem. 2020, 63, 3227-3237 (Year: 2020).*
Bertsch et al., Modern Pathology, 27:1144-1153 (2014), made of record on the IDS (Year: 2014).*
Aicher et al., "Serum response elements activate and cAMP responsive elements inhibit expression of transcription factor Egr-1 in synovial fibroblasts of rheumatoid arthritis patients," International Immunology, 11(1): 47-61 (Sep. 1998) Published online Jan. 1, 1999.
Ali et al., "Activation of β-Catenin Signaling and its Crosstalk With Estrogen and Histone Deacetylases in Human Uterine Fibroids," J Clin Endocrinol Metab,, 105(4): e1517-e1535 (Apr. 2020). Published online Dec. 25, 2019.
Archer et al., "Proteomics, Post-translational Modifications, and Integrative Analyses Reveal Molecular Heterogeneity within Medulloblastoma Subgroups," Cancer Cell, 34: 396-410 (Sep. 2018).
Belkina et al., "BET Protein Function Is Required for Inflammation: Brd2 Genetic Disruption and BET Inhibitor JQ1 Impair Mouse Macrophage Inflammatory Responses," J Immunol., 190(7): 3670-3678 (Apr. 2013).
Bell et al., "PIK3CA Cooperates with KRAS to Promote MYC Activity and Tumorigenesis via the Bromodomain Protein BRD9," Cancers, 11(11): 1634, 20 pages (Oct. 2019).
Bertsch et al., "MED12 and HMGA2 mutations: two independent genetic events in uterine leiomyoma and leiomyosarcoma," Modern Pathology, 27:1144-1153 (2014)). Published online Jan. 3, 2014.
Bhargava et al., "IGF2 mRNA binding protein 3 (IMP3) mediated regulation of transcriptome and translatome in glioma cells," Cancer Biology & Therapy, 19(1): 42-52 (Jan. 2018). Published online Dec. 19, 2017.
Bulavin et al., "Loss of Oncogenic H-ras-Induced Cell Cycle Arrest and p38 Mitogen-Activated Protein Kinase Activation by Disruption of Gadd45a," Molecular and Cellular Biology, 23(11): 3859-3871 (Jun. 2003). Published online Mar. 27, 2023.

Bulun et al., "Uterine Fibroids," N. Engl. J. Med., 369: 1344-1355 (Oct. 2013).
Carbajo-Garcia, et al., "Integrative analysis of the DNA methylome and transcriptome in uterine leiomyoma shows altered regulation of genes involved in metabolism, proliferation, extracellular matrix, and vesicles," Journal of Pathology, 257: 663-673 (Aug. 2022). Published online Jun. 13, 2022.
Care et al., "Parsimonious Gene Correlation Network Analysis (PGCNA): a tool to define modular gene co-expression for refined molecular stratification in cancer," Systems Biology and Applications, 5(13): 1-17 (Apr. 2019).
Chen et al., "Topoisomerase IIα in Chromosome Instability and Personalized Cancer Therapy," Oncogene, 34(31): 4019-4031 (Jul. 2015).
Chinenov et al., "Fos-Jun interactions that mediate transcription regulatory specificity," Oncogene, 20(19): 2438-2452. (Apr. 2001).
Choi et al., "Integrated mutational landscape analysis of uterine leiomyosarcomas," PNAS, 118(15): e2025182118, Supplemental Data 14, 2 pages (Apr. 2021).
Choi et al., "Integrated mutational landscape analysis of uterine leiomyosarcomas," PNAS, 118(15): e2025182118, Supplemental Data 15, 2 pages (Apr. 2021).
Conconi et al., "Genomic and Epigenomic Profile of Uterine Smooth Muscle Tumors of Uncertain Malignant Potential (STUMPs) Revealed Similarities and Differences with Leiomyomas and Leiomyosarcomas," Int. J. Mol. Sci., 22(1580): 1-16 (Feb. 2021). Published online Feb. 4, 2021.
Costa et al., "Targeting the PI3K/AKT/mTOR pathway in triple-negative breast cancer: a review," Breast Cancer Res. Treat., 169(3): 397-406. (Jun. 2018). Published online Feb. 7, 2018.
Crawford et al., "Bromodomain 4 activation predicts breast cancer survival," PNAS, 105(17): 6380-6385 (Apr. 2008) Published online Apr. 21, 2008.
D'Angelo et al., "Uterine sarcomas: a review," Gynecologic oncology, 116(1): 131-139 (Jan. 2010). Published online Oct. 23, 2009.
Dawson et al., "Inhibition of BET recruitment to chromatin as an effective treatment for MLL-fusion leukaemia," Nature, 478(7370): 529-533. (Oct. 2011). Published online Oct. 2, 2011.
Deng et al., "RNA N6-methyladenosine modification in cancers: current status and perspectives," Cell Res., 28(5): 507-517 (May 2018). Published online Apr. 23, 2018.
De Almeida et al., "Let-7 miRNA's Expression Profile and Its Potential Prognostic Role in Uterine Leiomyosarcoma," Cells, 8, 1452: 1-16 (Nov. 2019). Published online Nov. 17, 2019.
De Carvalho et al., "Treatment with epigenetic agents profoundly inhibits tumor growth in leiomyosarcoma," Oncotarget, 9(27):19379-19395 (Apr. 2018). Published online Apr. 10, 2018.
Del Gaudio et al., "BRD9 binds cell type-specific chromatin regions regulating leukemic cell survival via STAT5 inhibition," Cell Death and Disease, 10(338): 1-14 (Apr. 2019).
Dey et al., "Oncogenic KRAS-Driven Metabolic Reprogramming in Pancreatic Cancer Cells Utilizes Cytokines from the Tumor Microenvironment," Cancer Discovery, 10: 608-625 (Apr. 2020). Published online Feb. 11, 2020.
Di Giorgio et al., "Different class IIa HDACs repressive complexes regulate specific epigenetic responses related to cell survival in leiomyosarcoma cells," Nucleic Acids Research, 48(2): 646-664 (Jan. 2020). Published online Nov. 22, 2019.
Dobin et al., "STAR: ultrafast universal RNA-seq aligner," Bioinformatics, 29(1): 1-7 (Jan. 2013). Published online Oct. 25, 2012.
Faivre et al., "Selective inhibition of the BD2 bromodomain of BET proteins in prostate cancer," Nature, 578(7794): 306-310 (Feb. 2020). Published online Jan. 22, 2020.
Fu et al., "Gene expression regulation mediated through reversible m⁶A RNA methylation," Nat Rev Genet., (5): 293-306 (May 2014). Published online Mar. 25, 2014.
Fujisawa et al., "Functions of bromodomain-containing proteins and their roles in homeostasis and cancer," Nat Rev Mol Cell Biol., 18(4): 246-262 (Apr. 2017). Published online Jan. 5, 2017.
Gadducci et al., "Uterine leiomyosarcoma: analysis of treatment failures and survival," Gynecologic oncology, 62(1): 25-32 (Jul. 1996).

(56) References Cited

OTHER PUBLICATIONS

Garcia et al., "Evaluation of Hedgehog Pathway Inhibitors as a Therapeutic Option for Uterine Leiomyosarcoma Using the Xenograft Model," Reproductive Sciences, 29: 781-790 (Mar. 2022). Published online Oct. 12, 2021.

Garcia et al., "Targeting Hedgehog Pathway and DNA Methyltransferases in Uterine Leiomyosarcoma Cells," Cells, 10(53): 1-17 (Jan. 2021). Published online Dec. 3, 2020.

Garcia et al., "The Role of Hedgehog Pathway in Female Cancers," Cancer Sci Clin Ther., 4(4): 487-498 (Nov. 2020). Published online Oct. 9, 2020.

Gazon et al., "Hijacking of the AP-1 Signaling Pathway during Development of ATL," Front. Microbiol., 8: 2686, 13 pages (Jan. 2018).

Gonzalez et al., "Could miRNA Signatures be Useful for Predicting Uterine Sarcoma and Carcinosarcoma Prognosis and Treatment?," Cancers, 10(9): 315, 18 pages (Sep. 2018).

Gothe et al., "Spatial Chromosome Folding and Active Transcription Drive DNA Fragility and Formation of Oncogenic MLL Translocations," Molecular Cell, 75: 267-283 (Jul. 2019). Published online Jun. 12, 2019.

Han et al., "N-terminal kinase in rheumatoid arthritis," J Pharmacol Exp Ther., 291(1): 124-30. (Oct. 1999).

Hann et al., "Role of post-translational modifications in regulating c-Myc proteolysis, transcriptional activity and biological function," Semin Cancer Biol., 16(4): 288-302. (Aug. 2006). Published online Aug. 17, 2006.

Hasan et al., "Epigenetic signatures differentiate uterine and soft tissue Leiomyosarcoma," Oncotarget, 12(16): 1566-1579 (Aug. 2021).

Hemming, et al., "Preclinical Modeling of Leiomyosarcoma Identifies Susceptibility to Transcriptional CDK Inhibitors through Antagonism of E2F-Driven Oncogenic Gene Expression," Clinical Cancer Research, 28(11): 2397-2408 (Jun. 2022).

Hensley et al., "Fixed-dose rate gemcitabine plus docetaxel as first-line therapy for metastatic uterine leiomyosarcoma: a Gynecologic Oncology Group phase II trial," Gynecol Oncol., 109(3): 329-334 (Jun. 2008).

Huang et al., "miR-140-3p functions as a tumor suppressor in squamous cell lung cancer by regulating BRD9," Cancer Lett., 446: 81-89. (Apr. 2019).

Jacomy et al., "ForceAtlas2, a Continuous Graph Layout Algorithm for Handy Network Visualization Designed for the Gephi Software," PLoS ONE, 9(6): 1-12 (Jun. 2014). Published online Jun. 10, 2014.

Jain et al, "Bromodomain Histone Readers and Cancer," J. Mol. Biol., 429(13): 2003-2010 (Jun. 2017).

Jones et al., "Epigenetics in carcinogenesis and cancer prevention," Ann. N.Y. Acad. Sci., 983: 213-9. (Jan. 2006).

Kanwal et al., "Epigenetics and cancer," J. Appl. Physiol., 109: 598-605 (Aug. 2010). Published online Mar. 4, 2010.

Kapoor et al., "BRD9 Inhibition by Natural Polyphenols Targets DNA Damage/Repair and Apoptosis in Human Colon Cancer Cells," Nutrients, 14(4317): 1-9 (Oct. 2022).

Kato et al., "MYCL is a target of a BET bromodomain inhibitor, JQ1, on growth suppression efficacy in small cell lung cancer cells," Oncotarget, 7(47): 77378-77388 (Nov. 2016). Published online Oct. 14, 2016.

Kaur et al., "Targeting Chromatin Remodeling for Cancer Therapy," Current Molecular Pharmacology, 12: 215-229 (Aug. 2019).

Khare et al., "Epigenetics of colon cancer," Methods Mol Biol., 863: 177-185. (Jan. 2012) Published online Jan. 1, 2012.

Klionsky et al., "Guidelines for the use and interpretation of assays for monitoring autophagy (4th edition)," Autophagy, 17(1): 1-382 (Jan. 2021). Published online Feb. 8, 2021.

Kim et al., "Epigenetics of bladder cancer," Methods Mol Biol., 863:111-8. (Jan. 2012) Published online Jan. 1, 2012.

Kulikowski et al.,"Inhibitors of bromodomain and extra-terminal proteins for treating multiple human diseases," Med. Res. Rev., 41(1): 223-245. (Jan. 2021) Published online Sep. 14, 2020.

Krämer et al., "BRD9 Inhibition, Alone or in Combination with Cytostatic Compounds as a Therapeutic Approach in Rhabdoid Tumors," Int. J. Mol. Sci., 18(7), 1537: 1-12, (Jul. 2017).

Kregel et al., "Functional and Mechanistic Interrogation of BET Bromodomain Degraders for the Treatment of Metastatic Castration-resistant Prostate Cancer," Clin Cancer Res, 25(13): 4038-4048 (Jul. 2019).

Laird et al., "Cancer epigenetics," Human Molecular Genetics, 14(1): 65-76 (Apr. 2005).

Langer et al., "Jun and Fos family protein expression in human breast cancer: correlation of protein expression and clinicopathological parameters," Eur J Gynaecol Oncol., 27(4): 345-352. (Jan. 2006).

Leal et al., "The Bromodomain Inhibitor, INCB057643, Targets Both Cancer Cells and the Tumor Microenvironment in Two Preclinical Models of Pancreatic Cancer," Cancers, 13(1):1-15 (Dec. 2020).

Lourenco et al., "MYC protein interactors in gene transcription and cancer," Nat Rev Cancer., 21(9): 579-591 (Sep. 2021). Published online Jun. 29, 2021.

Lu et al., "Gene Signature Associated With Bromodomain Genes Predicts the Prognosis of Kidney Renal Clear Cell Carcinoma," Front Genet., 12(643935): 1-12 (Jun. 2021).

Lucas et al., "Targeting the BET family for the treatment of leukemia," Epigenomics, 6(2): 153-155 (Apr. 2014). Published online May 9, 2014.

Mason et al., "The BRD9/7 Inhibitor TP-472 Blocks Melanoma Tumor Growth by Suppressing ECM-Mediated Oncogenic Signaling and Inducing Apoptosis," Cancers (Basel), 13(21):1-19 (Nov. 2021).

Magnani et al., "Genome-wide reprogramming of the chromatin landscape underlies endocrine therapy resistance in breast cancer," Proc Natl Acad Sci, 110(16): 1490-1499 (Apr. 2013).

Moustakim et al., "Chemical probes and inhibitors of bromodomains outside the BET family," Med. Chem. Comm., 7(12): 2246-2264. (Dec. 2016) Published online Sep. 7, 2016.

Mittal et al., "Med12 gain-of-function mutation causes leiomyomas and genomic instability," The Journal of Clinical Investigation, 125(8): 3280-3284 (Aug. 2015).). Published online Jul. 20, 2015.

Nitulescu et al., "The Akt pathway in oncology therapy and beyond (Review)." Int. J. Oncol., 53(6): 2319-2331 (Dec. 2018). Published online Oct. 16, 2018.

Patel et al. "Alternative therapies in management of leiomyomas," Fertil Steril, 102(3): 649-55 (Sep. 2014) Published online Aug. 5, 2014.

Park et al., "Cytotoxic activity of bromodomain inhibitor NVS-CECR2-1 on human cancer cells," Sci Rep., 10(1): 1-15 (Oct. 2020).

Qi et al., "Bromodomain and extraterminal domain inhibitors (BETi) for cancer therapy: chemical modulation of chromatin structure," Cold Spring Harb Perspect Biol., 6(12): 1-3 (Dec. 2014).

Qiu et al., "JQ1 suppresses tumor growth through downregulating LDHA in ovarian cancer," Oncotarget, 6(9): 6915-6930. (Mar. 2015). Published online Feb. 5, 2015.

Reynolds et al., "A View on Drug Development for Cancer Prevention," Cancer Discovery, 13(5): 1058-1083, (May 2023).

Richter et al., "Combined Inhibition of Epigenetic Readers and Transcription Initiation Targets the EWS-ETS Transcriptional Program in Ewing Sarcoma," Cancers (Basel), 12(2): 1-17(Jan. 2020).

Santillan et al., "Bromodomain and histone acetyltransferase domain specificities control mixed lineage leukemia phenotype," Cancer Res., 66(20):10032-10039. (Oct. 2006).

Schrump et al."Utilization of chromatin remodeling agents for lung cancer therapy," Cancer J., 13(1): 56-64. (Jan. 2007).

Seagle et al., "Prognosis and treatment of uterine leiomyosarcoma: A National Cancer Database study," Gynecologic oncology, 145(1): 61-70. (Apr. 2017) Published online Mar. 15, 2017.

Shi et al., "Where, When, and How: Context-Dependent Functions of RNA Methylation Writers, Readers, and Erasers," Mol. Cell, 74(4): 640-650, (May 2019), author manuscript as published in PubMed.

Sparic, et al., "Molecular Insights in Uterine Leiomyosarcoma: A Systematic Review," International Journal of Molecular Sciences, 23(9728): 1-14 (Aug. 2022).

(56) References Cited

OTHER PUBLICATIONS

Supek et al., "REVIGO summarizes and visualizes long lists of gene ontology terms.," PLoS One, 6(7): 1-9 (Jul. 2011).
Stewart et al., "Carfilzomib, Lenalidomide, and Dexamethasone for Relapsed Multiple Myeloma," N. Engl. J. Med., 372: 142-152 (Jan. 2015). Published online Dec. 6, 2014.
Tsai et al., "Histone deacetylase interacts directly with DNA topoisomerase II," Nat Genet., 26(3): 349-553. (Nov. 2000).
Tu et al., "Myc and its interactors take shape," Biochim. Biophys. Acta., 1849(5): 469-483. (May 2015). Published online Jun. 14, 2014.
Wang et al., "The Role of the Transcription Factor EGR1 in Cancer.," Front Oncol., 11(642547):1-10 (Mar. 2021).
Wong et al., "Interplay between epigenetics and metabolism in oncogenesis: mechanisms and therapeutic approaches.," Oncogene, 36(24):3359-3374. (Jan. 2017).
Xie et al., "Gene Set Knowledge Discovery with Enrichr.," Curr. Protoc., 1(3): 1-84 (Mar. 2021).
Yamaguchi et al., "Case of leiomyosarcoma arising from subserosal leiomyoma.," J Obstet Gynaecol Res., 45(9): 1944-7. (Jun. 2019).
Yang et al., "Comprehensive Review of Uterine Fibroids: Developmental Origin, Pathogenesis, and Treatment," Endocrine Reviews, 43(4):678-719 (Nov. 2021).
Yang et al., "Altered DNA repair genes in human uterine fibroids are epigenetically regulated via EZH2 histone methyltransferase.," Fertility and Sterility, 104(3): Supplement E72 (Oct. 2015).
Yang et al., "The Mechanism and Function of Epigenetics in Uterine Leiomyoma Development," Reprod Sci., 23(2): 163-75. (Dec. 2016). Published online Apr. 28, 2015.
Yang et al., "Epigenetic alterations differ in phenotypically distinct human neuroblastoma cell lines," BMC Cancer, 10(286): 1-10 (Jun. 2010).
Yang et al., "Association of epigenetic inactivation of RASSF1A with poor outcome in human neuroblastoma," Clin Cancer Res., 10(24): 8493-8500. (Dec. 2004).
Yang et al., "Methylation-associated silencing of the thrombospondin-1 gene in human neuroblastoma," Cancer Res., 63(19):6299-310. (Oct. 2003).
Yang et al., "The Functional Role and mechanism of Bromodomain-Containing Protein 9 in Human Uterine Leiomyosarcoma," Fertil. Steril., 24(9): e229 (Oct. 2022), abstract No. P-288 (1 page).
Yang et al., "The Functional Role and mechanism of Bromodomain-Containing Protein 9 in Human Uterine Leiomyosarcoma," poster presentation associated with Fertil. Steril., 24(9): e229 (Oct. 2022), abstract No. P-288, presentation given Oct. 25, 2022 (11 pages).
Yang et al., "The Regulatory Mechanism of Histone Deacetylases in Epigenetic Regulation: Emerging Paradigms From Hdac Inhibition Studies in Uterine Leiomyosarcoma," Fertil Steril, (118): e338 (Oct. 2022), abstract No. P-543 (1 page).
Yang et al., "The Regulatory Mechanism of Histone Deacetylases In Epigenetic Regulation: Emerging Paradigms From Hdac Inhibition Studies in Uterine Leiomyosarcoma," poster presentation associated with Fertil Steril, (118): e338 (Oct. 2022), abstract No. P-543, presentation given Oct. 26, 2022 (8 pages).
Yang et al., "The Functional Role and Regulatory Mechanism of Bromodomain-Containing Protein 9 in Human Uterine Leiomyosarcoma Cells," Cells, 11(14): 2160, 22 pages (Jul. 2022).
Yang et al., "Targeting Class I Histone Deacetylases in Human Uterine Leiomyosarcoma," Cells, 11(23): 3801, 27 pages (Nov. 2022).
Yang et al., "Early Life Adverse Environmental Exposures Increase the Risk of Uterine Fibroid Development: Role of Epigenetic Regulation," Front. Pharmacol., (7): 1-10 (Mar. 2016).
Yang et al., "Targeting the Class I Histone Deacetylases in Uterine Leiomysarcoma," Reproductive Sciences, 29(1): 232A (Mar. 2022), abstract No. F-102 (1 page).
Yang et al., "Transcriptome Analysis Reveals BRD9 Inhibition-Induced Distinct Pathways in Uterine Fibroids," Reproductive Sciences, 29(1): 206A (Mar. 2022), abstract No. F-038 (1 page).
Yang et al., "The Functional Role and Regulatory Mechanism of FTO m6A RNA Demethylase in Human Uterine Leiomyosarcom," International Journal of Molecular Sciences, 24(9): 1-17 (Apr. 2023).
Yang et al., "Inhibition of BRD Proteins Suppresses the Phenotype of Uterine Fibroids Via Regulation of N6-Methyladenosine Regulators," Fertil. Steril., 116(3): 11 (Oct. 2021), abstract No. O-26 (1 page).
Yang et al., "Inhibition of BRD Proteins Suppresses the Phenotype of Uterine Fibroids Via Regulation of N6-Methyladenosine Regulators," slide presentation associated with Fertil Steril, 116(3): 11 (Oct. 2021), abstract No. O-26, presentation given Oct. 18, 2021 (15 pages).
Yang et al., "Aberrant Expression of N6-Methyladenosine Regulators in Uterine Fibroids From the Eker Rat Model," Fertil Steril, 116(3): e12-e13 (Oct. 2021), abstract No. O-29 (2 pages).
Yang et al., "Aberrant Expression of N6-Methyladenosine Regulators in Uterine Fibroids From the Eker Rat Model," slide presentation associated with Fertil Steril, 116(3): e12-e13 (Oct. 2021), abstract No. O-29, presentation given Oct. 18, 2021 (13 pages).
Yang et al., "Bromodomain Containing 9 Regulates Signaling Pathways and Reprograms the Epigenome in Human Uterine Fibroid Cells," Posted date Jul. 18, 2023. (preprint) Preprints (database online), [retrieved on Oct. 4, 2023]. Retrieved from the Internet: <URL: https://www.preprints.org/manuscript/202307.1154/v1> <DOI: https://doi.org/10.20944/preprints202307.1154.v1> (20 pages).
Yang et al., "Bromodomain-Containing 9 Regulates Signaling Pathways and Reprograms the Epigenome in Immortalized Human Uterine Fibroid Cells," International Journal of Molecular Sciences, 25(95): 1-21 (Jan. 2024).
Yang et al., "Pathological reprogramming of epitranscriptomics via METTL3 in Uterine Fibroids," Reproductive Sciences, (28)1: 128A-129A (Jul. 2021), abstract No. W-046 (1 page).
Ying et al., "CDK1 serves as a novel therapeutic target for endometrioid endometrial cancer," J Cancer, 12(8): 2206-2215 (Feb. 2021) Published online Feb. 22, 2021.
Zhang et al., "Aberrant activation of m6A demethylase FTO renders HIF2alpha(low/−) clear cell renal cell carcinoma sensitive to BRD9 inhibitors," Sci Transl Med., 13(613): 1-15 (Sep. 2021).
Zhang et al., "The aberrant upstream pathway regulations of CDK1 protein were implicated in the proliferation and apoptosis of ovarian cancer cells," J. Ovarian Res., 10(1): 1-11 (Sep. 2017).
Zhao et al., "Investigating crosstalk between H3K27 acetylation and H3K4 trimethylation in CRISPR/dCas-based epigenome editing and gene activation," Sci Rep., 11(1):1-11 (Aug. 2021).
Zhu et al., "Targeting BRD9 for Cancer Treatment: A New Strategy," Onco. Targets Ther., 13: 13191-13200. (Dec. 2020).
Zuccala et al., Misdirecting methylation to drive oncogenesis, Nat. Rev. Cancer, 16(7): 410 (Jun. 2016).
Chen et al., "Bromodomain-containing protein 9 activates proliferation and epithelial-mesenchymal transition of colorectal cancer via the estrogen pathway in vivo and in vitro," Journal of Gastrointestinal Oncology, 14(2): 980-996 (Apr. 2023).
Chowdhury et al., "Synergy between BRD9- and IKZF3-Targeting as a Therapeutic Strategy for Multiple Myeloma," Cancers, 16(1319):1-21 (Mar. 2024).
Duan et al., "Discovery of a Highly Potent and Selective BRD9 PROTAC Degrader Based on E3 Binder Investigation for the Treatment of Hematological Tumors," Journal of Medicinal Chemistry, 67:11326-11353 (Jun. 2024).
Feng et al., "BRD9-SMAD2/3 Orchestrates Stemness and Tumorigenesis in Pancreatic Ductal Adenocarcinoma," Gastroenterology, 166 (1):139-154 (Jan. 2024).
Finetti et al., "Translational Genomics of Malignant Rhabdoid Tumours: Current Impact and Future Possibilities," Translational Genomics for Rare Cancers: Challenges and Opportunity, 61: 30-41, (Apr. 2020) Published online Jan. 7, 2020. Author manuscript as pre-print pp. 1-38.
Kurata et al., "BRD9 Degradation Disrupts Ribosome Biogenesis in Multiple Myeloma," Clinical Cancer Research, 29(1):1807-1821 (May 2023).
Li et al., "New targeted treatments for advanced sarcomas," Current Opinion Oncology, 35(1):309-314 (Jul. 2023).

(56) References Cited

OTHER PUBLICATIONS

Nasioudis et al., "Next generation sequencing reveals a high prevalence of pathogenic mutations in homologous recombination DNA damage repair genes among patients with uterine sarcoma," Gynecologic Oncology, 177(1):14-19 (Jul. 2023) Published online Aug. 21, 2023.

Soto-Castillo at al., "SWI/SNF Complex Alterations in Tumors with Rhabdoid Features: Novel Therapeutic Approaches and Opportunities for Adoptive Cell Therapy," International Journal of Molecular Sciences, 24:1-20 (Jul. 2023).

Wang et al., "BRD9-mediated control of the TGF-B/Activin/Nodal pathway regulates self-renewal and differentiation of human embryonic stem cells and progression of cancer cells," Nucleic Acids Research, 51:11634-11651 (Oct. 2023).

Zhu et al., "BRD9 is an essential regulator of glycolysis that creates an epigenetic vulnerability in colon adenocarcinoma," Cancer Medicine, 12:1572-1582 (Jun. 2022).

McBride et al., "The SS18-SSX Fusion Oncoprotein Hijacks BAF Complex Targeting and Function to Drive Synovial Sarcoma," Cancer Cell, 33(6): 1128-1141 (2018). Author manuscript as pre-print pp. 1-40.

\* cited by examiner

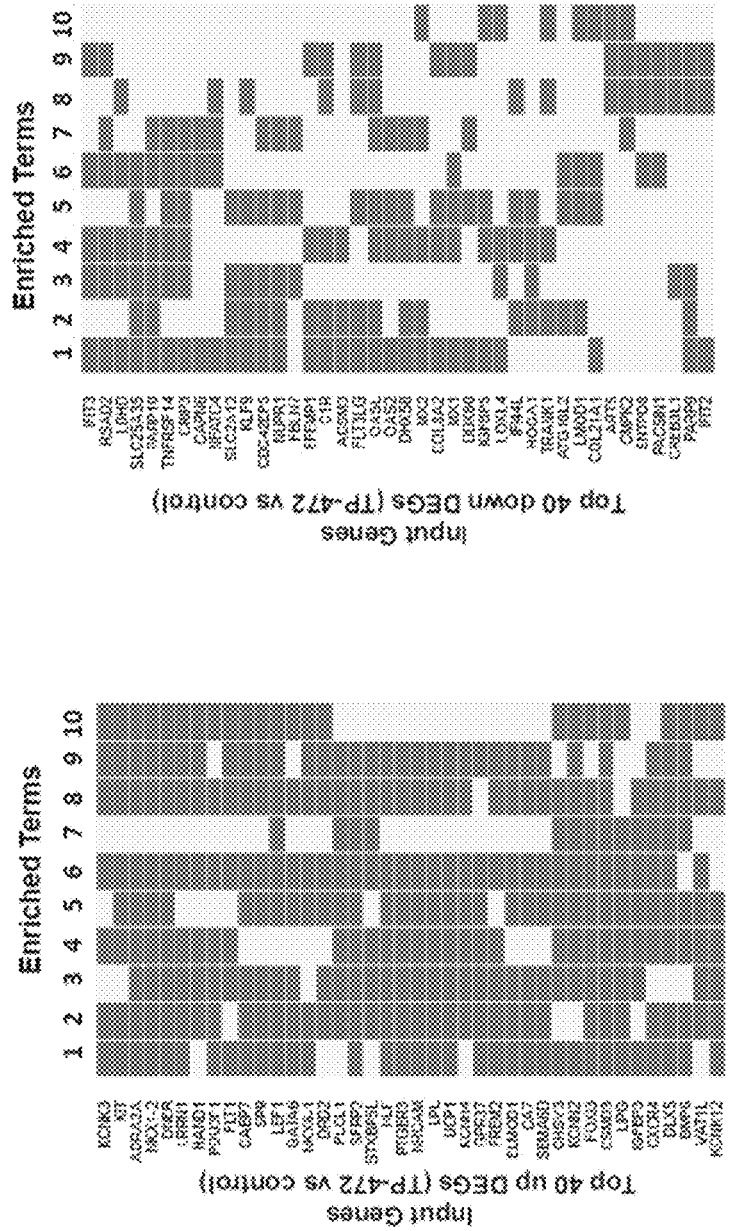
Fig. 9A
Fig. 9B

SEQUENCE LISTING

```
Sequence total quantity: 6
SEQ ID NO: 1              moltype = DNA  length = 21
FEATURE                   Location/Qualifiers
source                    1..21
                          mol_type = other DNA
                          organism = synthetic construct
SEQUENCE: 1
cggaacaagg agtcagacat t                                                 21

SEQ ID NO: 2              moltype = DNA  length = 21
FEATURE                   Location/Qualifiers
source                    1..21
                          mol_type = other DNA
                          organism = synthetic construct
SEQUENCE: 2
agtgccagga aagacaacta c                                                 21

SEQ ID NO: 3              moltype = DNA  length = 20
FEATURE                   Location/Qualifiers
source                    1..20
                          mol_type = other DNA
                          organism = synthetic construct
SEQUENCE: 3
agggcttagg acttggtttg                                                   20

SEQ ID NO: 4              moltype = DNA  length = 22
FEATURE                   Location/Qualifiers
source                    1..22
                          mol_type = other DNA
                          organism = synthetic construct
SEQUENCE: 4
gggattccta gtggtgttga ta                                                22

SEQ ID NO: 5              moltype = DNA  length = 21
FEATURE                   Location/Qualifiers
source                    1..21
                          mol_type = other DNA
                          organism = synthetic construct
SEQUENCE: 5
cacggacagg attgacagat t                                                 21

SEQ ID NO: 6              moltype = DNA  length = 21
FEATURE                   Location/Qualifiers
source                    1..21
                          mol_type = other DNA
                          organism = synthetic construct
SEQUENCE: 6
gccagagtct cgttcgttat c                                                 21
```

USE OF BROMODOMAIN-CONTAINING PROTEIN 9 INHIBITORS TO TREAT AND/OR PREVENT UTERINE LEIOMYOSARCOMA

CROSS-REFERENCE TO RELATED APPLICATION

This patent application claims the benefit of U.S. Provisional Patent Application No. 63/357,886, filed Jul. 1, 2022, which is incorporated by reference herein in its entirety.

STATEMENT REGARDING FEDERALLY SPONSORED RESEARCH OR DEVELOPMENT

This invention was made with Government support under Grant Number HD106285 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,427 Byte XML (Extensible Markup Language) file named "767720_SequenceListing.xml" created on May 17, 2024.

BACKGROUND

Uterine leiomyosarcoma (uLMS) is a rare uterine cancer, representing 1-2% of all uterine malignancies. The annual incidence of uLMS is approximately 6 per 1,000,000 women. The 5-year survival rate for all patients ranges between 25 and 76%, while survival for women with metastatic disease at the time of initial diagnosis approaches only 10-15%. Irrespective of treatment, uLMS is characterized by poor prognosis, and many uLMS patients exhibit resistance to currently available therapies, as evidenced by high rates of both recurrence and progression.

There is an ongoing need in the art to treat uLMS.

BRIEF SUMMARY

In aspects, the present disclosure provides a method of treating or preventing a uterine leiomyosarcoma (uLMS) in a female mammal, the method comprising, consisting essentially of, or consisting of administering to the female mammal an effective amount of an inhibitor of bromodomain-containing protein 9 (BRD9).

Additional aspects of the present disclosure are as described herein.

BRIEF DESCRIPTION OF THE DRAWINGS

FIG. 4A is a Western blot image of BRD9 and β-actin levels in UTSM, HuLM, MES-SA, and SK-UT-1 cell lines in three experiments (E1-E3). FIG. 4B is a graph showing the protein of BRD9 levels normalized to β-actin. FIGS. 4C-4D are graphs showing cell proliferation in SK-UT-1 cell lines (FIG. 4C) and MES-SA cell lines (FIG. 4D) in the presence and absence of the BRD9 inhibitor TP-472. FIG. 4E is a Western blot image of Bcl-2 and β-actin levels in SK-UT-1 cells in the presence or absence of the BRD9 inhibitor TP-472. FIG. 4F is a graph showing the protein of Bcl-2 levels normalized to β-actin. Significance is represented as * $p<0.05$, * * $p<0.01$, and * * * $p<0.001$.

FIG. 5A is a pie chart showing the percentage of genes that exhibited changes in RNA expression between TP-472 and vehicle treatment groups as determined by RNA-seq. FIG. 5B is a PCA plot of BRD9 inhibitor (TP-472) and vehicle control (DMSO) treated SK-UT-1 cells. FIG. 5C is a volcano plot showing the distribution of the DEGs between TP-472 and vehicle-treated SK-UT-1 cells. The dashed line indicates the p-value significance threshold. FIGS. 5D-5F are heat maps showing cluster DEG for SK-UT-1 cells treated with TP-472 vs. Control (FIG. 5D), TP-472 vs. Control upregulated genes (FIG. 5E), and TP-472 vs. Control downregulated genes (FIG. 5F).

FIG. 6A is a graph showing functional pathways analysis identified significantly altered pathways in SK-UT-1 cells treated with TP-472. Gene count and significance levels are shown by the size and color of each circle, respectively. FIGS. 6B-6F are graphs of pathway analysis showing that several gene sets associated with: TNF-α signaling via NFkB (FIG. 6B), KRAS signaling (FIG. 6C), MYC targets (FIG. 6D), MTORC1 signaling (FIG. 6E), and interferon-alpha response (FIG. 6F) were altered by TP-472 treatment.

FIG. 8A is a flowchart showing the process of modular pattern analysis. FIG. 8B is a graphic showing the nine identified network modules. FIG. 8C is an overlay of gene expression z-scores for all genes in the control and TP-472 conditions with low and high expression z-sores indicated by arrows for both conditions. Four constructed modules, including mitotic cell cycle phase (GO: 0044772), regulation of mitochondrial outer membrane permeabilization involved in apoptotic signaling pathway (GO: 1901028), apoptotic process (GO: 9996915), and translational termination (GO: 0006415) are circled and labeled in the TP-472 group.

FIGS. 9A-9B are visualizations of the relation between the histone modifications and the top 40 among the top 200 DEGs upregulated (up) (FIG. 9A) or suppressed (down)

(FIG. 9B) by TP-472 treatment, with the top 10 altered epigenetic terms listed below with their corresponding p-value. Arabic numerals are the index for histone modifications.

DETAILED DESCRIPTION

Figure 1:
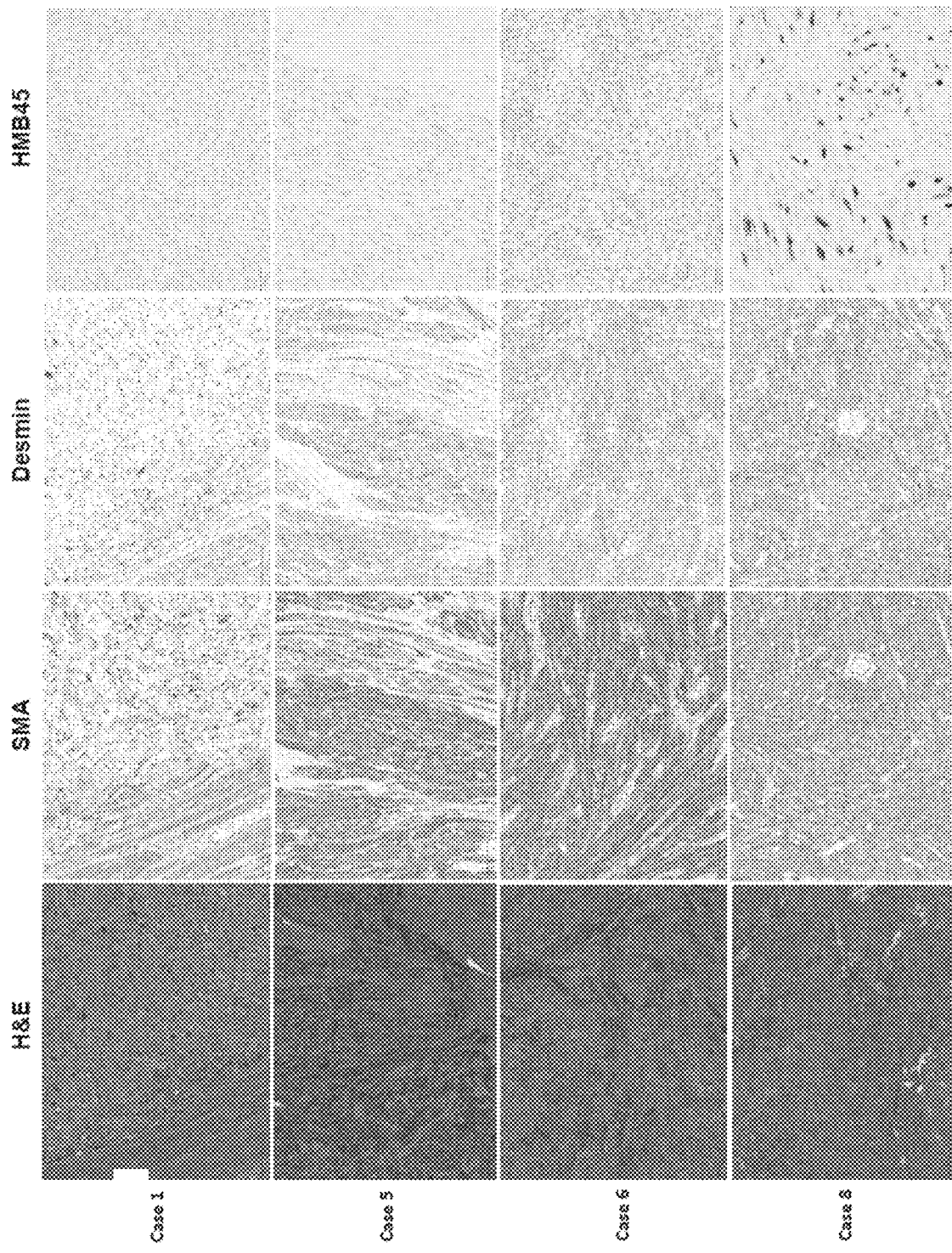
FIG. 1 is a series of micrographs that show immunhistochemical staining of SMA, desmin, and MHB45 in four representative human uterine leiomyosarcoma (uLMS) tissues and adjacent myometrium.

In aspects, the present disclosure provides a method of treating or preventing a uterine leiomyosarcoma (uLMS) in a female mammal, the method comprising, consisting essentially of, or consisting of administering to the female mammal an effective amount of an inhibitor of bromodomain-containing protein 9 (BRD9). In aspects the female mammal is a human.

As used herein, a "uterine leiomyosarcoma" (uLMS), is a malignant tumor of the uterus that consists of a mass or population of smooth muscle cells, epithelial cells, and/or connective tissue that grows rapidly and eventually metastasize. uLMS mostly occurs in women over 40 years old. Symptoms of uLMS include abnormal vaginal bleeding, a palpable pelvic mass, and pelvic pain. uLMS also presents with similar to those of patients with uterine fibroids (UFs), also known as leiomyomas, such as, heavy and prolonged bleeding, which may lead to anemia and iron deficiency, bowel and bladder dysfunction, infertility, low back pain, urinary frequency and urgency, and pain during intercourse (dyspareunia).

A significant body of foundational data supports an important role in epigenetic dysregulation of gene expression in oncogenesis. For example, altered epigenetic modifications, including DNA methylation and histone modifications, as well as aberrant expression of non-coding RNAs, have been variously shown to contribute to tumor initiation and development. Notably, as the "readers" of lysine acetylation, bromodomain (BRD)—containing proteins are responsible for transducing regulatory signals carried by acetylated lysine residues into various biological phenotypes. BRD proteins can exert a wide variety of functions via multiple gene regulatory mechanisms and deregulation of BRDs is involved in many diseases, including cancer.

Bromodomain-containing protein 9 (BRD9) is a newly identified subunit of the noncanonical barrier-to-autointegration factor (ncBAF) complex and a member of the bromodomain family IV. Studies have demonstrated that BRD9 plays an oncogenic role in multiple cancer types, by regulating tumor cell growth. The connection of BRD9 with PI3K pathway, miR RNAs, and STATS is implicated in cancer progression. However, the role and mechanism of BRDs in the pathogenesis of uLMS are unknown.

As used herein, a "BRD9 inhibitor" is any agent that inhibits a BRD9 protein, e.g., by inhibiting the expression or function of a BRD9 protein. Several small molecule inhibitors of BRD9 have been previously developed. BRD9 inhibitors include, but are not limited to, TP-472, I-BRD9, BI-7273, BI-9564, LP99, and VZ185 (Table 1).

TABLE 1

| BRD Inhibitor | Target |
| --- | --- |
| TP-472 | BRD9/7 |
| I-BRD9 | BRD9 |
| BI-7273 | BRD9 |

TABLE 1-continued

| BRD Inhibitor | Target |
| --- | --- |
| BI-9564 | BRD9 |
| LP99 | BRD9/7 |
| VZ185 | BRD9/7 |

The structure of TP-472 is provided below:

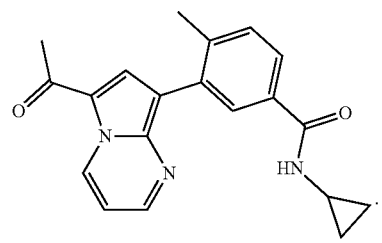 [SMILES: CC(=O)c1cc(-c2cc(C(=O)NC3CC3)ccc2C)c2ncccn12]

The structure of I-BRD9 is provided below:

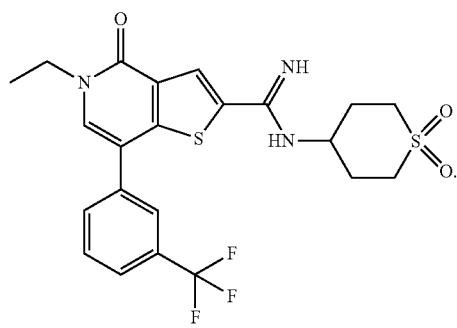 [SMILES: CCn1cc(-c2cccc(C(F)(F)F)c2)c2sc(C(=N)NC3CCS(=O)(=O)CC3)cc2c1=O]

The structure of BI-7273 is provided below:

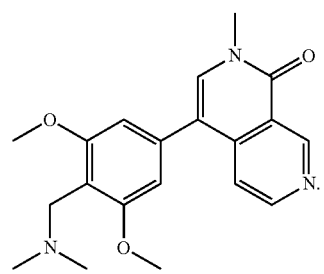 [SMILES: COc1cc(-c2cn(C)c(=O)c3cnccc23)cc(OC)c1CN(C)C]

The structure of BI-9564 is provided below:

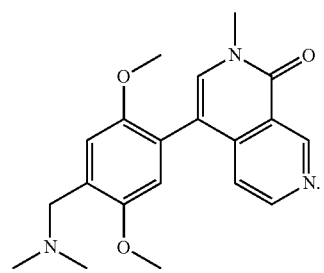 [SMILES: COc1cc(-c2cn(C)c(=O)c3cnccc23)c(OC)cc1CN(C)C]

The structure of LP99 is provided below:

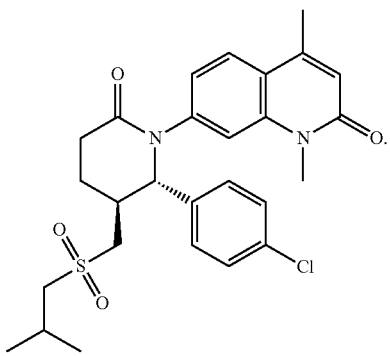 [SMILES: Cc1cc(=O)n(C)c2cc(N3C(=O)CC[C@H](CS(=O)(=O)CC(C)C)[C@H]3c3ccc(Cl)cc3)ccc12]

The structure of VZ185 is provided below:

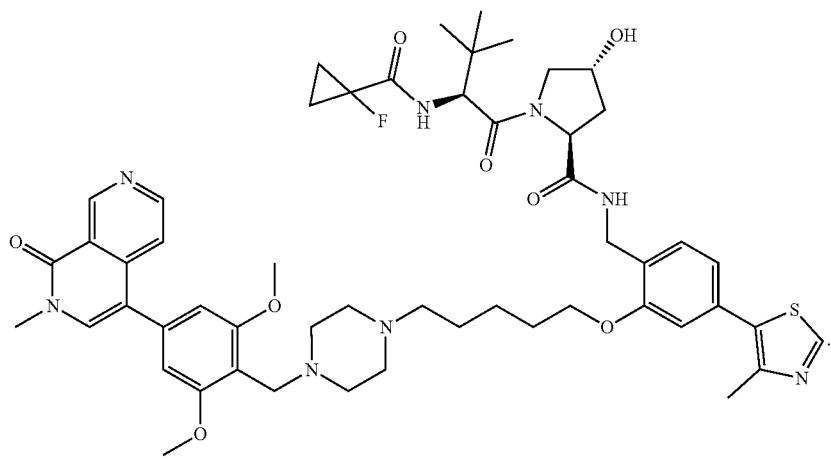 [SMILES: COc1cc(-c2cn(C)c(=O)c3cnccc23)cc(OC)c1CN1CCN(CCCCCOc2cc(-c3scnc3C)ccc2CNC(=O)[C@@H]2C[C@@H](O)CN2C(=O)[C@@H](NC(=O)C2(F)CC2)C(C)(C)C)CC1]

In aspects, the BRD9 inhibitor is a compound of the formula I:

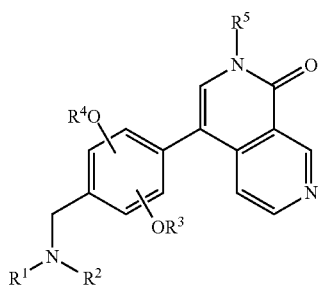

wherein $R^1$, $R^2$, $R^3$, $R^4$, and $R^5$ are each independently H, methyl, or ethyl.

The terms "treat," "treating," "treatment," "therapeutically effective," etc. used herein do not necessarily imply 100% or complete treatment, etc. Rather, there are varying degrees, which one of ordinary skill in the art recognizes as having a potential benefit or therapeutic effect. In this respect, the inhibitor of BRD9 and methods can provide any amount of any level of treatment. Furthermore, the treatment provided by the disclosed method can include the treatment of one or more conditions or symptoms of the disease or condition being treated.

The disclosed methods comprise using an effective amount of an inhibitor of BRD9. An "effective amount" means an amount sufficient to show a meaningful benefit. A meaningful benefit includes, for example, detectably treating, relieving, or lessening one or more symptoms of uLMSs; inhibiting, arresting development, preventing, or halting further development of uLMSs; reducing the size and/or mass of uLMSs; reducing the severity of uLMSs; preventing uLMSs from occurring in a subject at risk thereof but yet to be diagnosed. The meaningful benefit observed can be to any suitable degree (10%, 20%, 30%, 40%, 50%, 60%, 70%, 80%, 90% or more). In aspects, one or more symptoms are prevented, reduced, halted, or eliminated subsequent to administration of an inhibitor of BRD9 as described herein, thereby effectively treating the disease to at least some degree.

One skilled in the art will recognize that dosage will depend upon a variety of factors, including the age, condition or disease state, predisposition to disease, genetic defect or defects, and body weight of the subject. The size of the dose will also be determined by the route, timing and frequency of administration as well as the existence, nature, and extent of any adverse side-effects that might accompany the administration of a particular active agent and the desired effect. It will be appreciated by one of skill in the art that various conditions or disease states may require prolonged treatment involving multiple administrations.

The amount (e.g., therapeutically effective amount) of an inhibitor of BRD9 suitable for administration depends on, e.g., the particular route of administration and the weight of the mammal to be treated. Several doses can be provided over a period of days or weeks.

The mammal may be any suitable mammal. Mammals include, but are not limited to, the order Rodentia, such as mice, and the order Lagomorpha, such as rabbits. The mammal can be from the order Carnivora, including Felines (cats) and Canines (dogs). The mammal can be from the order Artiodactyla, including Bovines (cows) and Swines (pigs) or of the order Perissodactyla, including Equines (horses). The mammal can be of the order Primates, Cebids, or Simioids (monkeys) or of the order Anthropoids (humans and apes). In aspects, the mammal is human.

In aspects the method of treating or preventing a uterine leiomyosarcoma in a female mammal, including humans, comprises administering an effective amount of TP-472. The amount (e.g., therapeutically effective amount) of TP-472 suitable for administration depends on, e.g., the particular route of administration and the weight of the mammal to be treated. Several doses can be provided over a period of days or weeks.

In aspects, the method of treating a uterine leiomyosarcoma in a female mammal, including humans, comprises administering an effective amount of I-BRD9. The amount (e.g., therapeutically effective amount) of I-BRD9 suitable for administration depends on, e.g., the particular route of administration and the weight of the mammal to be treated. Several doses can be provided over a period of days or weeks.

In aspects the method of treating a uterine leiomyosarcoma in a female mammal, including humans, comprises administering an effective amount of LP99. The amount (e.g., therapeutically effective amount) of LP99 suitable for administration depends on, e.g., the particular route of administration and the weight of the mammal to be treated. Several doses can be provided over a period of days or weeks.

In aspects the method of treating a uterine leiomyosarcoma in a female mammal, including humans, comprises administering an effective amount of BI-9564. The amount (e.g., therapeutically effective amount) of BI-9564 suitable for administration depends on, e.g., the particular route of administration and the weight of the mammal to be treated. Several doses can be provided over a period of days or weeks.

The following includes certain aspects of the disclosure.

1. A method of treating or preventing a uterine leiomyosarcoma in a female mammal, the method comprising administering to the female mammal an effective amount of an inhibitor of bromodomain-containing protein 9 (BRD9).

2. The method of aspect 1, wherein the inhibitor of BRD9 is TP-472, I-BRD9, LP99, or BI-9564.

3. The method of aspect 2, wherein the inhibitor of BRD9 is TP-472.

4. The method of aspect 1, wherein the female mammal is a human.

5. The method of aspect 2, wherein the female mammal is a human.

6. The method of aspect 3, wherein the female mammal is a human.

7. The method of aspect 4, wherein the method is a method of treating.

8. The method of aspect 5, wherein the method is a method of treating.

9. The method of aspect 6, wherein the method is a method of treating.

It shall be noted that the preceding are merely examples of aspects of the disclosure. Other exemplary aspects are apparent from the entirety of the description herein. It will also be understood by one of ordinary skill in the art that each of these aspects may be used in various combinations with the other aspects provided herein.

The following example further illustrates aspects of the disclosure, but, of course, should not be construed as in any way limiting its scope.

EXAMPLE

This example demonstrates the role of BRD9 in aberrant uLMS cell growth and use of inhibitors of BRD9 to treat uLMS.

Materials and Methods

Tissue and Immunohistochemistry

The uLMS tissues (n=9) were obtained from the University of Chicago Tissue Bank. Approval from the Institutional Review Board (#20-1820) at the University of Chicago was obtained for the retrospective chart review of uLMS patients. Informed consent was obtained from all the patients participating in the study before surgery. The cases with an initial diagnosis of uLMS at University of Chicago Hospital were reviewed (Table 1), and the diagnosis was confirmed by H&E evaluation and immunohistochemistry, when required.

TABLE 2

Characteristics of uLMS samples.

| Case Number | Type of LSM | Age at Diagnosis | Tumor Size (cm) | Stage | Recurrence | Necrosis | Metastasis | Survival Status |
|---|---|---|---|---|---|---|---|---|
| 1 | Conventional | 58 | 7 | IB | N | Focal coagulative necrosis | None | A |
| 2 | Conventional | 58 | 8 | I | Y | Extensive hyaline necrosis, focal coagulative necrosis | Lung | D |
| 3 | Conventional | 42 | 7.1 | IB | N | Coagulative tumor cell necrosis and hyaline necrosis | Brain & Lung | A |
| 4 | Conventional | 62 | 7.9 | IB | Y | Focal coagulative necrosis | Lung | A |
| 5 | Non-conventional | 55 | 17 | IIIC1 | N | Focal coagulative necrosis | Ovary & Lung | D |
| 6 | Non-conventional | 54 | 18.8 | IIIB | Y | Focal coagulative necrosis | Abdominal wall + Bowel | D |
| 7 | Conventional | 54 | 27 | II | Y | Focal coagulative necrosis | Omentum | A |
| 8 | Conventional | 61 | 9.5 | IIIB | N | Focal coagulative necrosis | Omentum, Small intestine, Liver | A |
| 9 | Conventional | 42 | 24.6 | IB | N | Focal coagulative necrosis | None | D |

The mean age of uLMS patients was 54.0±6.9 years, with a range of 42 to 61 years. The clinicopathological data about the patient cohort and their uLMS samples were summarized in Table 1. The original blocks were retrieved from the tissue bank and were sectioned onto coated slides at a thickness of 5 µM. One section was stained with hematoxylin and eosin to evaluate the morphology of each spot, and the remaining slides were used for IHC analysis. Briefly, sections were deparaffinized with xylene, and rehydrated by being passed through decreasing concentrations of ethanol in water. Then, antigen retrieval and quenching of endogenous peroxidases were performed. Sections were incubated with primary antibodies (HMB45, SMA, desmin, and BRD9) (Table 2) in a humidity chamber overnight at 4° C. and developed with peroxidase labeled-dextran polymer followed by diaminobenzidine (DAKO Envision Plus System; DAKO Corporation, Carpinteria, CA, USA). Sections were counterstained with Gill's Hematoxylin (Fisher, Pittsburgh, PA, USA). To determine the percentage of BRD9 positive cells, the samples were analyzed using the positive cell detection command on QuPath software. Different thresholds were set to categorize cells according to nuclei staining intensity: negative, weak, moderate, and strong intensity. Smooth muscle was used a positive tissue for SMA and desmin. Melanoma was used a positive control for HMB45. Human testis was used as positive control for BRD9 IHC staining.

TABLE 3

Antibodies

| Antibodies | Company | Catalog Number | Source | Application | Dilution |
|---|---|---|---|---|---|
| BRD9 | Cell Signaling | 58906 | Rabbit | WB | 1:1000 |
| Bcl2 | Abcam | ab182858 | Rabbit | WB | 1:1000 |
| B-actin | Sigma | A5316 | Mouse | WB | 1:8000 |
| BRD9 | Abcam | ab259839 | Rabbit | IHC-P | 1:1000 |
| SMA | Dako | M0851 | Mouse | IHC-P | 1:1600 |
| Desmin | Santa Cruz | SC-14026 | Rabbit | IHC-P | 1:800 |
| HMB45 | Dako | M0634 | Mouse | IHC-P | 1:100 |

Cells and Reagents

The leiomyosarcoma (uLMS) cell line (SK-UT1, ATCC® HTB-114TM) (ATCC, Manassas, VA, USA) was cultured and maintained in ATCC-formulated Eagle's Minimum Essential Medium with 10% of fetal bovine serum. In addition, the uterine sarcoma cell line (MES-SA) (ATCC, Manassas, VA, USA) was cultured and maintained in McCoy's 5A medium. The immortalized human leiomyoma cell line (HuLM) and immortalized human uterine smooth muscle (UTSM) cells were a generous gift from Professor Darlene Dixon. The HuLM and UTSM cell lines were cultured and maintained in phenol red-free, Dulbecco's Modified Eagle Medium: Nutrient Mixture F-12. These cell lines, covering the spectrum from normal cell line (UTSM), benign uterine tumor cell line (HuLM), and uterine malignant cell lines (uLMS), were used to better understand the tumor progression linking to the BRD9 dysregulation in uLMS. BRD9 inhibitor (iBRD9) TP-472 was purchased from Tocris (Cat #6000, Minneapolis, MN, USA).

Proliferation Assay

Cell proliferation was measured using trypan blue exclusion assay; 4 104 cells per well were seeded into 12-well tissue culture plates, treated with the iBRD9 (TP-472) at a dose range from 1-25 µM for 48 h. This assay was performed three times in triplicate.

RNA Extraction and Gene Expression

Total RNA was isolated using Trizol reagent (Invitrogen, Carlsbad, CA, USA). The concentration of total RNA was determined using NanoDrop (Thermo Scientific, Waltham, MA, USA). One microgram of total RNA from each sample was reverse transcribed to complementary DNA (cDNA) using the High-Capacity cDNA Transcription Kit (Thermo Scientific, Waltham, MA, USA). Quantitative real-time polymerase chain reaction (qRT-PCR) was performed to determine the messenger RNA (mRNA) expression of several genes listed with their primer sequences in Table 2. The real-time PCR reactions were performed using CFX96 PCR instrument using SYBR Green Supermix (Bio-Rad, Hercules, CA, USA). 18S was used as an internal control. The results are presented as relative gene expression using CFX Maestro™. The assay was performed three times in triplicate.

Protein Extraction and Western Blot

Cells were collected and lysed in RIPA lysis buffer with protease and phosphatase inhibitor cocktail (Thermo Scientific, Waltham, MA, USA), the protein was quantified using the Bradford method (Bio-Rad Protein Assay kit). The information about primary antibodies, including antibody dilution and source of antibodies is listed in Table 2. The antigen—antibody complex was detected with Trident Femto Western HRP substrate (Gene-Tex, Irvine, CA, USA). Specific protein bands were visualized using Chemi-Doc XRS + molecular imager (Bio-Rad, Hercules, CA, USA).

RNA-Sequencing

To determine the mechanism underlying the inhibitory effect of BRD9 inhibition on the uLMS, the SK-UT-1 cells were treated with iBRD9 TP-472 (5 µM) for 48 h. RNA was isolated using Trizol. RNA quality and quantity were assessed using the Agilent bio-analyzer. Strand-specific RNA-SEQ libraries were prepared using a TruSEQ total RNA-SEQ library protocol (Illumina provided). Library quality and quantity were assessed using the Agilent bio-analyzer and libraries were sequenced using an Illumina NovaSEQ6000 (illumine provided reagents and protocols).

Transcriptome Data Analysis

A variety of R packages was used for this analysis. All graphics and data wrangling were handled using the tidyverse suite of packages. All packages used are available from the Comprehensive R Archive Network (CRAN), the Bioconductor project, or Github. The reads were mapped to the human reference transcriptome using STAR, version 2.6.1d (GitHub, Inc., San Francisco, CA, USA). The quality of raw reads, as well as the results of STAR mapping, are generated using fastqc and multiqc. Raw reads were mapped to the human reference transcriptome using Salmon, version 1.4.0. After reading mapping with Salmon, the tximport software package (Bioconductor project, accessed on 27 Oct. 2021) was used to read Salmon outputs into the R environment. Annotation data from Gencode V34 was used to summarize data from transcript-level to gene-level.

Integrated Bioinformatics Analysis

For Parsimonious gene correlation network analysis (PGCNA), normalized matrix of DEGs (Adjusted p-Values<0.05 and 1.5>fold-change>1.5; n=3583) and the top 80% of the most variance genes across samples (n=10,848) were used to network construction. The matrix was used to calculate Spearman rank correlations for all gene pairs using the Python PGCNA2 package [29]. For each gene (row) in a correlation matrix, only the three most correlated edges per gene were retained. The correlation matrices were clustered 100 times using the fast unfolding of communities in a large network's algorithm and the best (judged by modularity score) were used for downstream analysis. Gephi package with the ForceAt-1as2 layout method was used to visualize the network [30]. Enrichment analyses were performed using the Enrichr web server (Ma'ayan lab at Icahn School of Medicine at Mount Sinai, accessed on 10 Jan. 2022) through EnrichR package in R software [31]. Top biological process GO terms with the false discovery rate (FDR)>0.05 were analyzed using REVIGO to summarize and find a representative subset of the terms [32]. STRING database (accessed on 27 Apr. 2022), which is the online search tool to protein-protein network (PPI) construction, was used to reconstruct each modules network (A combined score≥0.4 of PPI pairs was considered significant), then the Cytoscape software was employed to analyze the obtained networks. In addition, the Venn diagram online tool provided by VIB and Ghent University (accessed on 27 Apr. 2022) was used to investigate the intersection of DEGs and selected modules.

Quantitative Real-Time Polymerase Chain Reaction (qRT-PCR)

Quantitative real-time PCR was performed to determine the mRNA expression of genes as described previously [33]. Primers were purchased from Integrated DNA Technologies (IDT, Coralville, IA, USA) with primer sequences shown in Table 4. An equal amount of cDNA from each sample was added to the Master mix containing appropriate primer sets and SYBR green supermix (Bio-Rad) in a 20 µL reaction volume. All samples were analyzed in triplicates. Real-time PCR analyses were performed using a Bio-Rad CFX96. Cycling conditions included denaturation at 95° C. for 2 min followed by 40 cycles of 95° C. for 5 s and 60° C. for 30 seconds then 65° C. for 5 seconds. Synthesis of a DNA product of the expected size was confirmed by melting curve analysis. Further, 18S ribosomal RNA values (internal control) were used to normalize the expression data and normalized values were used to create data graphs. Negative control has been performed by running the reaction without cDNA from Integrated DNA Technologies (IDT, Coralville, IA, USA).

TABLE 4 qRT-PCR Primers

| Gene Symbol | Primer Sequences | F or R | Assay | Species | Size (bp) | Accession |
| --- | --- | --- | --- | --- | --- | --- |
| CDKN1A | CGGAACAA GGAGTCAG ACATT (SEQ ID NO: 1) | F | q-PCR | Human | 105 | NM_00389.5 |
| CDKN1A | AGTGCCAG GAAAGACA ACTAC (SEQ ID NO: 2) | R | q-PCR | Human | 105 | NM_00389.5 |
| BAK | AGGGCTTA GGACTTGG TTTG (SEQ ID NO: 3) | F | q-PCR | Human | 100 | U16811.1 |
| BAK | GGGATTCC TAGTGGTG TTGATA (SEQ ID NO: 4) | R | q-PCR | Human | 100 | U16811.1 |
| 18 S | CACGGACA GGATTGAC AGATT (SEQ ID NO: 5) | F | q-PCR | Human | 119 | NR_145820 |
| 18 S | GCCAGAGT CTCGTTCG TTATC (SEQ ID NO: 6) | R | q-PCR | Human | 119 | NR_145820 |

Statistical Analysis

All experiments were conducted with at least three biological replicates. Comparison of two groups was carried out using Student t-test for parametric distribution and Mann-Whitney test for nonparametric distribution. Comparison of multiple groups was carried out by analysis of variance (ANOVA) followed by a post-test using Tukey for parametric distribution and Kruskal-Wallis test followed by a post-test Dunns for nonparametric distribution, using GraphPad Prism 5 Software. Data were presented as mean standard error (SE). In figures, ns, *, , and * indicate, not significant, $p<0.05$, $<0.01$, and $<0.001$ respectively.

Results

Pathological Examination

A total of nine patients with uLMS were identified. Of these, seven met the definition of conventional uLMS, while two met the definition of non-conventional uLMS resembling epithelioid uLMS and sex cord tumor. Patient information collected is shown in Table 2. The mean age of uLMS patients was 54.6±7.4 years with a range of 42 to 62 years. Tumor size was 14.1±7.9 cm in average (range: 2.9 cm to 27 cm). H&E staining exhibited a boundary between myometrium and uLMS (FIG. 1). In cases with equivocal morphologic features, SMA, desmin, and HMB45 immunohistochemical stains were performed, confirming the diagnosis of uLMS. SMA and desmin were all positive in 9/9 (100%) of cases by IHC analysis. For HMB45 IHC, seven and two of nine samples showed negative and positive HMB45 expression, respectively. The cases with HMB45 expression demonstrate only focal positivity and were considered insufficient to establish a diagnosis of PEComa (FIG. 1, Table 2).

Figure 2:
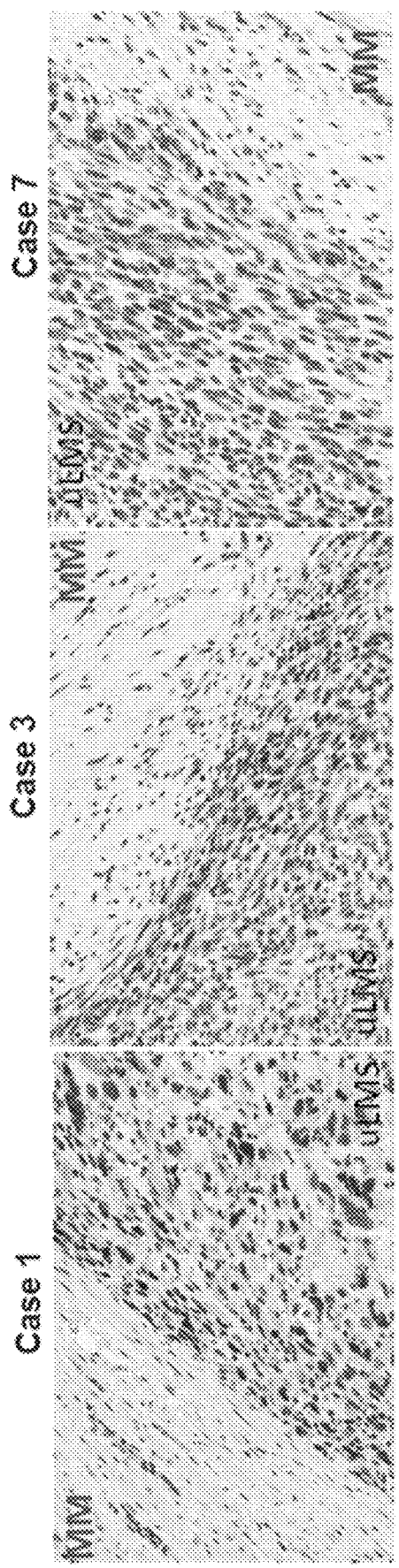
FIG. 2 is a series of micrographs that show immunhistochemical staining of BRD9 in three representative human uterine leiomyosarcoma (uLMS) tissues and adjacent myometrium.

The BRD9 Expression Is Unregulated in uLMS Tissues Compared to Adjacent Myometrium from Women with uLMS To determine whether BRD9 is dysregulated, the comparison of BRD9 positive cells and expression levels was analyzed on uLMS tissues (n=9) and adjacent myometrium (MM+uLMS) (n=7). Among seven cases (1-7) analyzed with both myometrium and uLMS, six cases exhibited an increased percentage of BRD9 positive cells in uLMS compared to MM+uLMS. Although the percentage of cells with a weak level of BRD9 expression is increased in only three out of seven uLMS cases compared to MM+uLMS (FIG. 2A, Table 5), the percentage of cells with moderate and strong expression levels of BRD9 in uLMS is much higher than MM+uLMS (FIG. 2A, Table 5). The uLMS tissues from cases #8-9 did not have matched myometrium; therefore, the BRD9 expression of cases #8-9 were compared with the average of BRD9 expression from cases #1-7 myometrium tissues. As shown in Table 5, the BRD9 expression in uLMS from cases #8-9 exhibited higher expression of BRD9 compared to the BRD9 expression in the myometrium. Among nine cases analyzed, eight out of nine cases exhibited an increase in BRD9 positive cells, moderate intensity, and strong intensity cells. The average fold changes of positive cells, weak intensity, moderate intensity and strong intensity in uLMS compared to MM+uLMS are 1.57, 0.85, 6.84, and 612.18, respectively (Table 5).

TABLE 5 qRT-PCR Primers

| Case | Positive | Intensity | | |
|---|---|---|---|---|
| | | Weak | Moderate | Strong |
| 1 | 1.26 | 1.10 | 1.52 | 2.48 |
| 2 | 0.90 | 0.83 | 0.99 | 1.15 |
| 3 | 1.10 | 0.80 | 1.29 | 1.57 |
| 4 | 4.02 | 0.58 | 38.72 | 5462.56 |
| 5 | 1.47 | 1.12 | 4.98 | 1.76 |
| 6 | 1.39 | 1.03 | 4.49 | 0.59 |
| 7 | 1.27 | 0.25 | 5.01 | 31.75 |
| 8 | 1.43 | 0.79 | | 5.07 |
| 9 | 1.26 | 1.14 | 1.78 | 2.67 |
| Average | 1.57 | 0.85 | 6.84 | 612.18 |

Figure 3A:
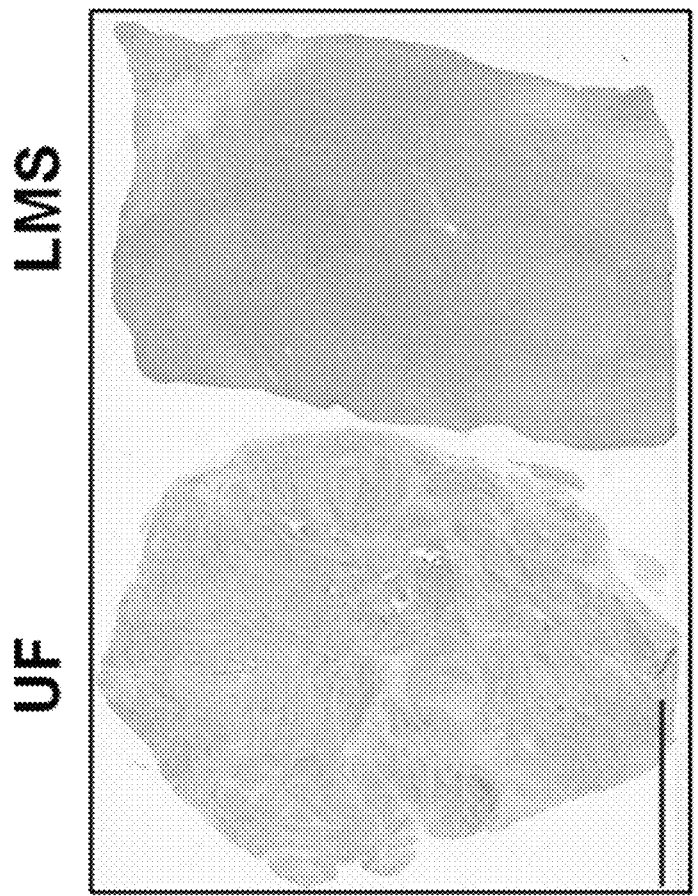
FIGS. 3A-3C are a series of micrographs showing a uterine fibroid (UF) and a uterine leiomyosarcoma (LMS) from the same patient with, hematoxylin and eosin staining at low magnification, scale bar is 6 millimeters (FIG. 3A), immuhistochemical staining of bromodomain-containing protein 9 (BRD9) at low magnification, scale bar is 6 millimeters (FIG. 3B), and immuhistochemical staining of bromodomain-containing protein 9 (BRD9) at high magnification, scale bar is 50 micrometers (FIG. 3C).
Figure 3B:
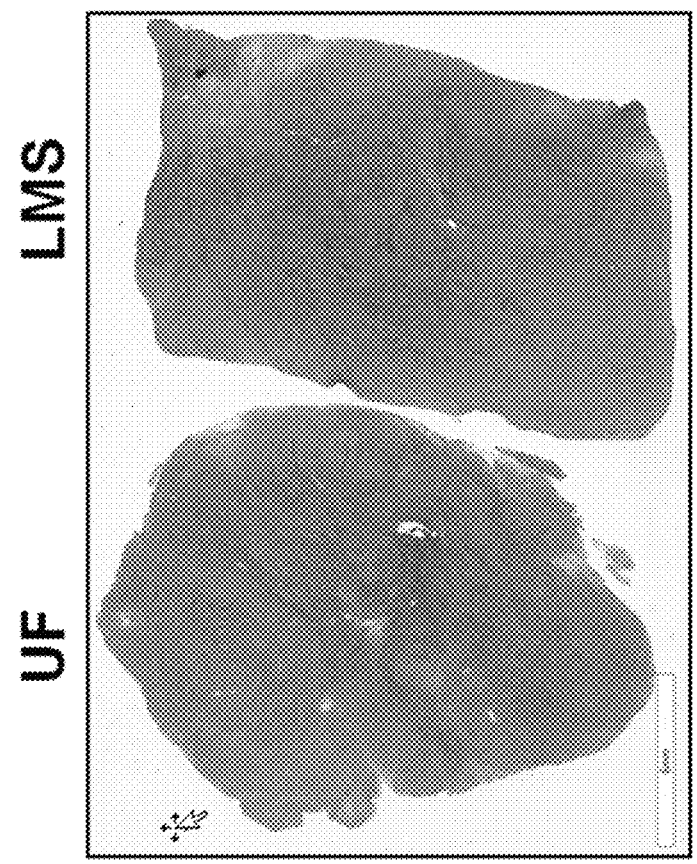
Figure 3C:
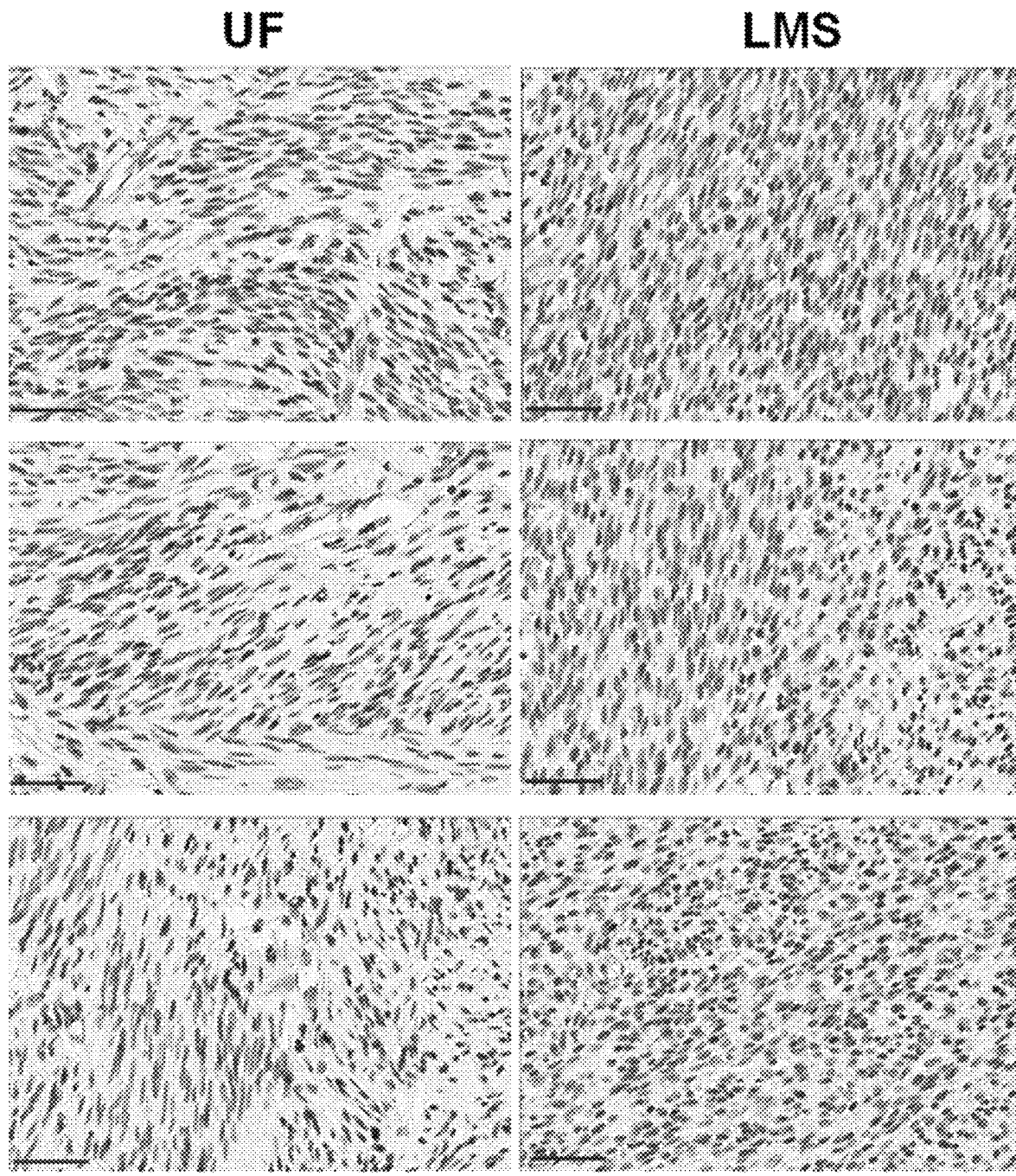

The Expression of BRD9 is aberrantly higher in malignant uLMS compared to benign UF Additional comparisons were performed to determine how expression of BRD9 differs in malignant uLMS compared to benign uterine fibroids (UFs), also known as leiomyomas. A patient with both uLMS and UF tumors was identified (FIG. 3A). Immunohistochemical staining shows that BRD9 expression was markedly higher in uLMS than UF. This suggests that BRD9 expression is slightly increased in benign UF tumors relative to healthy myometrium, and highly increased in uLMS relative to both UF and myometrium.

BRD9 Levels Are Unregulated in uLMS Cell Lines

Figure 4B:
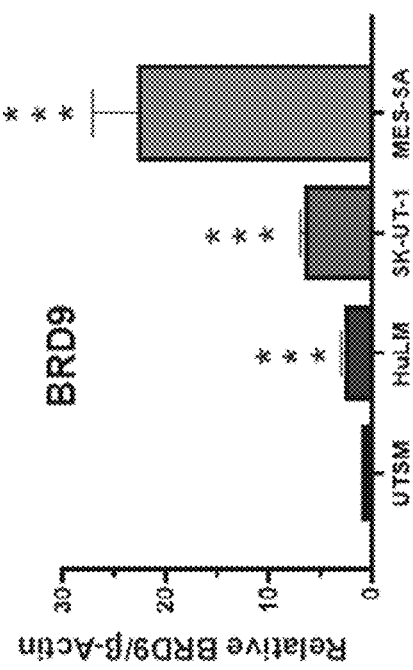
FIGS. 4A-4F show the protein levels of BRD9 in UTSM, HuLM, MES-SA, and SK-UT-1 cell lines and the effect of BRD9 inhibition.
Figure 4A:
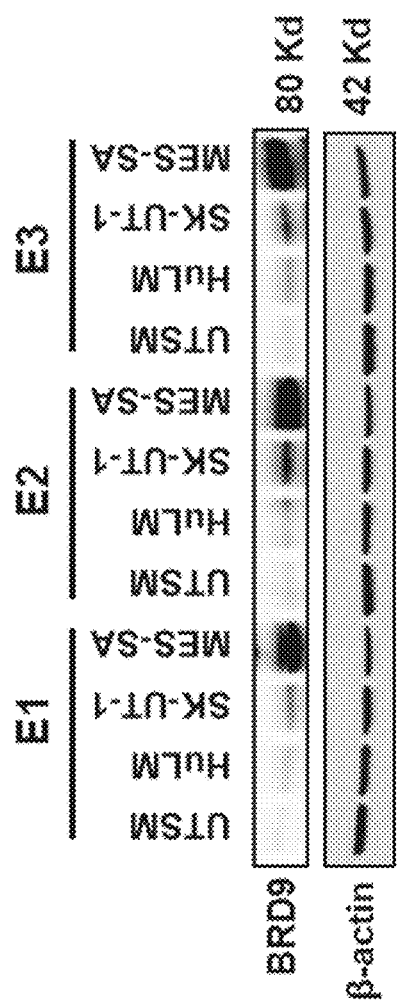

The constitutive (basal) expression levels of BRD9 in cell lines from human uterine smooth muscle (UTSM), human uterine leiomyoma (HuLM), and two different uLMS (SK-UT-1 and MES-SA) were evaluated by Western blot analysis. This analysis revealed that the expression levels of BRD9 exhibited a graded increase from normal and benign tumors to malignant uterine sarcoma cells. (FIGS. 4A-4B).

Inhibition of BRD9 Decreased uLMS Cell Proliferation

Figure 4D:
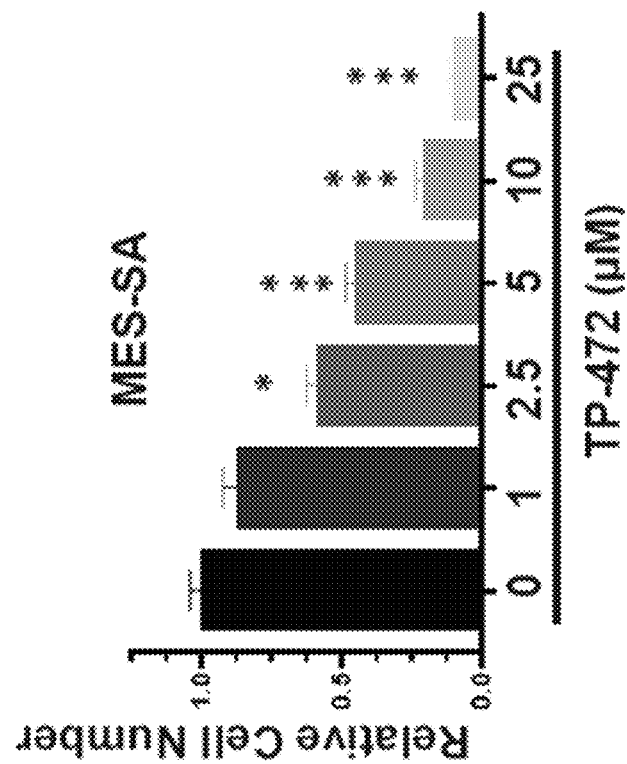
Figure 4C:
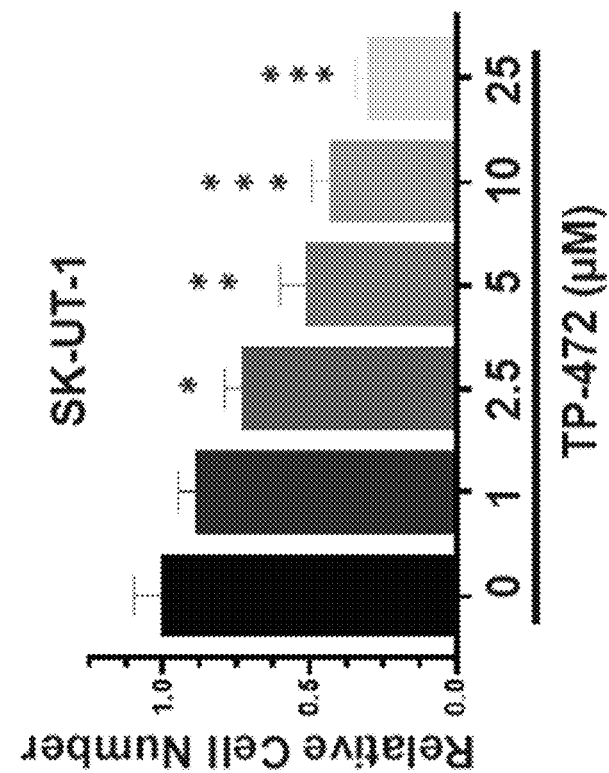
Figure 4F:
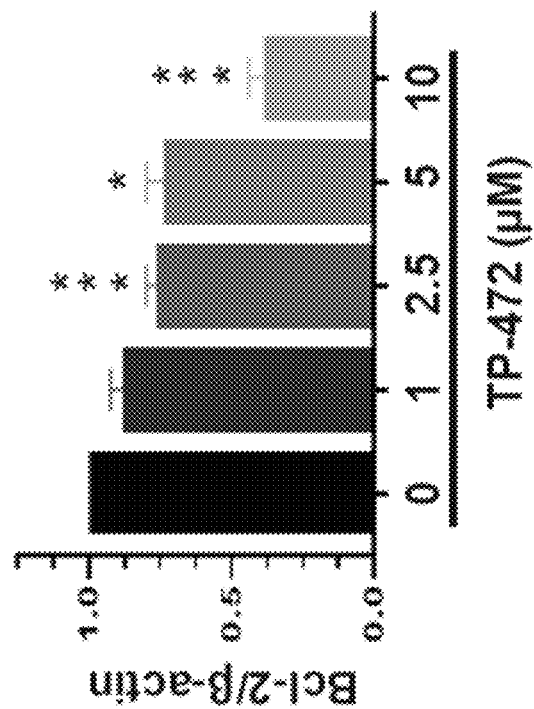
Figure 4E:
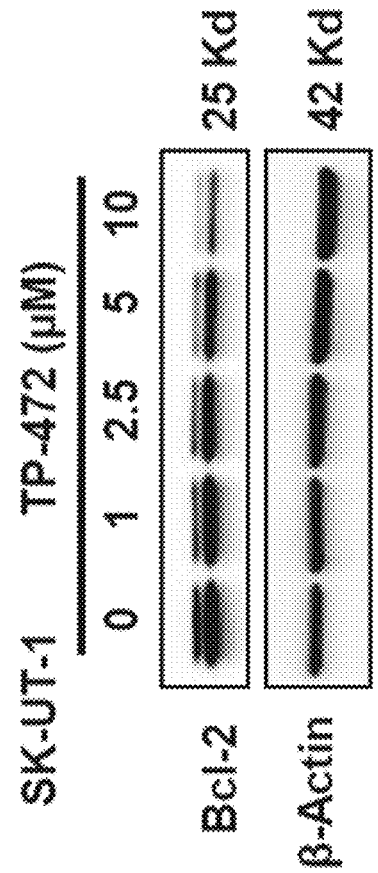

TP-472 has been shown to inhibit BRD9 [34], therefore TP-472 was selected to assess its effect on uLMS cell proliferation in an in vitro cell model. Trypan blue exclusion assay was performed in SK-UT-1 and MES-SA cell lines treated for 48 h with TP-472 at dose ranges from 1-25 µM. The prolonged treatment (48 h) with iBRD9 (TP-472) showed a dose-dependent inhibitory effect on proliferation of both SK-UT-1 and MES-SA cells (FIGS. 4C-4D). To determine if TP-472 treatment suppressed uLMS cell proliferation via apoptosis, the levels of BCL-2, which promotes cellular survival and inhibits the actions of pro-apoptotic proteins, were measured. As show in FIG. 4E-4F, TP-472 treatment significantly decreased the protein levels of BCL-2 in SK-UT-1 cells in a dose-dependent manner.

BRD9 Inhibition Causes Extensive Changes in the uLMS Cell Transcriptome

Figure 5A:
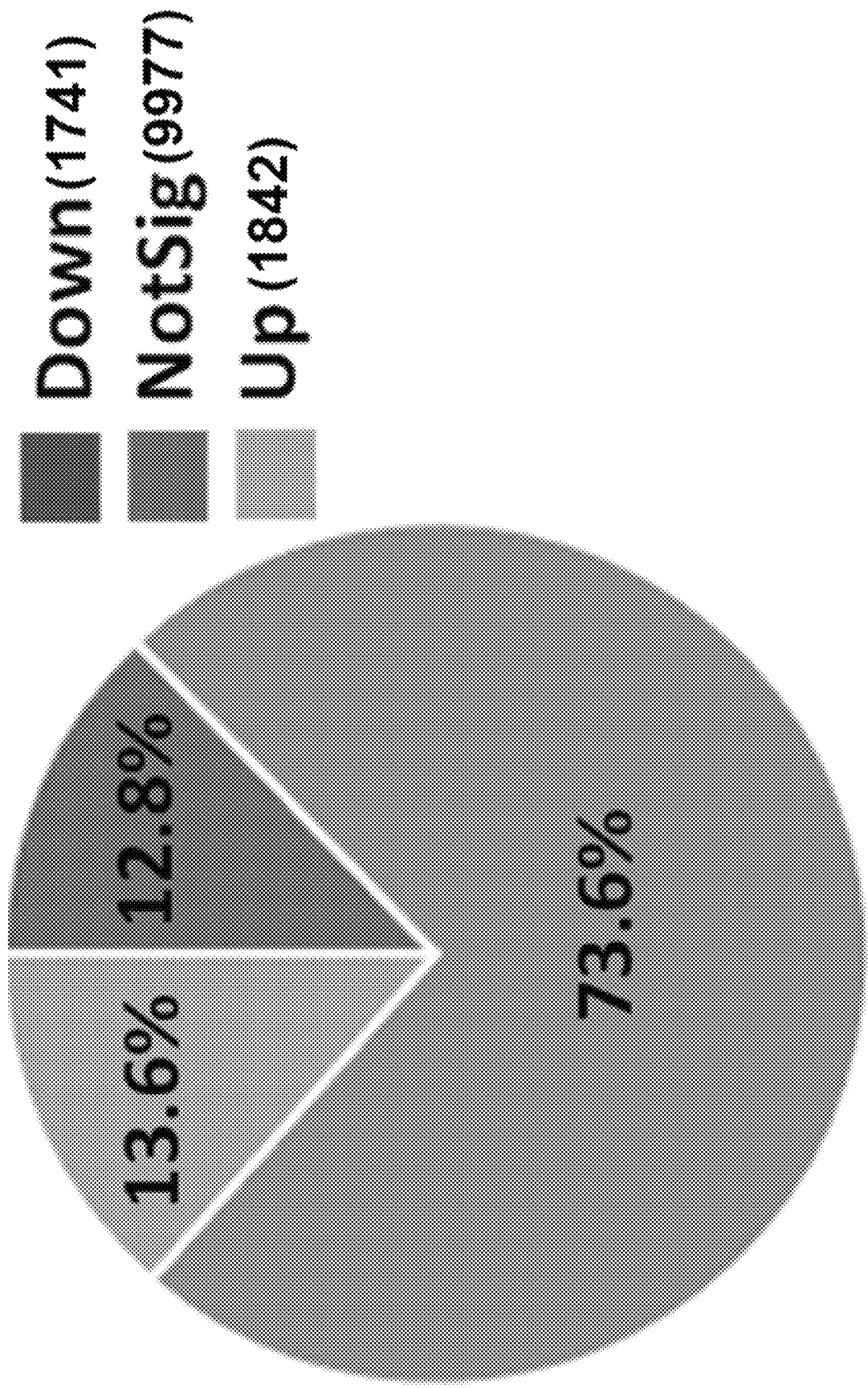
FIGS. 5A-5F show the effects of BRD9 inhibition in the transcriptome in uLMS cells.
Figure 5C:
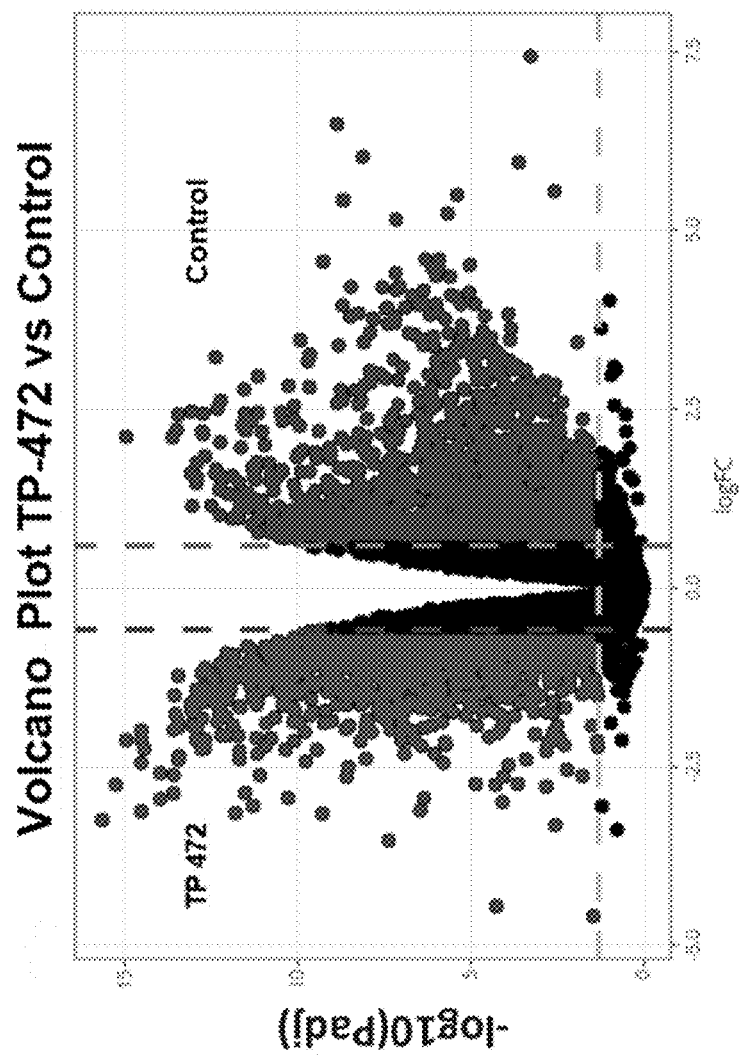
Figure 5B:
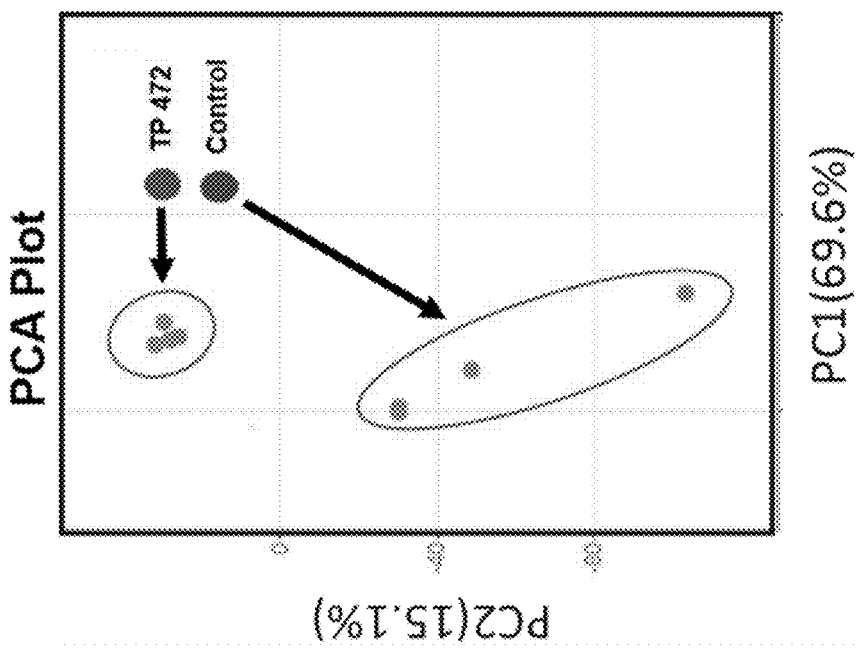
Figure 5D:
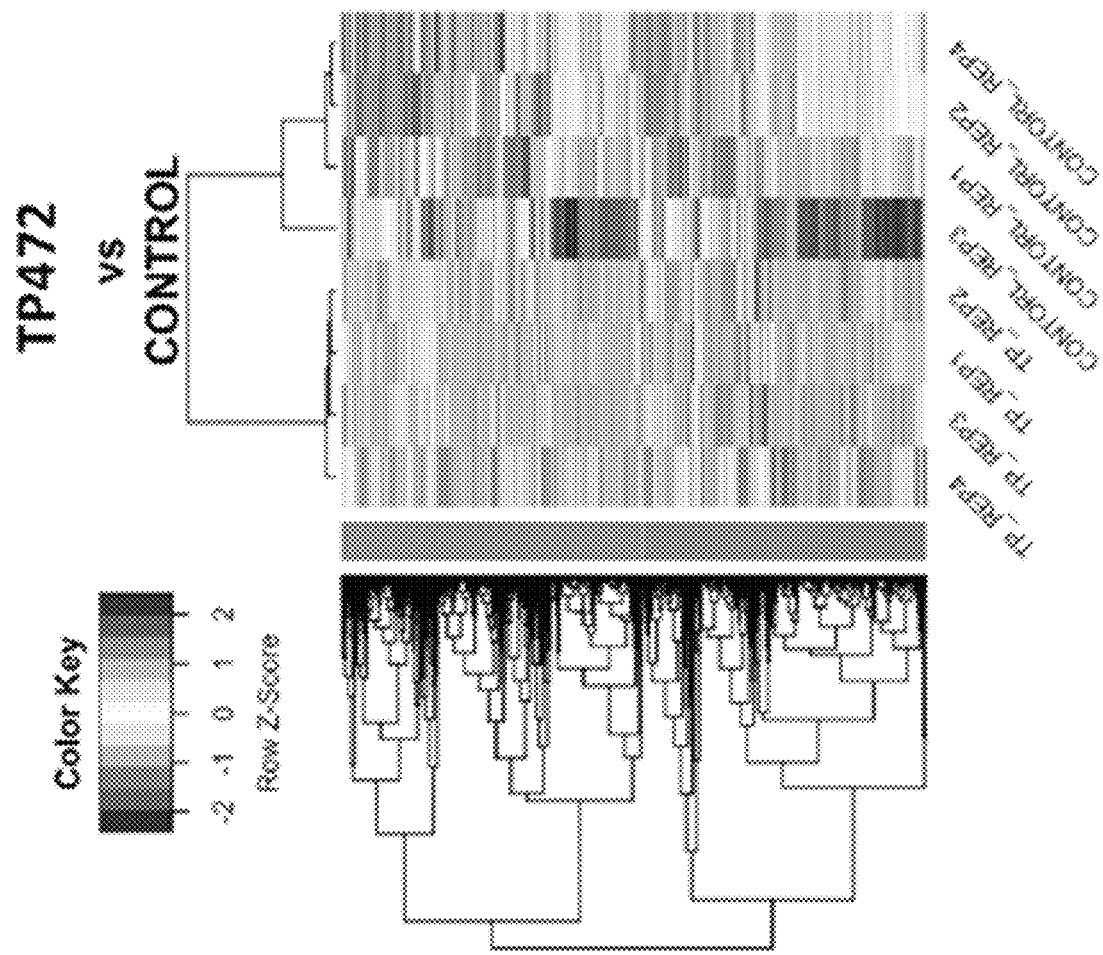
Figure 5E:
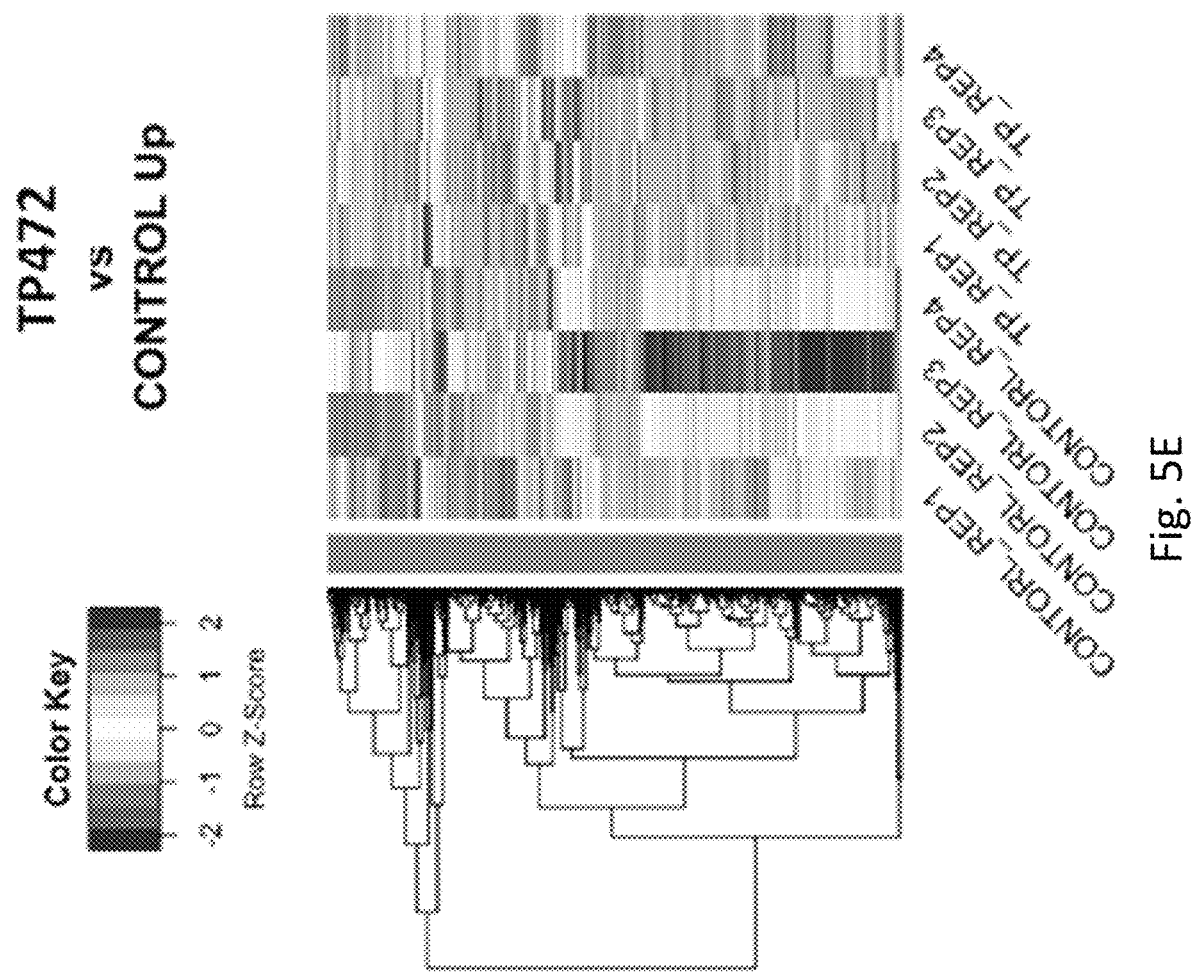
Figure 5F:
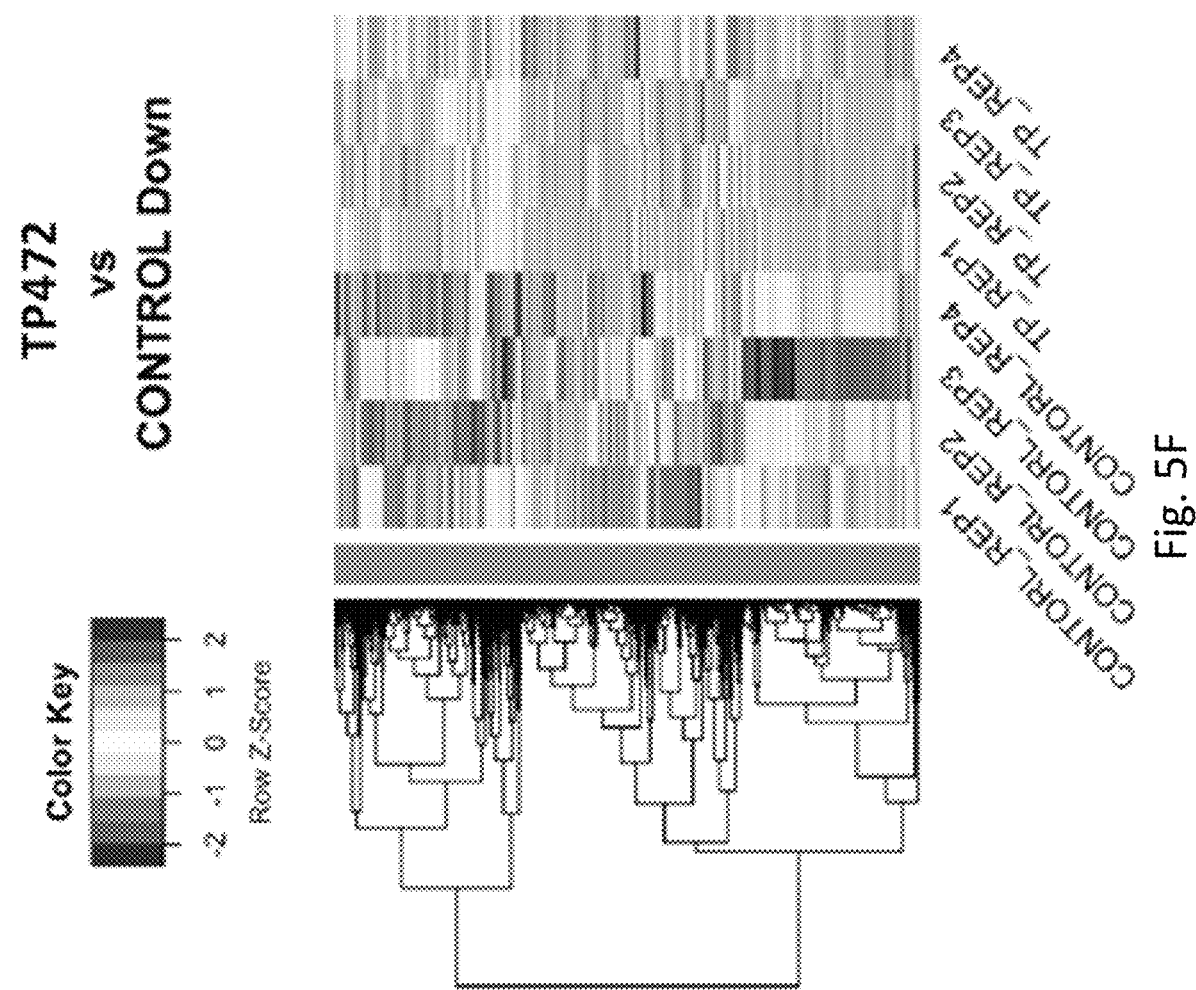
Figure 6A:
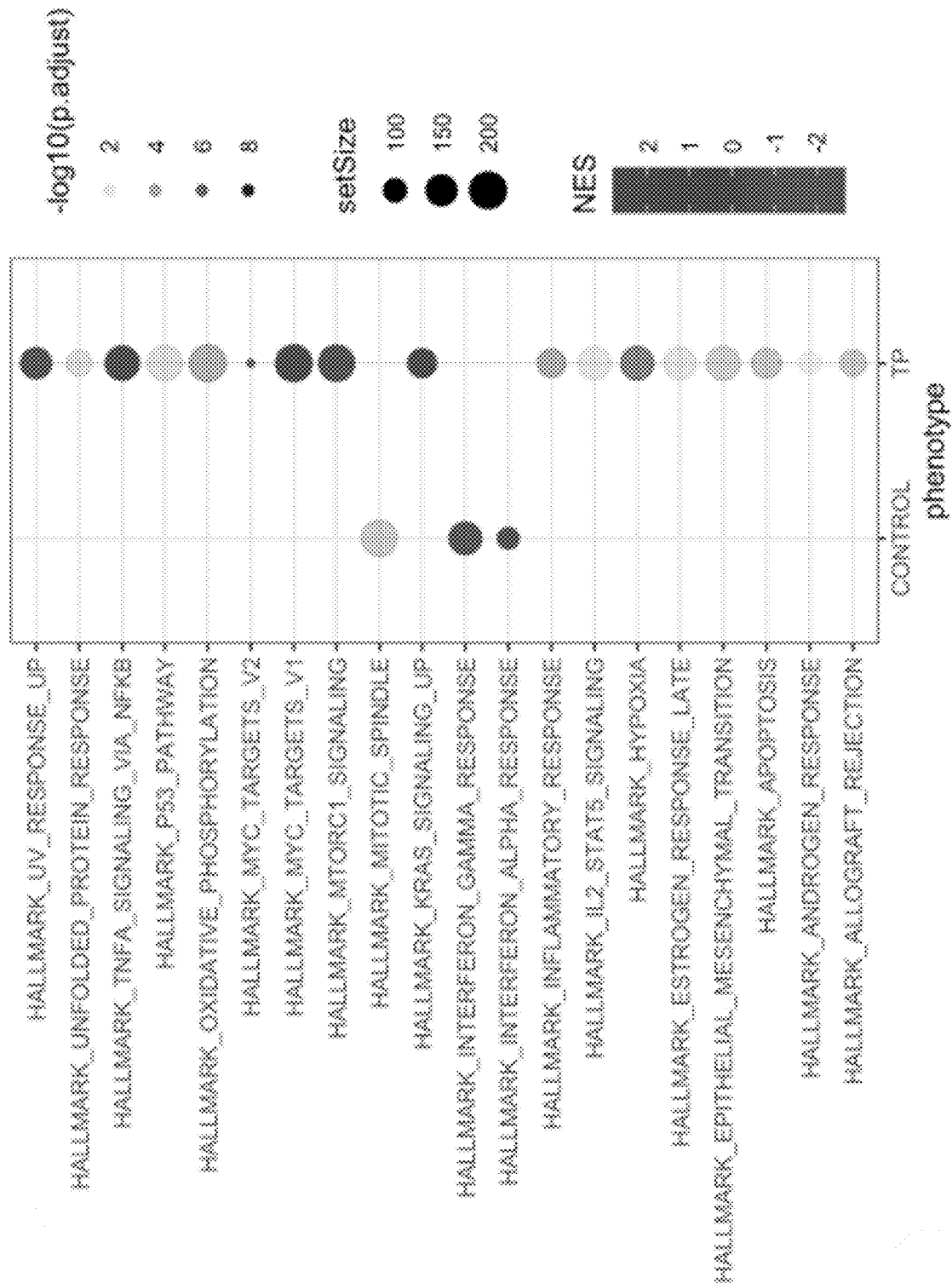
FIGS. 6A-6F show the effects of BRD9 inhibition in altering multiple pathways using hallmark analysis.
Figure 6B:
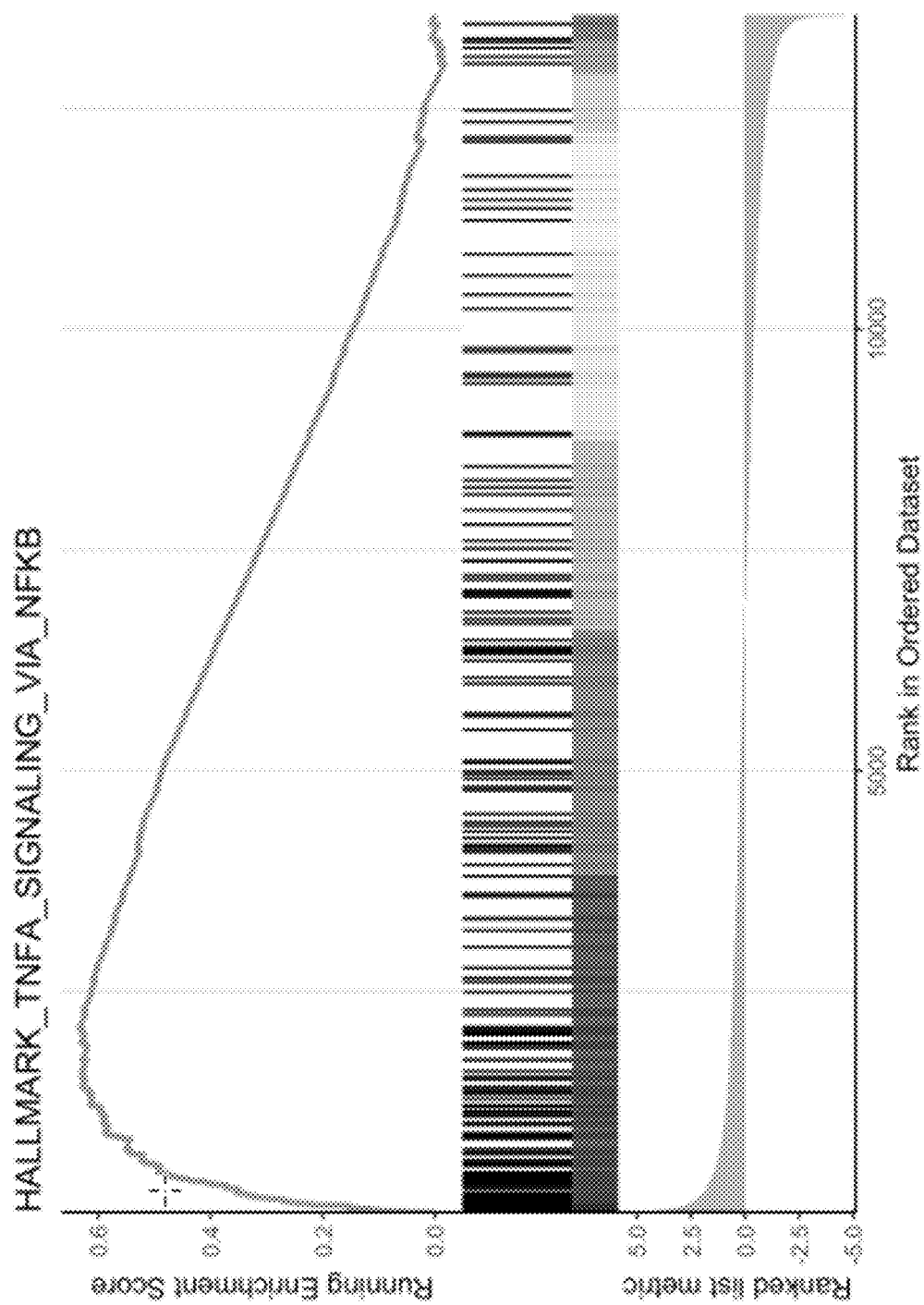
Figure 6C:
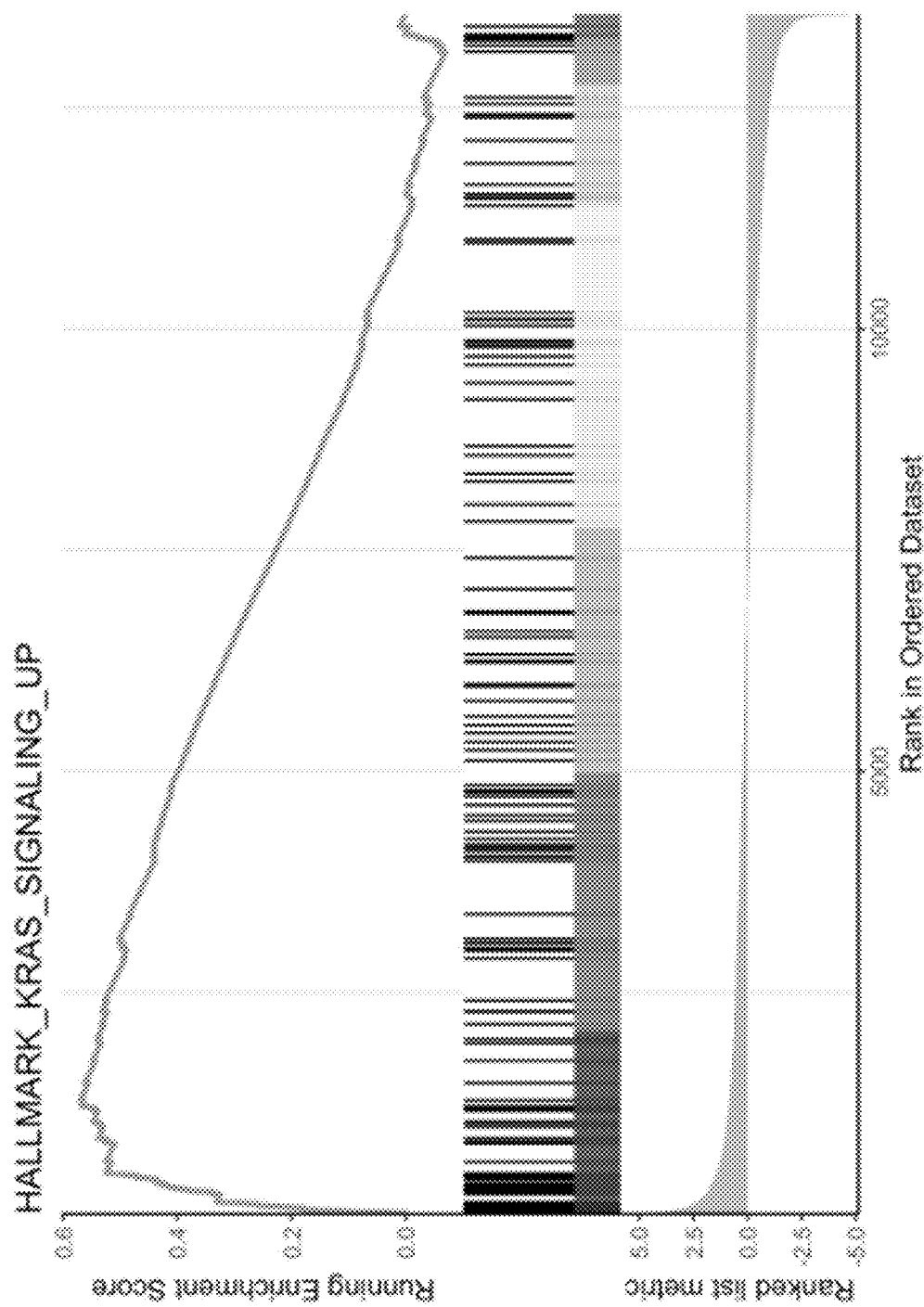
Figure 6D:
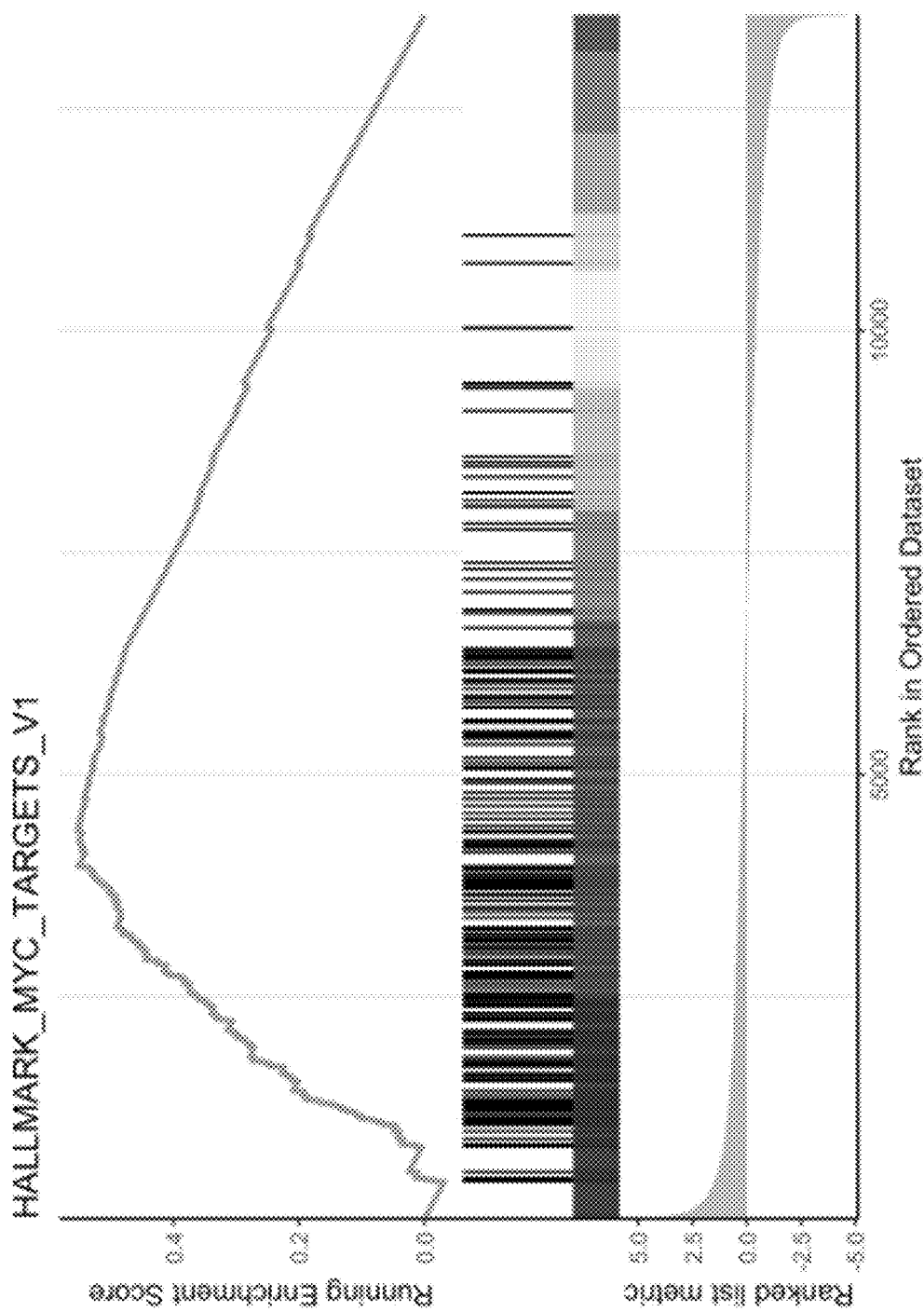
Figure 6E:
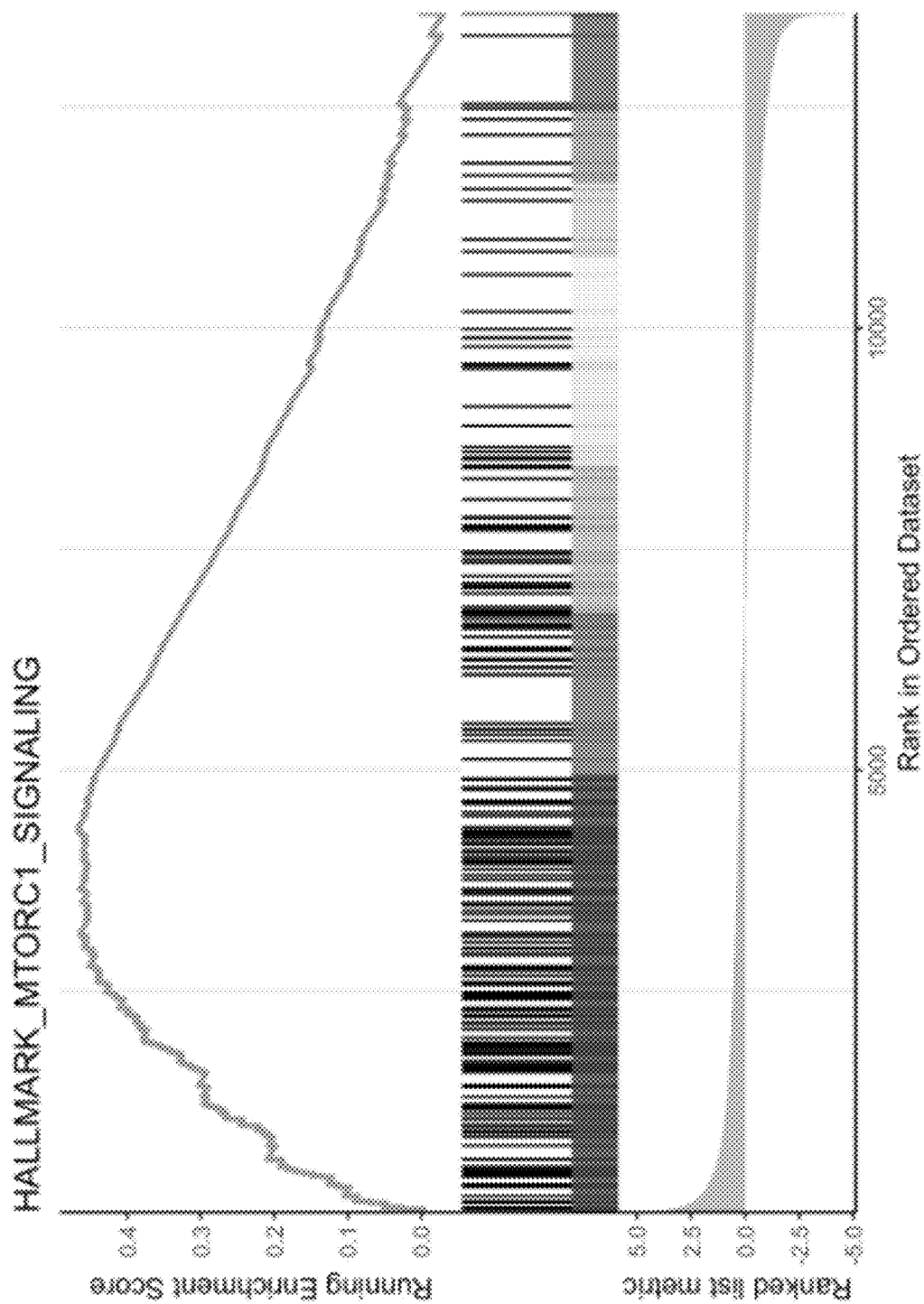
Figure 6F:
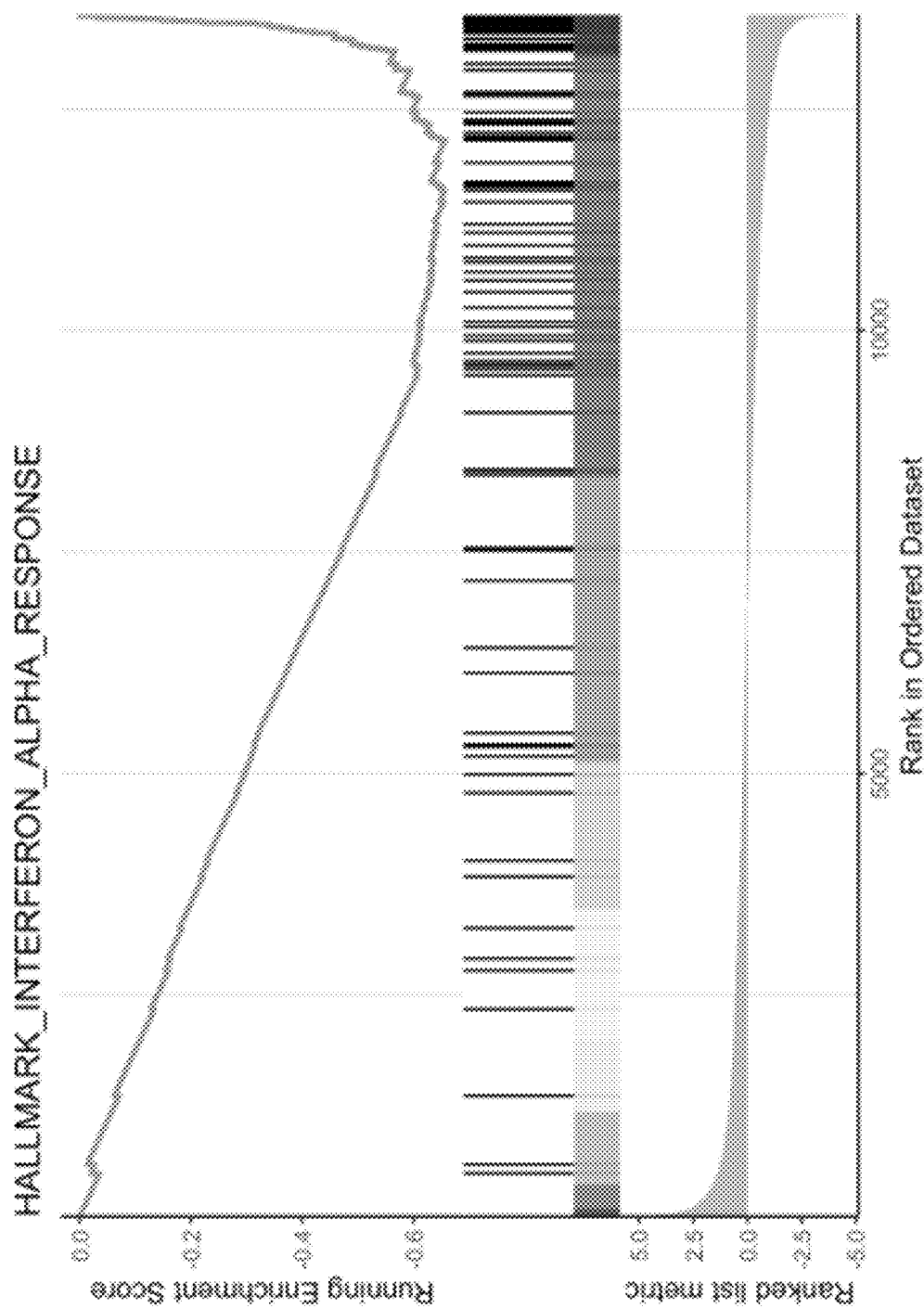

To determine the mechanistic action of TP-472 inhibition on uLMS cells, RNA-sequencing analysis was performed in control and TP-472 treated cells (n=4 each). As shown in FIG. 5A, TP-472 treatment yielded 3583 differentially expressed genes (DEGs) (1741 down, 1842 up). Principal component analysis (PCA) demonstrated that the expression pattern of the TP-472 group clustered separately from the control group (FIG. 5B). Volcano plot analysis revealed the distribution of pronounced changes in response to TP-472 treatment (FIG. 5C). Heatmap analysis further demonstrated a distinguished expression pattern in SK-UT-1 cells treated with TP-472 as compared to the control group (FIG. 5D-5F).

Pathway Analysis of DEGs upon TP-472 Treatment

Figures 7A, 7B:
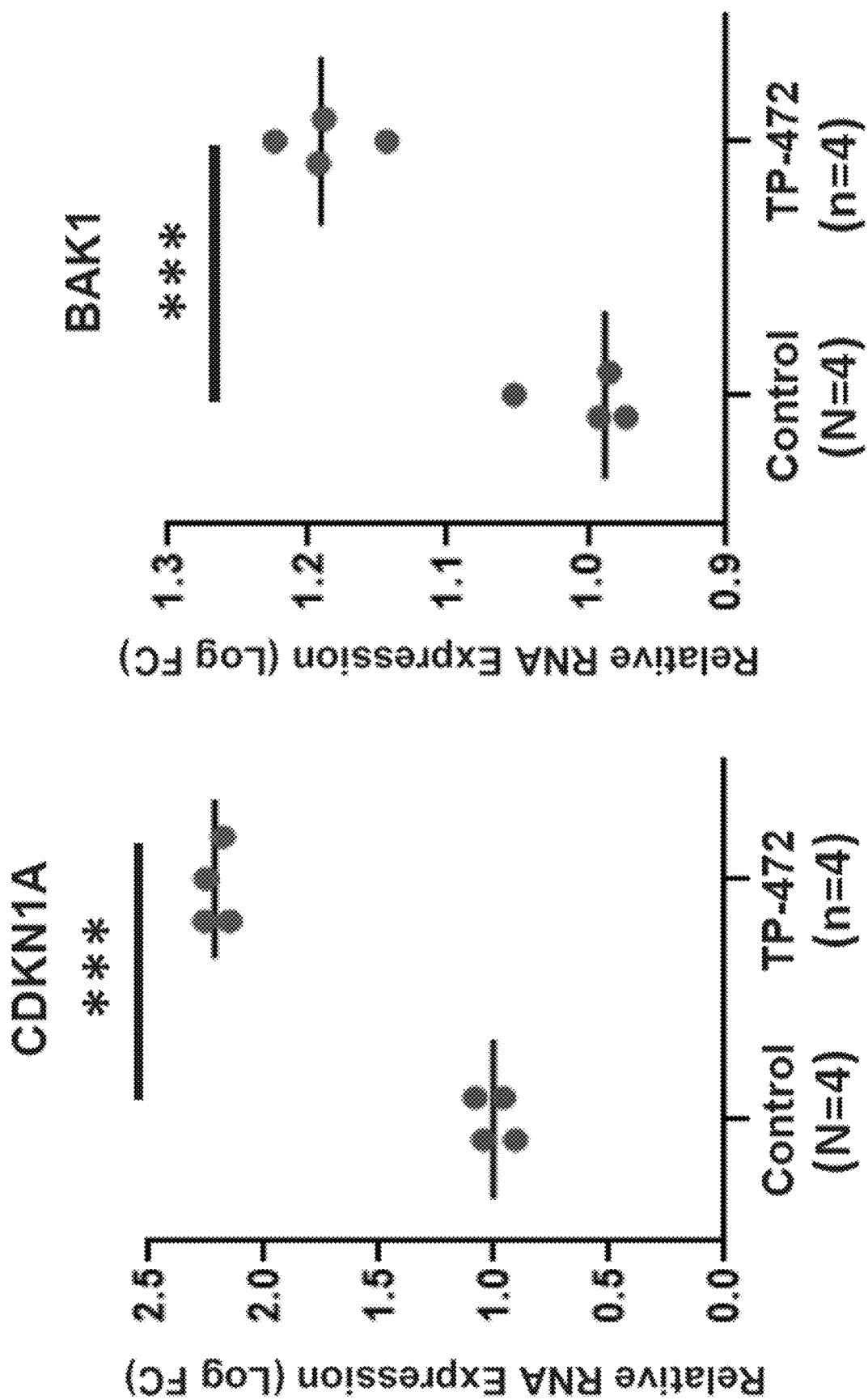
FIGS. 7A-7H are graphs showing relative RNA expression in TP-472 and control treated SK-UT-1 cells of CDKN1A (FIG. 7A), BAK1 (FIG. 7B), AKT1 (FIG. 7C), KT2 (FIG. 7D), Gill (FIG. 7E), GLI2 (FIG. 7F), P21 (FIG. 7G), and BAK (FIG. 7H).
Figure 7D:
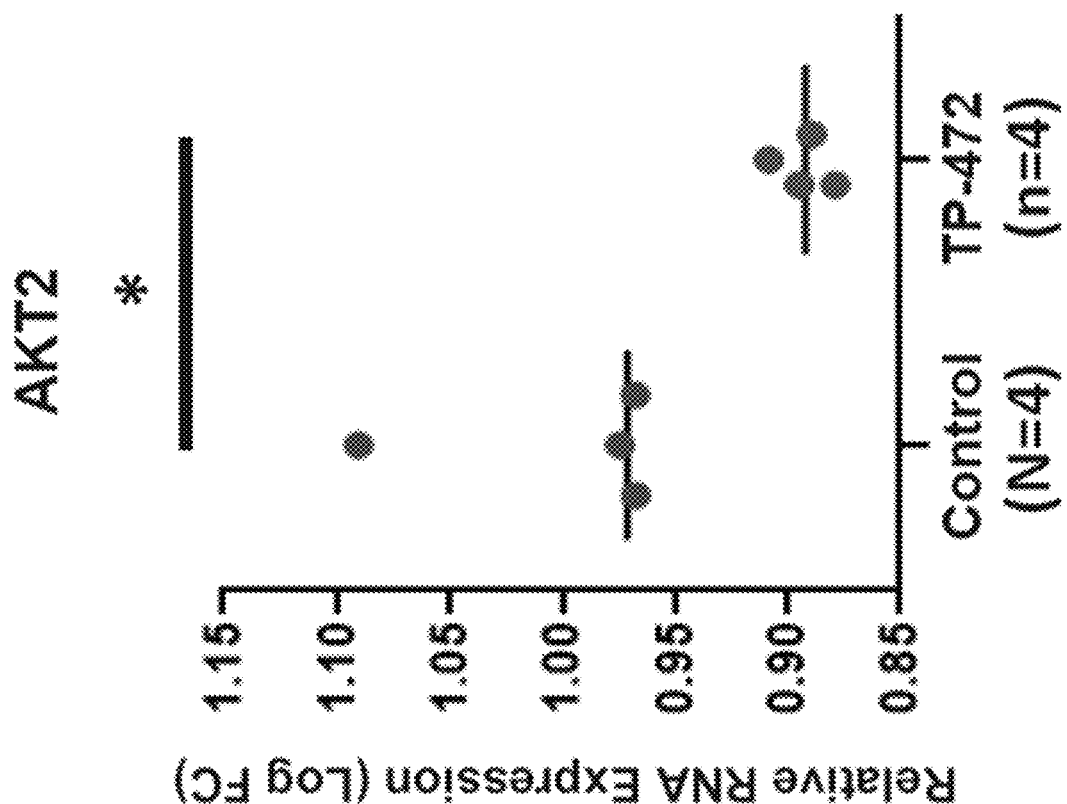
Figure 7C:
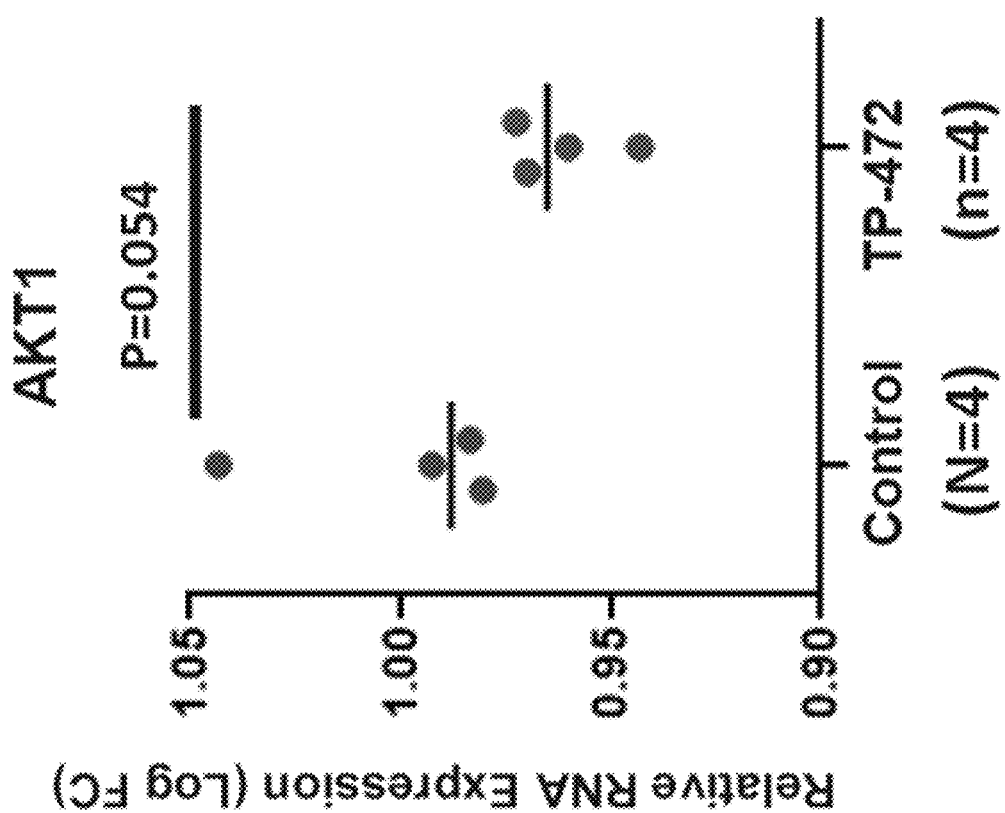
Figure 7F:
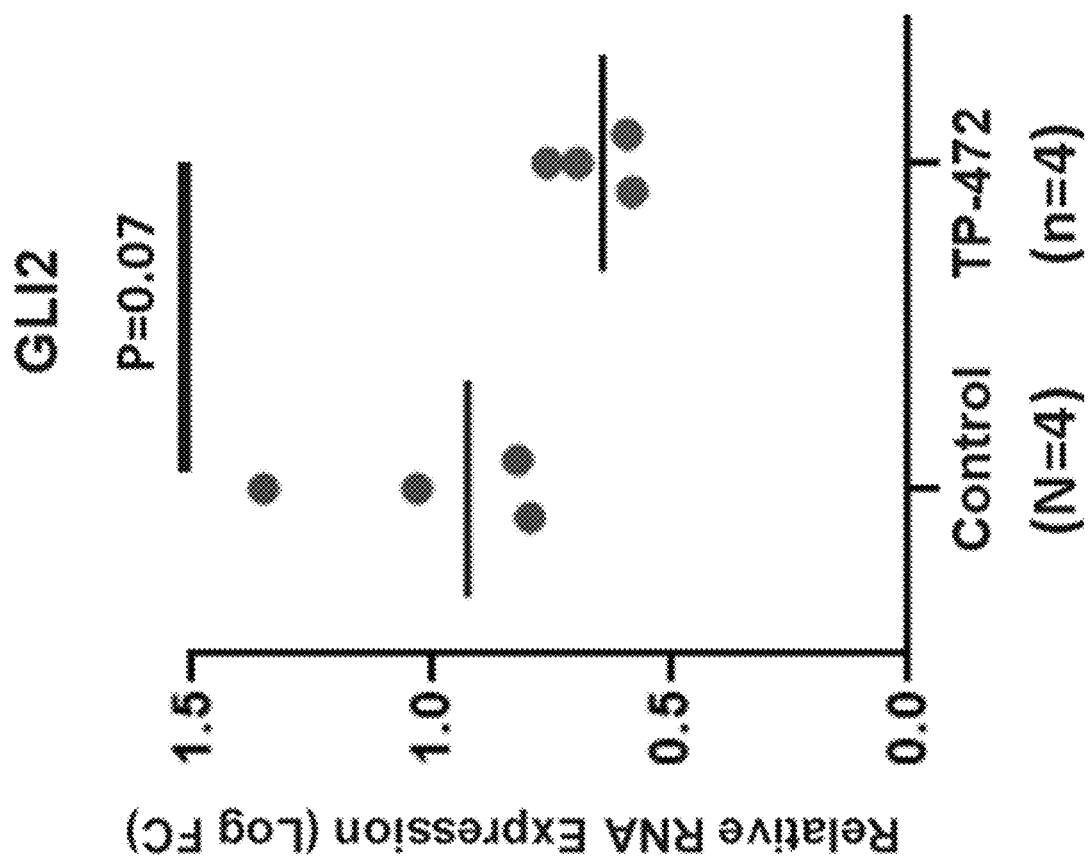
Figure 7E:
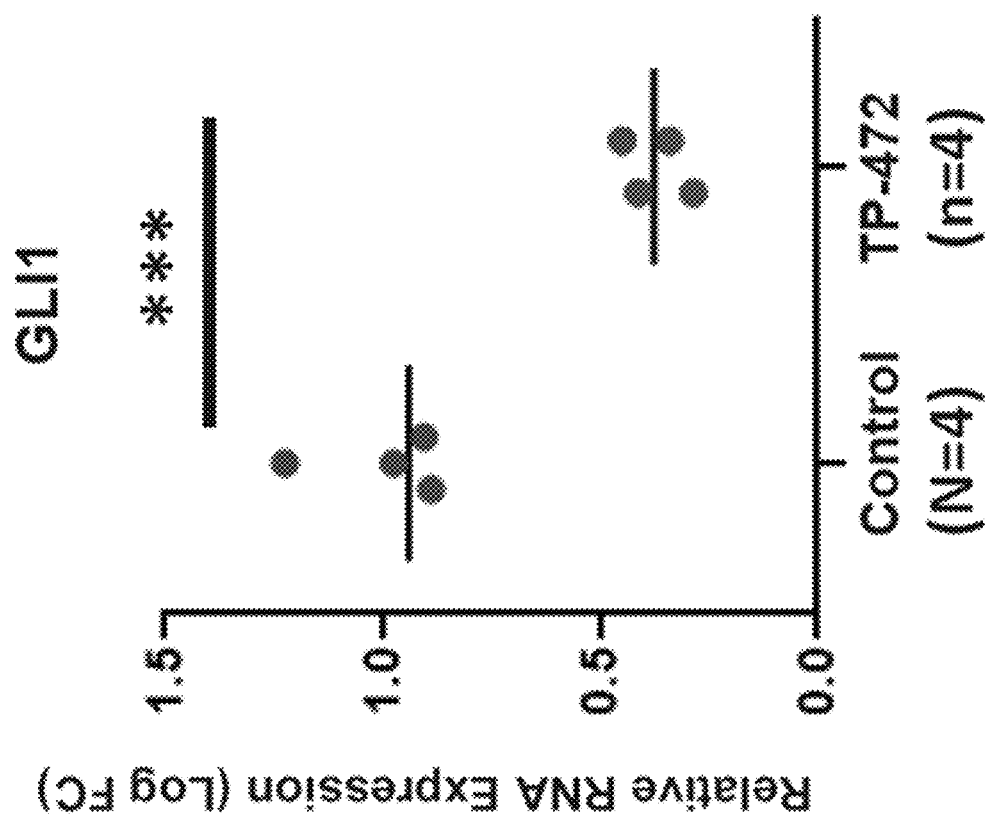

To gain insight into the biological changes induced by BRD9 inhibition globally, Hallmark pathway analysis was performed, which identified several pathways that were significantly altered, including interferon-alpha response, KRAS signaling, MYC targets, MTORC1 signaling, and TNF-a response (FIGS. 6A-6E). FIGS. 7A-7H show the expression of genes-related cell cycle and proliferation between control and TP-472-treated uLMS cells. Abnormally increased cell proliferation is one of the most notable characteristics of uLMS. P21 encoded by CDKN1A is a potent inhibitor of cell progression. As shown in FIG. 7A, CDKN1A expression is significantly higher in TP-472-treated uLMS cells compared to the control. In addition to cell cycle-related genes, the mRNA levels of BAK, the apoptosis regulator, were significantly increased in TP-472-treated SK-UT-1 cells compared to the control (FIG. 7B). AKT is at the crossroads of cell death and survival, playing a pivotal role in multiple interconnected cellular signaling mechanisms implicated in cell apoptosis and growth [35,36]. As shown in FIG. 7C, the expression of AKT1 was markedly decreased in TP-472-treated uLMS cells. The expression of AKT2 is also significantly decreased in TP-472-treated uLMS cells (FIG. 7D). Previous studies have demonstrated that the Hedgehog pathway is activated in uLMS. TP-472 significantly decreased the expression of Gill and markedly reduced the GLI2 expression in uLMS cells (FIGS. 7E-7F). These data suggest that TP-472 induced cell cycle arrest and apoptosis and inhibited Hedgehog pathway in uLMS cells.

Figure 7H:
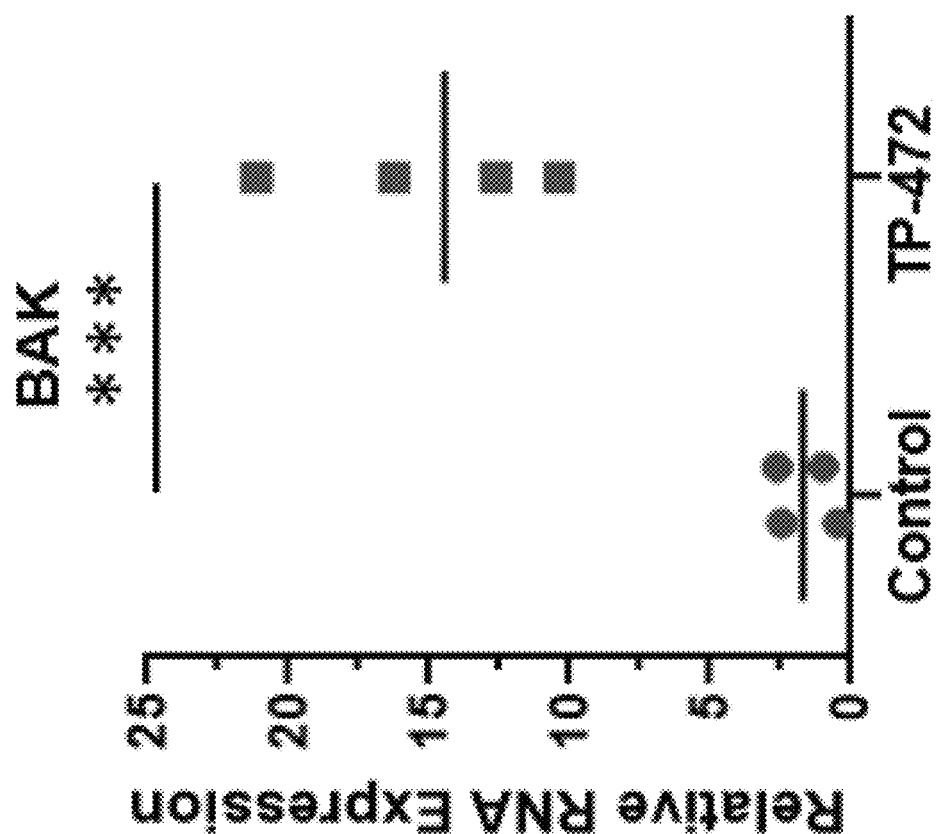
Figure 7G:
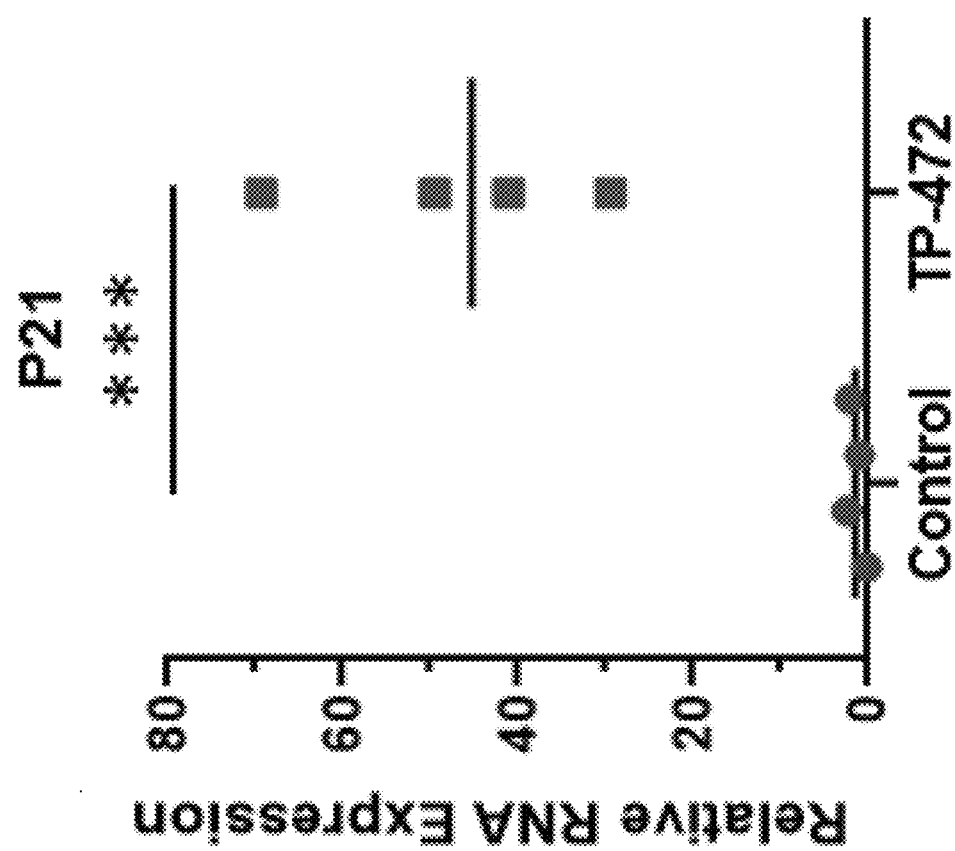

The expression of representative cell cycle- and apoptosis-related genes (CDKN1A and BAK) was also validated by q-PCR. As shown in FIGS. 7G-7H, the significant increase in expression of CDKN1A and BAK1 upon iBRD9 treatment was consistent with RNA-seq data.

Parsimonious Gene Correlation Network Analysis (PGCNA)

Figure 8A:
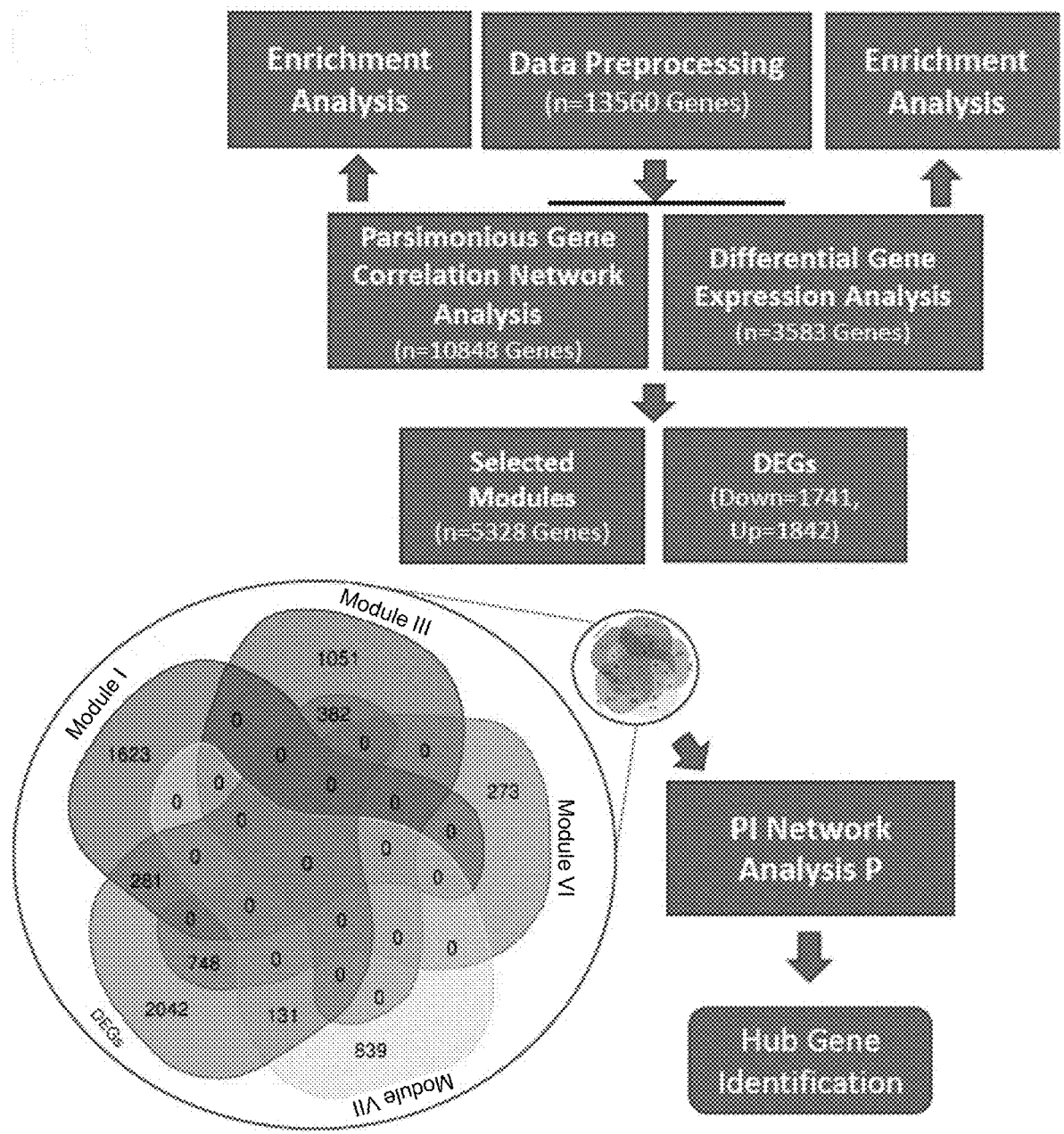
FIGS. 8A-8C show network representation of the modular pattern of gene expression during the transition of control to TP-472 treatment.
Figure 8B:
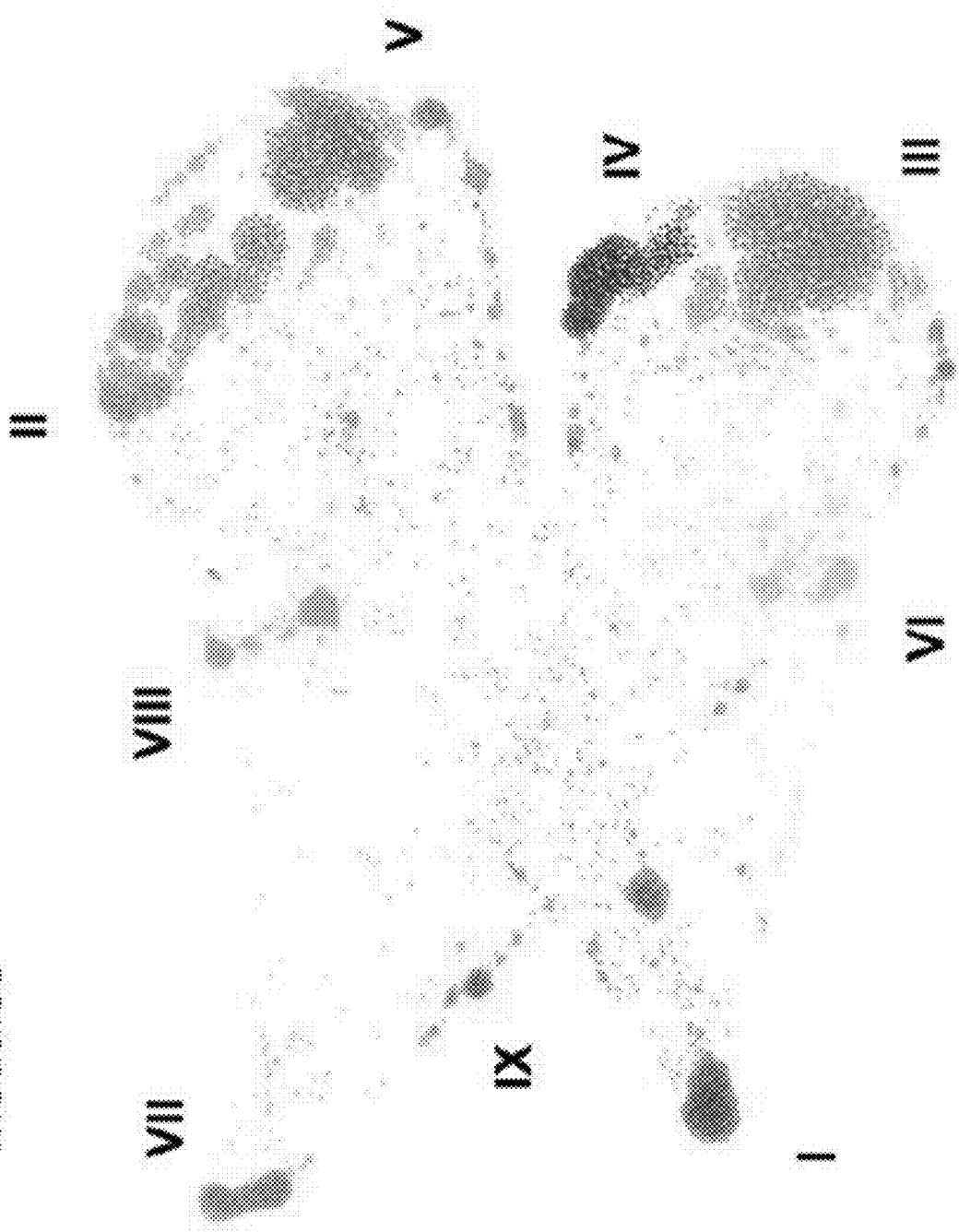
Figure 8C:
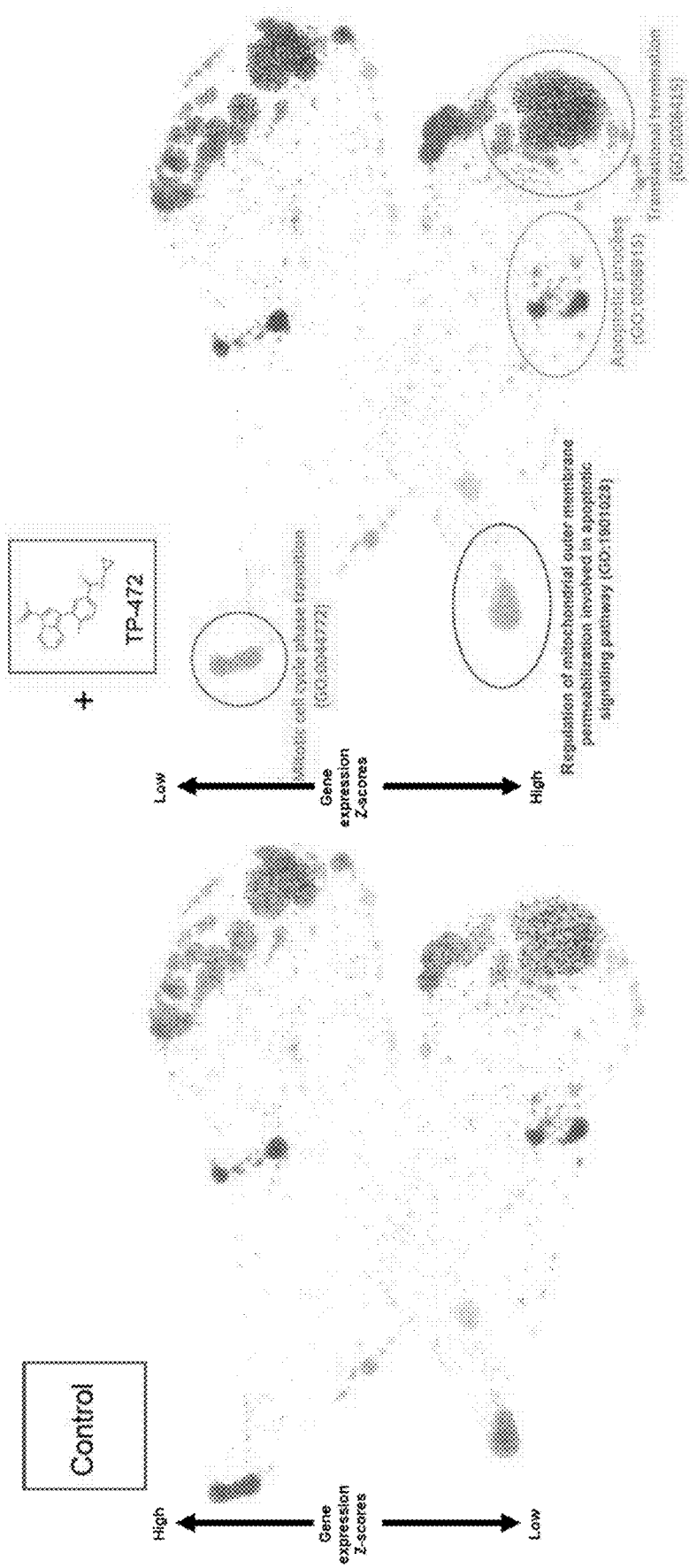

To identify a biologically meaningful gene module, PGCNA was performed. The pipeline of this example is shown in FIG. 8A. The co-expression network was constructed using the PGCNA2 package in Python software from the annotated genes, in which nine modules were identified (FIG. 8B). The enrichment results showed that modules I and VI were positively related to apoptosis; and modules III and VII were associated with the cell cycle (FIG. 8B). Therefore, subsequent enrichment analyses were performed to obtain further biological insight for the genes in the four constructed modules. The results for all four modules are shown in Table 6. From PGCNA analysis, apoptosis and cell cycle pathways were enriched upon TP-472 treatment. The top 40 hub genes (top 10 hub genes in each module) were screened out from the intersection of the Venn diagram between DEGs and four selected modules. The results are shown in Table 7. The intramodular connectivity of genes in the corresponding modules of interest was measured using the total number of edges linked to each gene, which is represented as the degree in Table 7. Notably, several Hub DEGs, including MYC, FOS, JUN, EGR1, SHH (sonic hedgehog pathway), GRIN1, SOX9, HRAS, IMP3, CDK, TOP2A, TOP2B, among others, are identified upon TP-472 treatment (Table 7).

histone modifications. Notably, DEGs induced by TP-472 treatment were significantly linked to the H4K27me3, while those suppressed by TP-472 treatment were preferentially associated with H3K4me1, H3K4me2, H3K4me3, and H3K27me3 according to the ENCODE Histone Modifications gene set library. The top 10 terms are shown in the lower panels of FIGS. 9A-9B. These studies suggest that TP-472 treatment may alter the uLMS cell transcriptome via epigenetic mechanisms.

Inhibition of BRD9 Altered Gene Expression Correlating to miRNA Regulation

TargetScan microRNA analysis in Enrichr was used to determine the mechanism underlying the regulation of DEG via miRNA in response to TP-472 treatment. As shown in Table 8, genes induced by TP-472 treatment (up) correlated with miRNAs, including hsa-miR-4776-5p, hsa-miR-671-3p, hsa-miR-3619-3p, hsa-miR-621, hsa-miR-553, among others. By contrast, genes suppressed by TP-472 treatment (down) correlated with a distinct set of miRNAs, including hsa-miR-542-5p, hsa-miR-4734, hsa-miR-3682-3p, and hsa-miR-4727-3p among others, suggesting that miRNAs may be involved in regulating gene expression in response to TP-472 treatment.

TABLE 6

The significant terms of the modules based on the 9 different enrichment databases

| Module | Module I | Module VI | Module III | Module VII |
|---|---|---|---|---|
| GO_Biological_Process_2021 | regulation of mitochondrial outer membrane permeabilization involved in apoptotic signaling pathway (GO:1901028) (1.38E-05) | Apoptotic process (GO:0006915) (2.00E-05) | translational termination (GO:0006415) (8.54E-31) | mitotic cell cycle phase transition (GO:0044772) (3.36E-07) |
| MSigDB_Hallmark_2020 | TNF-alpha Signaling via NF-kB (0.000138704) | TNF-alpha Signaling via NF-kB (1.08E-16) | Myc Targets V1 (1.25E-39) | PI3K/AKT/mTOR Signaling (0.031214077) |
| WikiPathway_2021 | MAPK Signaling Pathway WP382 (0.001957412) | Sudden Infant Death Syndrome (SIDS) Susceptibility Pathways WP706 | G1 to S cell cycle control WP45 (0.037948453) | Cell cycle WP179 (1.90E-05) |
| Reactome_2015 | TRAF6 mediated induction of NFkB and MAP kinases upon TLR7/8 or 9 activation Homo sapiens R-HSA-975138 (0.093688577) | MAPK family signaling cascades Homo sapiens R-HSA-5683057 (0.019875184) | Cyclin E associated events during G1/S transition Homo sapiens R-HSA-69202 (9.09E-10) | Cell Cycle Homo sapiens R-HSA-1640170 (3.50E-11) |
| ENCODE_Histone_Modifications_2015 | H3K4me1 (2.98E-15) | H3K27me3 (4.96E-48) | H3K4me3 (5.19E-10) | H3K4me3 (1.91E-06) |
| TargetScan_microRNA_2017 | hsa-miR-4776-5p MicroRNAs (0.001954789) | hsa-miR-4727-3p (0.001242581) | hsa-miR-1284 (0.021500132) | hsa-miR-3682-3p MicroRNAs (5.49E-14) |
| InterPro_Domains_2019 | NFkappaB IPT domain (0.007433747) | Death domain (0.001693697) | LSM domain (1.28E-09) | Protein kinase domain (4.49E-05) |
| Pfam_Domains_2019 | Pkinase (0.000212328) | Death (0.000791274) | LSM (5.50E-10) | Pkinase (3.62E-05) |
| Jensen_COMPARTMENTS | Neuron part (5.89E-07) | BCL-2 complex (3.34E-08) | Intracellular ribonucleoprotein complex (5.21E-49) | cellular component (5.48E-22) |

TABLE 7

The top 40 hub genes shared between DEGs and four selected modules

| Genes | Modules | FC | Degree | Genes | Modules | FC | Degree |
|---|---|---|---|---|---|---|---|
| MYC | I | 1.56 | 165 | CCT2 | III | 1.61 | 160 |
| FOS | I | 1.50 | 81 | NOP56 | III | 1.64 | 154 |
| SHH | I | 4.66 | 70 | NOP58 | III | 1.74 | 149 |
| GRIN1 | I | 2.54 | 56 | NIP7 | III | 1.92 | 141 |
| SOX9 | I | 2.02 | 55 | PA2G4 | III | 1.55 | 139 |
| TERT | I | 1.68 | 47 | HSPA8 | III | 1.75 | 139 |
| STX1A | I | 1.78 | 45 | IMP3 | III | 1.62 | 136 |
| CEBPB | I | 1.75 | 44 | EIF2S1 | III | 1.52 | 124 |
| EGR1 | I | 1.63 | 42 | RPL26L1 | III | 1.58 | 118 |
| GATA2 | I | 2.26 | 39 | CYCS | III | 1.86 | 117 |
| JUN | VI | 3.13 | 93 | CDK1 | VII | -1.56 | 91 |
| FN1 | VI | 2.40 | 87 | TOP2A | VII | -1.52 | 71 |
| HRAS | VI | 1.60 | 80 | CHEK2 | VII | -1.69 | 61 |
| CCND1 | VI | 2.21 | 68 | WDHD1 | VII | -1.52 | 56 |
| MRTO4 | VI | 2.16 | 53 | TOP2B | VII | -1.52 | 39 |
| KIT | VI | 20.37 | 53 | STAG2 | VII | -1.51 | 34 |
| BYSL | VI | 1.75 | 49 | MIS18BP1 | VII | -1.53 | 28 |
| RRP9 | VI | 2.71 | 49 | HLTF | VII | -1.78 | 25 |
| PDCD11 | VI | 1.69 | 49 | FGF2 | VII | -1.56 | 25 |
| LEF1 | VI | 6.22 | 49 | TIA1 | VII | -1.60 | 17 |

Inhibition of BRD9 Altered the Gene Expression Correlating to Histone Modifications To investigate whether TP-472 treatment led to transcriptional changes via epigenomic effects in uLMS cells, enrichment analysis of epigenetic histone markers was performed using the Enrichr web server. As shown in FIGS. 9A-9B, DEGs between control and TP-472 were correlated with

TABLE 8

Down and Up DEGs induced by TP-472 treatment

| Down DEGs | | UP DEGs | |
|---|---|---|---|
| Name | P-value | Name | P-value |
| hsa-miR-542-5p | 0.0003401 | hsa-miR-4776-5p | 1.53E-07 |
| hsa-miR-4734 | 0.001135 | hsa-miR-671-3p | 0.0002854 |

TABLE 8-continued

Down and Up DEGs induced by TP-472 treatment

| Down DEGs | | UP DEGs | |
|---|---|---|---|
| Name | P-value | Name | P-value |
| hsa-miR-3682-3p | 0.0004695 | hsa-miR-3619-3p | 0.000007943 |
| hsa-miR-4727-3p | 0.001155 | hsa-miR-621 | 0.00002329 |
| hsa-miR-517b | 0.006743 | hsa-miR-553 | 0.0001665 |
| hsa-miR-492 | 0.001802 | hsa-miR-628-3p | 0.0001713 |
| hsa-miR-192 | 0.002299 | hsa-miR-550b | 0.0003165 |
| hsa-miR-215 | 0.002299 | hsa-miR-4535 | 0.0006112 |
| hsa-miR-718 | 0.01137 | hsa-miR-4529-3p | 0.0004322 |
| hsa-miR-3186-3p | 0.01918 | hsa-miR-210 | 0.002306 |
| hsa-miR-1296 | 0.005603 | hsa-miR-3684 | 0.001141 |
| hsa-miR-4479 | 0.02042 | hsa-miR-502-3p | 0.0006386 |
| hsa-miR-3177-3p | 0.0127 | hsa-miR-501-3p | 0.0006386 |
| hsa-miR-1973 | 0.01666 | hsa-miR-409-5p | 0.00104 |
| hsa-miR-196a | 0.009599 | hsa-miR-556-5p | 0.0007066 |
| hsa-miR-196b | 0.009599 | hsa-miR-3152-3p | 0.0007233 |
| hsa-miR-3141 | 0.01549 | hsa-miR-508-3p | 0.001113 |
| hsa-miR-517c | 0.03087 | hsa-miR-4759 | 0.001333 |
| hsa-miR-517a | 0.03087 | hsa-miR-3613-5p | 0.00253 |

DISCUSSION

Understanding the relationship between the epigenetic regulators and tumorigenesis is important for the manipulation of chromatin regulation in cancer therapy. The present example has revealed that BRD9, as the readers of lysine acetylation for regulating the protein-histone association and chromatin remodeling, were upregulated in uLMS tissues and cells. Inhibition of BRD9 increased cell death, induced cell cycle arrest, altered several other important biological pathways, and reprogrammed the onco-epigenome in uLMS cells, suggesting the important role of BRD9 in the pathogenesis of uLMS.

The association and functional studies on BRDs in cancer biology have been investigated in several types of cancer. For example, BRD specifies the control mixed lineage leukemia phenotype. BRDs played a role in regulating important genes from chromatin and were associated with MLL fusion oncoproteins in leukemogenesis. BRD2 is important for proinflammatory cytokine production in macrophages. BRD2 and BRD4 physically associate with the promoters of inflammatory cytokine genes in macrophages. BRD inhibition by JQ1 can block this association and reduce the IL-6 and TNF-levels. These studies suggested that targeting the BET proteins will benefit hyperinflammatory conditions associated with high levels of cytokine production. In ovarian cancer, JQ1 suppresses tumor growth associated with cell cycle arrest, apoptosis induction, and metabolic alterations. In Ewing Sarcoma, coimmunoprecipitation revealed an interaction of BRD4 with CDK9. Combined treatment of Ewing Sarcoma with BRD- and CDK9-inhibitors resulted in enhanced responses compared to individual drugs not only in vitro but also in a preclinical mouse model in vivo. A recent study reported that BETi GS-626510 (10 mg/kg twice a day treatment for 13 days) significantly decreased the in vivo uLMS growth compared to vehicle control. In addition to the Bromo- and extra-terminal domain (BET) family, the role of the non-BET family has been investigated recently. For instance, non-BET family inhibitor NVS-CECR2-1 inhibits chromatin binding of CECR2 BRD and displaces CECR2 from chromatin within cells. NVS-CECR2-1 exhibits cytotoxic activity against various human cancer cells, killing SW48 colon cancer cells by inducing apoptosis. In melanoma, the iBRD9 (TP-472) blocked tumor growth by sup-pressing ECM-mediated oncogenic signaling and inducing apoptosis. In renal clear cell carcinoma, the combined analysis of BRD9 and other chromatin regulated genes showed a significant association with the high-risk groups and lower overall survival, providing a survival prediction model for further research investigating the role of the expression of BRD genes in cancers.

uLMS is a rare but extremely aggressive tumor characterized by therapy resistance. Consequently, uLMS patients commonly present high rates of tumor recurrence, progression and metastasis. While the malignant potential of uterine fibroids is extremely low, the possibility of transforming of UFs to uLMS has been proposed. Therefore, other mechanisms should play an important role in the development and progression of this aggressive cancer. In this example, it was demonstrated that expression levels of non-BET family member BRD9 are aberrantly upregulated in uLMS compared to adjacent myometrial tissues and higher in uLMS cells as compared to benign UF cells, indicating the important role of BRD9 protein in the pathogenesis and progression of this cancer.

The development and use of small chemical inhibitors are important to the preclinical evaluation of BRDs as targets. Recently, a non-BET inhibitor, TP-472, has been developed with high potency for BRD9. In this example, the impact of TP-472 on uLMS cells aberrantly overexpressing BRD9 was demonstrated showing that TP-472 significantly inhibited uLMS proliferation concomitantly with a dose dependent decrease in BCL-2 expression. This example is consistent with the previous observation that iBRDs induced apoptosis by activating the expression of several pro-apoptotic genes in melanoma and MLL-fusion leukemia cells.

To further determine the mechanistic action of BRD9 inhibition, comparative transcriptome-wide RNA-sequencing was performed in uLMS cells treated with vehicle or TP-472. Previously, transcriptome-wide mRNA profiling in melanoma cells demonstrated TP-472 not only upregulated pro-apoptotic genes such as BAX, CDKN1A, GADD45A, GAD45B, among others, associated with the p53 pathway, but also downregulated several extra-cellular matrix proteins, which are important for tumor growth. This example's transcriptomic profiling analysis in uLMS revealed that multiple pathways were altered in response to TP-472 treatment. For instance, signatures enriched in uLMS cells, including MYC targets, interferon-alpha/gamma, K-ras, TNF signaling via NFkB, and MTORC1 signaling were observed between TP-472 and the control group. These newly identified pathways in uLMS in response to TP-472 treatment suggest that TP-472 targets common pathways and oncogenic transcriptome networks based on different types of cancer cells. Notably, using the PGCNA approach, nine modules affected by iBRD9 were identified. In this example, cell cycle and apoptosis modules that correlated with uLMS phenotype changes induced by iBRD9 were identified for further investigation. The expression of genes belonging to these two models was significantly altered. In addition, the expression of cell cycle and apoptosis-related genes was validated and further demonstrated that TP-472 treatment increased the expression levels of the cell cycle arrest- and apoptosis-related genes, suggesting that TP-472 suppressed the uLMS growth via induction of both apoptosis and cell cycle arrest. Several Hub DEGs, including MYC, FOS, JUN, EGR1, SHH, GRIN', SOX9, HRAS, IMP3, CDK1, TOP2A, TOP2B, among others, are identified upon iBRD9 treatment. MYC is known to cooperate with KRAS in driving many cancers and contributes to many cancer hallmarks. The MYC gene is a proto-oncogene and encodes a nuclear phosphoprotein that plays a role in cell cycle progression, apoptosis, and cellular transformation. The expression changes of MYC as identified in the Hub DEGs are consistent with Hallmark pathway analysis, showing the MYC pathway is enriched in response to TP-472 treatment, indicating the important role of the MYC hub and related network in the pathogenesis of uLMS. This example shows the compensatory induction of MYC RNA expression and HRAS by iBRD9. Simultaneously inhibiting BRD9 and MYC may efficiently induce growth arrest and apoptosis of uLMS cells, suggesting the potential of a combination treatment strategy.

The jun and fos families are involved in the regulation of cell proliferation, differentiation, and transformation. Fos can dimerize with proteins of the jun family, thereby forming the transcription factor complex AP1 and enhancing the transcriptional activity. The AP1 complex can interact with bZIP proteins and structurally unrelated transcription factors. This cooperative recruitment of transcription factors, coactivators and chromatin remodeling factors to promoter and enhancer regions mediates the selective regulation of transcription activity. In this example, the fos and jun expression was increased in iBRD9-treated uLMS cells. Previous studies demonstrated a discrepancy between jun/fos proto-oncogene mRNA and protein expression in other diseases. EGR1 as an additional transcriptional regulator in Hub DEGs plays an important role in regulating the transformation, cell survival, proliferation, and cell death. In this example, TP472 increased the expression of EGR1 in uLMS, providing a mechanism of TP-472 induced inhibition of cell proliferation. Notably, the role of EGR1 in tumor formation is controversial in diseases and conditions. For example, EGR1 functions as a tumor suppressor by monitoring DNA damage, promoting cell apoptosis, and enhancing the anticancer effects of radiotherapy and chemotherapy. EGR1 can activate the expression of p53/TP53, and thereby helps prevent tumor formation. However, in certain circumstance such as hypoxic microenvironments, the increase in EGR1 expression maintains tumor cell survival, proliferation, metastasis, and tumor angiogenesis. SOX9 (hub DEG) as a transcriptional factor is also identified in this example.

Several transcription factors of BRD9 have recently been identified. Notably, the master transcription factor Sox 17 recruits BRD to a subset of enhancers associated with genes involved in the cell cycle and angiogenesis, among others. In this regard, BRD9 acts as a molecular bridge between the subset of enhancers and the transcription machinery. This suggests a deep understanding of the role and functional mechanism of BRD9 transcription factors will increase understanding of the pathogenesis of malignant uLMS.

Notably, the SHH pathway is observed in this example as the Hub pathway in response to TP-472 treatment. It has previously been shown that the Hedgehog pathway played an important role in uLMS pathogenesis via GLI molecules. In this example, the inhibition of BRD9 was shown to downregulate the expression of GLI1/2, the important components in the Hedgehog pathway, indicating the interplay between BRD9 and the Hedgehog pathway implicated in the uLMS pathogenesis. HRAS plays an important role in cell division, the process by which cells mature to carry out specific functions (cell differentiation), and the self-destruction of cells (apoptosis). It has been shown that TP-472 treatment leads to upregulation of GADD45A, the pro-apoptosis gene in melanoma cells. GADD45A has a direct role in p38 activation by HRAS. Another important component for HRAS growth arrest is GADD45A, which is known to be regulated by p53. Interestingly, the expression level of HRAS was increased in TP-472-treated uLMS cells suggesting that HRAS might cause apoptosis in TP-472-treated uLMS cells via GADD45A.

It has been reported that pathways involved in the regulation of cell cycle and apoptosis were most significantly enriched in direct targets of IMP3 at transcriptome and translatome levels, respectively. IMP3 silencing downregulated several well-known apoptosis regulators such as BIRC5, RAF1, and ESPL1. Overexpression of IMP3 in TP-472-treated uLMS cells suggests that IMP3 plays a significant role in the uLMS pathogenesis.

The role of CDK1 in gynecological cancer is limited to ovarian and endometrial cancer. The inhibition of CDK1 activity induced cell apoptosis and caused the G2/M phase arrest of cell cycle in endometrial cancer cells. It has been shown that CDK1 inhibition by shRNA repressed the cell proliferation, and the cell numbers in G2/M phase and cell apoptosis rate were increased in both SK-OV-3 and OVCAR-3 cells. It has been found that CDK1 was one of the hub genes in the pathogenesis of endometrial cancer. CDK1 inhibitor, RO3306, induced cell apoptosis and caused G2/M phase arrest of the cell cycle in endometrial cancer cells. Accordingly, in this example the bioinformatics analysis results revealed that the expression level of CDK1 in TP-472-treated uLMS cells was decreased. This suggests the possibility that CDK1 could serve as a therapeutic target for uLMS patients.

TOP2A is expressed predominantly in cycling cells and plays important roles in DNA replication, chromosome segregation, and transcription, while TOP2B participates mainly in transcription, and it is ubiquitously expressed in both cycling and postmitotic cells. If sister chromatids are not fully separated, cells will be arrested at the G2 phase. Accordingly, by blocking the TOP2A's function after chromosome condensation, cells arrested at metaphase, chromosomes failed to separate, and anaphase bridges formed, resulting in partial or complete chromosome gains or losses and polyploidy. Histone deacetylases (HDACs) modify nucleosomal histones. The results of the coimmunoprecipitation experiments of this example indicated that TOP2A and TOP2B are substrates for HDAC1 and HDAC2, Class I HDAC enzymes, and that complexes containing HDAC1 or HDAC2 can increase TOP2 activity. It has previously been shown that HDAC inhibitors induced apoptosis of uterine fibroid cells and cell cycle arrest. In this example, it was demonstrated that inhibition of BRD9 downregulated the expression of TOP2A and TOP2B; therefore, it is plausible that iBRD9 exerts its effect via HDACs. These results suggested that iBRD9 altered gene set comprises a distinct and functionally connected group of targets in uLMS phenotype. These hub genes have predictive value for the prognosis and progression of uLMS and may contribute to the understanding of basic and clinical research on uLMS.

Previously, it has been reported that crosstalk between different epigenetic mechanisms regulated gene expression. To determine the relation between BRD9 and other histone marks, the epigenome alterations associated with differentially expressed genes (DEGs) upon TP-472 treatment was analyzed. Notably, DEGs in response to TP-472 treatment were significantly associated with the enrichment of several histone marks, including H3K27me3, H3K4me1, H3K4me2, and H3K4me3. It was previously reported that BET BRDs play a role in the installing histone methylation. For instance, blocking readers of H3K27ac by BET inhibitor (JQ1) abolished H3K27ac-induced H3K4me3 installation and downstream gene activation. Although epigenetic changes correlating to the uLMS phenotypes have been reported in uLMS, the findings of this example, present evidence showing that non-BET BRDs may play an important role in crosstalk with histone marks, implicating non-BET BRDs in the complex oncogenic epigenome network contributing to the pathogenesis of malignant uLMS.

miRNAs are short (~22 nucleotides) non-coding RNAs that regulate post-transcriptional gene expression by influencing the translation or stability of target mRNAs. The interplay between miRNAs and epigenomic marks has been widely reported, including uLMS. In this example, it was demonstrated that miRNAs might play a role in regulating gene expression in uLMS cells in response to TP-472 treatment. Several miRNAs were identified that correlated with DEGs either up or downregulated by TP-472 treatment. These miRNAs have not been reported in the uLMS, broadening the knowledge that BRDs may alter the transcriptome via miRNA-mediated gene regulation. This example emphasizes that pharmacological inhibition of BRD9 suppressed the development of uLMS.

Figure 10:
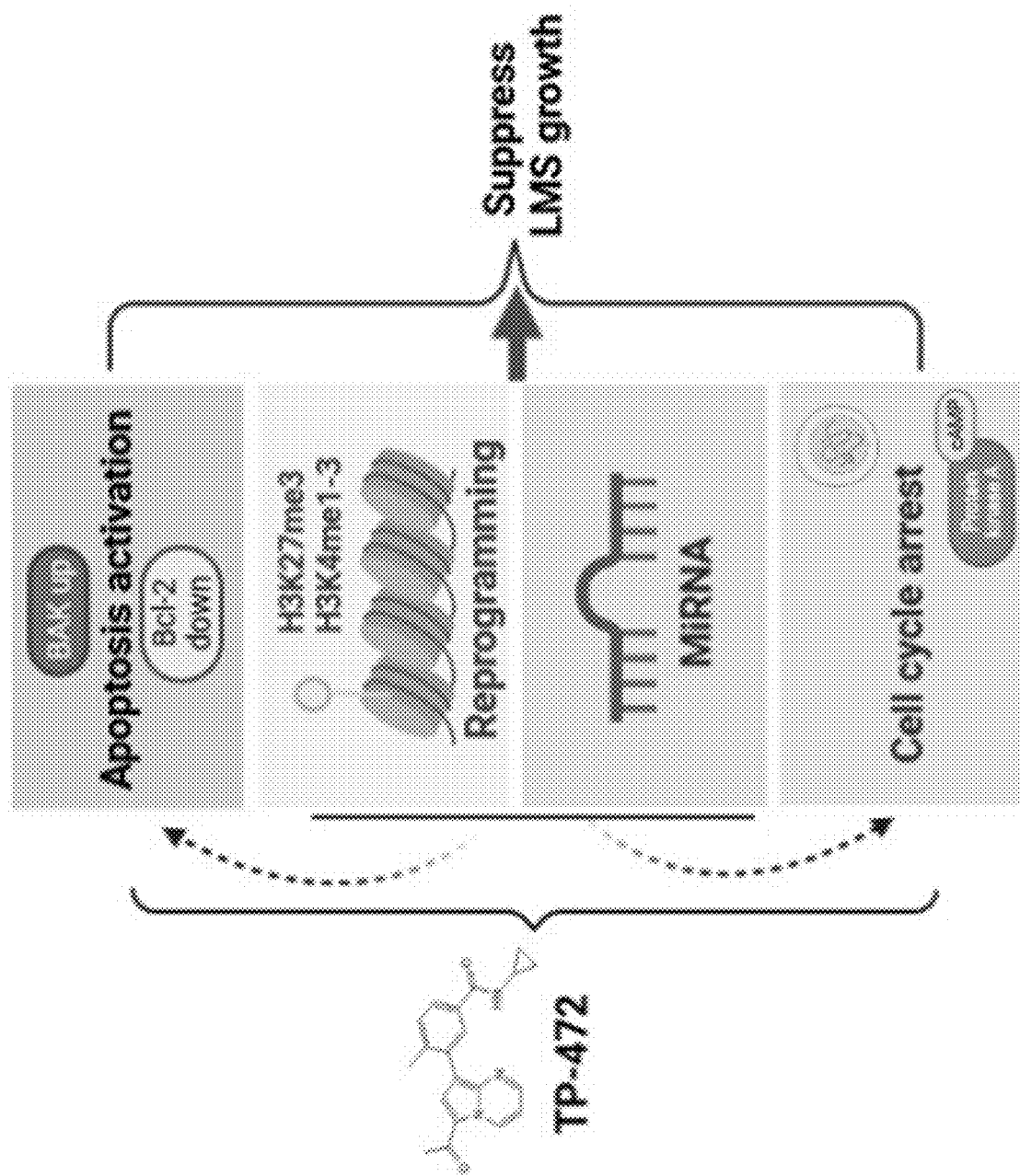
FIG. 10 is a model showing that TP-472 treatment activates apoptosis, induces cell cycle arrest, induces miRNA-mediated gene regulation, and reprograms pro-oncogenic epigenome in uLMS cells.

Without wishing to be bound by theory, a proposed mechanistic model for targeting non-BET BRDs in uLMS based on the findings herein follows: (1) BRD9 expression is abnormally unregulated in uLMS tissues and cells; (2) targeting BRD9 alters the uLMS phenotype with a decrease in cell proliferation and anti-apoptotic marker BCL-2; (3) TP-472 altered several important pathways and reprogrammed the oncogenic epigenome and miRNA network to suppress the uLMS phenotype (FIG. 10).

REFERENCES

1. D'Angelo E, Prat J. Uterine sarcomas: a review. Gynecologic oncology. 2010; 116(1):131-9.
2. Seagle B L, Sobecki-Rausch J, Strohl A E, Shilpi A, Grace A, Shahabi S. Prognosis and treatment of uterine leiomyosarcoma: A National Cancer Database study. Gynecologic oncology. 2017; 145(1):61-70.
3. Hensley M L, Blessing J A, Mannel R, Rose P G. Fixed-dose rate gemcitabine plus docetaxel as first-line therapy for metastatic uterine leiomyosarcoma: a Gynecologic Oncology Group phase II trial. Gynecologic oncology. 2008; 109(3):329-34.
4. Gadducci A, Landoni F, Sartori E, Zola P, Maggino T, Lissoni A, et al. Uterine leiomyosarcoma: analysis of treatment failures and survival. Gynecologic oncology. 1996; 62(1):25-32.
5. Garcia N, Ulin M, Ali M, Al-Hendy A, Carvalho K C, Yang Q. Evaluation of Hedgehog Pathway Inhibitors as a Therapeutic Option for Uterine Leiomyosarcoma Using the Xenograft Model. Reprod Sci. 2021.
6. Yang Q, Ciebiera M, Victoria Bariani M, Ali M, Elkafas H, Boyer T G, et al. Comprehensive Review of Uterine Fibroids: Developmental Origin, Pathogenesis, and Treatment. Endocr Rev. 2021.
7. Zuccala E. Epigenetics: Misdirecting methylation to drive oncogenesis. Nat Rev Cancer. 2016; 16(7):410.
8. Wong C C, Qian Y, Yu J. Interplay between epigenetics and metabolism in oncogenesis: mechanisms and therapeutic approaches. Oncogene. 2017; 36(24):3359-74.
9. Yang Q W, Liu S, Tian Y, Salwen H R, Chlenski A, Weinstein J, et al. Methylation-associated silencing of the thrombospondin-1 gene in human neuroblastoma. Cancer Res. 2003; 63(19):6299-310.
10. Yang Q, Zage P, Kagan D, Tian Y, Seshadri R, Salwen H R, et al. Association of epigenetic inactivation of RASSF1A with poor outcome in human neuroblastoma. Clin Cancer Res. 2004; 10(24):8493-500.
11. Yang Q, Tian Y, Ostler K R, Chlenski A, Guerrero U, Salwen H R, et al. Epigenetic alterations differ in phenotypically distinct human neuroblastoma cell lines. BMC Cancer. 2010; 10:286.
12. Jones P A. Epigenetics in carcinogenesis and cancer prevention. Ann N Y Acad Sci. 2003; 983:213-9.
13. Kanwal R, Gupta S. Epigenetics and cancer. J Appl Physiol (1985). 2010; 109(2):598-605.
14. Khare S, Verma M. Epigenetics of colon cancer. Methods Mol Biol. 2012; 863:177-85.
15. Kim W J, Kim Y J. Epigenetics of bladder cancer. Methods Mol Biol. 2012; 863:111-8.
16. Laird P W. Cancer epigenetics. Hum Mol Genet. 2005; 14 Spec No 1:R65-76.
17. Yang Q, Mas A, Diamond M P, Al-Hendy A. The Mechanism and Function of Epigenetics in Uterine Leiomyoma Development. Reprod Sci. 2016; 23(2):163-75.
18. Jain A K, Barton M C. Bromodomain Histone Readers and Cancer. J Mol Biol. 2017; 429(13):2003-10.
19. Fujisawa T, Filippakopoulos P. Functions of bromodomain-containing proteins and their roles in homeostasis and cancer. Nat Rev Mol Cell Biol. 2017; 18(4):246-62.
20. Crawford N P, Alsarraj J, Lukes L, Walker R C, Officewala J S, Yang H H, et al. Bromodomain 4 activation predicts breast cancer survival. Proc Natl Acad Sci USA. 2008; 105(17):6380-5.
21. Leal A S, Liu P, Krieger-Burke T, Ruggeri B, Liby K T. The Bromodomain Inhibitor, INCB057643, Targets Both Cancer Cells and the Tumor Microenvironment in Two Preclinical Models of Pancreatic Cancer. Cancers (Basel). 2020; 13(1).
22. Kregel S, Malik R, Asangani I A, Wilder-Romans K, Rajendiran T, Xiao L, et al. Functional and Mechanistic Interrogation of BET Bromodomain Degraders for the Treatment of Metastatic Castration-resistant Prostate Cancer. Clin Cancer Res. 2019; 25(13):4038-48.
23. Kato F, Fiorentino F P, Alibes A, Perucho M, Sanchez-Cespedes M, Kohno T, et al. MYCL is a target of a BET bromodomain inhibitor, JQ1, on growth suppression efficacy in small cell lung cancer cells. Oncotarget. 2016; 7(47):77378-88.
24. Faivre E J, McDaniel K F, Albert D H, Mantena S R, Plotnik J P, Wilcox D, et al. Selective inhibition of the BD2 bromodomain of BET proteins in prostate cancer. Nature. 2020; 578(7794):306-10.
25. Zhu X, Liao Y, Tang L. Targeting BRD9 for Cancer Treatment: A New Strategy. Onco Targets Ther. 2020; 13:13191-200.
26. Bell C M, Raffeiner P, Hart J R, Vogt P K. PIK3C A Cooperates with KRAS to Promote MYC Activity and Tumorigenesis via the Bromodomain Protein BRD9. Cancers (Basel). 2019; 11(11).
27. Huang H, Wang Y, Li Q, Fei X, Ma H, Hu R. miR-140-3p functions as a tumor suppressor in squamous cell lung cancer by regulating BRD9. Cancer Lett. 2019; 446:81-9.
28. Del Gaudio N, Di Costanzo A, Liu N Q, Conte L, Migliaccio A, Vermeulen M, et al. BRD9 binds cell type-specific chromatin regions regulating leukemic cell survival via STATS inhibition. Cell Death Dis. 2019; 10(5):338.
29. Care M A, Westhead D R, Tooze R M. Parsimonious Gene Correlation Network Analysis (PGCNA): a tool to define modular gene co-expression for refined molecular stratification in cancer. NPJ Syst Biol Appl. 2019; 5:13.

30. Jacomy M, Venturini T, Heymann S, Bastian M. ForceAtlas2, a continuous graph layout algorithm for handy network visualization designed for the Gephi software. PLoS One. 2014; 9(6):e98679.
31. Xie Z, Bailey A, Kuleshov M V, Clarke DJB, Evangelista J E, Jenkins S L, et al. Gene Set Knowledge Discovery with Enrichr. Curr Protoc. 2021; 1(3):e90.
32. Supek F, Bosnjak M, SkuncaN, Smuc T. REVIGO summarizes and visualizes long lists of gene ontology terms. PLoS One. 2011; 6(7):e21800.
33. Yang Q, Elam L, Laknaur A, Gavrilova-Jordan L, Lue J, Diamond M P, et al. Altered DNA repair genes in human uterine fibroids are epigenetically regulated via EZH2 histone methyltransferase. Fertility and Sterility. 2015; 104(3).
34. Mason L D, Chava S, Reddi K K, Gupta R. The BRD9/7 Inhibitor TP-472 Blocks Melanoma Tumor Growth by Suppressing ECM-Mediated Oncogenic Signaling and Inducing Apoptosis. Cancers (Basel). 2021; 13(21).
35. Nitulescu G M, Van De Venter M, Nitulescu G, Ungurianu A, Juzenas P, Peng Q, et al. The Akt pathway in oncology therapy and beyond (Review). Int J Oncol. 2018; 53(6):2319-31.
36. Costa RLB, Han H S, Gradishar W J. Targeting the PI3K/AKT/mTOR pathway in triple-negative breast cancer: a review. Breast Cancer Res Treat. 2018; 169(3):397-406.
37. Schrump D S, Hong J A, Nguyen D M. Utilization of chromatin remodeling agents for lung cancer therapy. Cancer J. 2007; 13(1):56-64.
38. Qi J. Bromodomain and extraterminal domain inhibitors (BETi) for cancer therapy: chemical modulation of chromatin structure. Cold Spring Harb Perspect Biol. 2014; 6(12):a018663.
39. Kaur J, Daoud A, Eblen S T. Targeting Chromatin Remodeling for Cancer Therapy. Curr Mol Pharmacol. 2019; 12(3):215-29.
40. Magnani L, Stoeck A, Zhang X, Lanczky A, Mirabella A C, Wang T L, et al. Genome-wide reprogramming of the chromatin landscape underlies endocrine therapy resistance in breast cancer. Proc Natl Acad Sci USA. 2013; 110(16):E1490-9.
41. Santillan D A, Theisler C M, Ryan A S, Popovic R, Stuart T, Zhou M M, et al. Bromodomain and histone acetyltransferase domain specificities control mixed lineage leukemia phenotype. Cancer Res. 2006; 66(20):10032-9.
42. Dawson M A, Prinjha R K, Dittmann A, Giotopoulos G, Bantscheff M, Chan W I, et al. Inhibition of BET recruitment to chromatin as an effective treatment for MLL-fusion leukaemia. Nature. 2011; 478(7370):529-33.
43. Lucas X, Gunther S. Targeting the BET family for the treatment of leukemia. Epigenomics. 2014; 6(2):153-5.
44. Belkina A C, Nikolajczyk B S, Denis G V. BET protein function is required for inflammation: Brd2 genetic disruption and BET inhibitor JQ1 impair mouse macrophage inflammatory responses. J Immunol. 2013; 190(7):3670-8.
45. Qiu H, Jackson A L, Kilgore J E, Zhong Y, Chan L L, Gehrig P A, et al. JQ1 suppresses tumor growth through downregulating LDHA in ovarian cancer. Oncotarget. 2015; 6(9):6915-30.
46. Richter GHS, Hensel T, Schmidt O, Saratov V, von Heyking K, Becker-Dettling F, et al. Combined Inhibition of Epigenetic Readers and Transcription Initiation Targets the EWS-ETS Transcriptional Program in Ewing Sarcoma. Cancers (Basel). 2020; 12(2).
47. Choi J, Manzano A, Dong W, Bellone S, Bonazzoli E, Zammataro L, et al. Integrated mutational landscape analysis of uterine leiomyosarcomas. Proc Natl Acad Sci USA. 2021; 118(15).
48. Park S G, Lee D, Seo H R, Lee S A, Kwon J. Cytotoxic activity of bromodomain inhibitor NVS-CECR2-1 on human cancer cells. Sci Rep. 2020; 10(1):16330.
49. Lu J, Qian C, Ji Y, Bao Q, Lu B. Gene Signature Associated With Bromodomain Genes Predicts the Prognosis of Kidney Renal Clear Cell Carcinoma. Front Genet. 2021; 12:643935.
50. Yamaguchi M, Kusunoki S, Hirayama T, Fujino K, Terao Y, Itakura A. Case of leiomyosarcoma arising from subserosal leiomyoma. J Obstet Gynaecol Res. 2019; 45(9): 1944-7.
51. Di Giorgio E, Dalla E, Franforte E, Paluvai H, Minisini M, Trevisanut M, et al. Different class IIa HDACs repressive complexes regulate specific epigenetic responses related to cell survival in leiomyosarcoma cells. Nucleic Acids Res. 2020; 48(2):646-64.
52. Moustakim M, Clark PGK, Hay D A, Dixon D J, Brennan P E. Chemical probes and inhibitors of bromodomains outside the BET family. Medchemcomm. 2016; 7(12):2246-64.
53. Dey P, Li J, Zhang J, Chaurasiya S, Strom A, Wang H, et al. Oncogenic KRAS-Driven Metabolic Reprogramming in Pancreatic Cancer Cells Utilizes Cytokines from the Tumor Microenvironment. Cancer Discov. 2020; 10(4):608-25.
54. Hann S R. Role of post-translational modifications in regulating c-Myc proteolysis, transcriptional activity and biological function. Semin Cancer Biol. 2006; 16(4):288-302.
55. Archer T C, Ehrenberger T, Mundt F, Gold M P, Krug K, Mah C K, et al. Proteomics, Post-translational Modifications, and Integrative Analyses Reveal Molecular Heterogeneity within Medulloblastoma Subgroups. Cancer Cell. 2018; 34(3):396-410 e8.
56. Tu W B, Helander S, Pilstal R, Hickman K A, Lourenco C, Jurisica I, et al. Myc and its interactors take shape. Biochim Biophys Acta. 2015; 1849(5):469-83.
57. Lourenco C, Resetca D, Redel C, Lin P, MacDonald A S, Ciaccio R, et al. MYC protein interactors in gene transcription and cancer. Nat Rev Cancer. 2021; 21(9): 579-91.
58. Gazon H, Barbeau B, Mesnard J M, Peloponese J M, Jr. Hijacking of the AP-1 Signaling Pathway during Development of ATL. Front Microbiol. 2017; 8:2686.
59. Langer S, Singer C F, Hudelist G, Dampier B, Kaserer K, Vinatzer U, et al. Jun and Fos family protein expression in human breast cancer: correlation of protein expression and clinicopathological parameters. Eur J Gynaecol Oncol. 2006; 27(4):345-52.
60. Chinenov Y, Kerppola T K. Close encounters of many kinds: Fos-Jun interactions that mediate transcription regulatory specificity. Oncogene. 2001; 20(19):2438-52.
61. Han Z, Boyle D L, Aupperle K R, Bennett B, Manning A M, Firestein G S. Jun N-terminal kinase in rheumatoid arthritis. J Pharmacol Exp Ther. 1999; 291(1):124-30.
62. Aicher W K, Dinkel A, Grimbacher B, Haas C, Seydlitz-Kurzbach E V, Peter H H, et al. Serum response elements activate and cAMP responsive elements inhibit expression of transcription factor Egr-1 in synovial fibroblasts of rheumatoid arthritis patients. Int Immunol. 1999; 11(1): 47-61.

63. Wang B, Guo H, Yu H, Chen Y, Xu H, Zhao G. The Role of the Transcription Factor EGR1 in Cancer. Front Oncol. 2021; 11:642547.
64. Zhang C, Chen L, Lou W, Su J, Huang J, Liu A, et al. Aberrant activation of m6A demethylase FTO renders HIF2alpha(low/-) clear cell renal cell carcinoma sensitive to BRD9 inhibitors. Sci Transl Med. 2021; 13(613): eabf6045.
65. Garcia N, Al-Hendy A, Baracat E C, Carvalho K C, Yang Q. Targeting Hedgehog Pathway and DNA Methyltransferases in Uterine Leiomyosarcoma Cells. Cells. 2020; 10(1).
66. Garcia N, Ulin M, Al-Hendy A, Yang Q. The Role of Hedgehog Pathway in Female Cancers. J Cancer Sci Clin Ther. 2020; 4(4):487-98.
67. Bulavin D V, Kovalsky O, Hollander M C, Fornace A J, Jr. Loss of oncogenic H-ras-induced cell cycle arrest and p38 mitogen-activated protein kinase activation by disruption of Gadd45a. Mol Cell Biol. 2003; 23(11):3859-71.
68. Bhargava S, Patil V, Shah R A, Somasundaram K. IGF2 mRNA binding protein 3 (IMP3) mediated regulation of transcriptome and translatome in glioma cells. Cancer Biol Ther. 2018; 19(1):42-52.
69. Zhang R, Shi H, Ren F, Zhang M, Ji P, Wang W, et al. The aberrant upstream pathway regulations of CDK1 protein were implicated in the proliferation and apoptosis of ovarian cancer cells. J Ovarian Res. 2017; 10(1):60.
70. Ying X, Che X, Wang J, Zou G, Yu Q, Zhang X. CDK1 serves as a novel therapeutic target for endometrioid endometrial cancer. J Cancer. 2021; 12(8):2206-15.
71. Gothe H J, Bouwman BAM, Gusmao E G, Piccinno R, Petrosino G, Sayols S, et al. Spatial Chromosome Folding and Active Transcription Drive DNA Fragility and Formation of Oncogenic MLL Translocations. Mol Cell. 2019; 75(2):267-83 e12.
72. Chen T, Sun Y, Ji P, Kopetz S, Zhang W. Topoisomerase IIalpha in chromosome instability and personalized cancer therapy. Oncogene. 2015; 34(31):4019-31.
73. Tsai S C, Valkov N, Yang W M, Gump J, Sullivan D, Seto E. Histone deacetylase interacts directly with DNA topoisomerase II. Nat Genet. 2000; 26(3):349-53.
74. Ali M, Shahin S M, Sabri N A, Al-Hendy A, Yang Q. Activation of beta-Catenin Signaling and its Crosstalk With Estrogen and Histone Deacetylases in Human Uterine Fibroids. J Clin Endocrinol Metab. 2020; 105(4).
75. Zhao W, Xu Y, Wang Y, Gao D, King J, Xu Y, et al. Investigating crosstalk between H3K27 acetylation and H3K4 trimethylation in CRISPR/dCas-based epigenome editing and gene activation. Sci Rep. 2021; 11(1):15912.
76. Hasan N M, Sharma A, Ruzgar N M, Deshpande H, Olino K, Khan S, et al. Epigenetic signatures differentiate uterine and soft tissue leiomyosarcoma. Oncotarget. 2021; 12(16):1566-79.
77. De Carvalho Fischer C, Hu Y, Morreale M, Lin W Y, Wali A, Thakar M, et al. Treatment with epigenetic agents profoundly inhibits tumor growth in leiomyosarcoma. Oncotarget. 2018; 9(27):19379-95.
78. Conconi D, Redaelli S, Lissoni A A, Cilibrasi C, Perego P, Gautiero E, et al. Genomic and Epigenomic Profile of Uterine Smooth Muscle Tumors of Uncertain Malignant Potential (STUMPs) Revealed Similarities and Differences with Leiomyomas and Leiomyosarcomas. Int J Mol Sci. 2021; 22(4).
79. de Almeida B C, Dos Anjos L G, Uno M, Cunha IWD, Soares F A, Baiocchi G, et al. Let-7 miRNA's Expression Profile and Its Potential Prognostic Role in Uterine Leiomyosarcoma. Cells. 2019; 8(11).
80. Gonzalez Dos Anjos L, de Almeida B C, Gomes de Almeida T, Mourao Lavorato Rocha A, De Nardo Maffazioli G, Soares F A, et al. Could miRNA Signatures be Useful for Predicting Uterine Sarcoma and Carcinosarcoma Prognosis and Treatment? Cancers (Basel). 2018; 10(9).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a uterine leiomyosarcoma in a female mammal, the method comprising administering to the female mammal an effective amount of an inhibitor of bromodomain-containing protein 9 (BRD9), wherein the inhibitor of BRD9 is TP-472, having a structure of

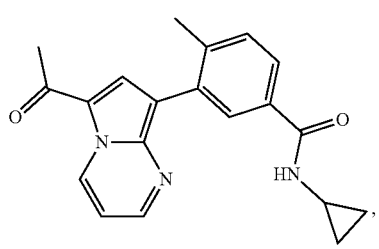 [SMILES: CC(=O)c1cc(-c2cc(C(=O)NC3CC3)ccc2C)c2ncccn12]

I-BRD9, having a structure of

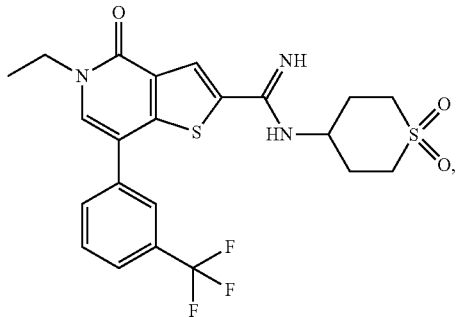 [SMILES: CCn1cc(-c2cccc(C(F)(F)F)c2)c2sc(C(=N)NC3CCS(=O)(=O)CC3)cc2c1=O]

LP99, having a structure of

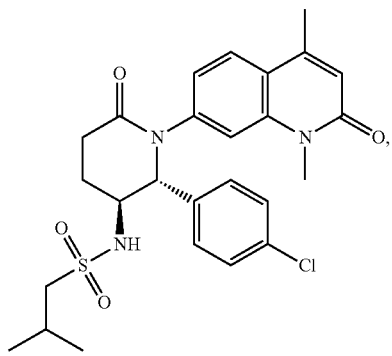 [SMILES: Cc1cc(=O)n(C)c2cc(N3C(=O)CC[C@H](NS(=O)(=O)CC(C)C)[C@H]3c3ccc(Cl)cc3)ccc12]

BI-9564, having a structure of

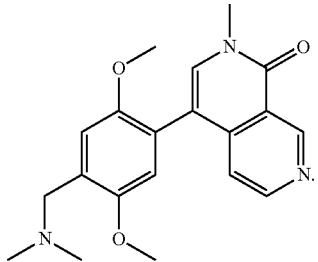 [SMILES: COc1cc(-c2cn(C)c(=O)c3cnccc23)c(OC)cc1CN(C)C]

BI-7273, having a structure of

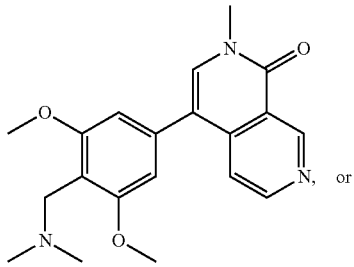 [SMILES: COc1cc(-c2cn(C)c(=O)c3cnccc23)cc(OC)c1CN(C)C]

or

VZ185, having a structure

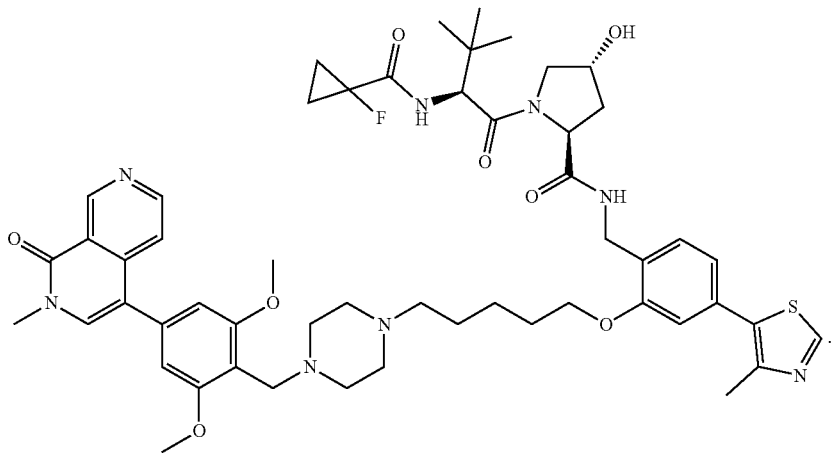 [SMILES: COc1cc(-c2cn(C)c(=O)c3cnccc23)cc(OC)c1CN1CCN(CCCCCOc2cc(-c3scnc3C)ccc2CNC(=O)[C@@H]2C[C@@H](O)CN2C(=O)[C@@H](NC(=O)C2(F)CC2)C(C)(C)C)CC1]

2. The method of claim 1, wherein the inhibitor of BRD9 is TP-472.

3. The method of claim 1, wherein the female mammal is a human.

4. The method of claim 2, wherein the female mammal is a human.

5. The method of claim 1, wherein the inhibitor of BRD9 is I-BRD9.

6. The method of claim 5, wherein the female mammal is a human.

7. The method of claim 1, wherein the inhibitor of BRD9 is LP99.

8. The method of claim 7, wherein the female mammal is a human.

9. The method of claim 1, wherein the inhibitor of BRD9 is BI-9564.

10. The method of claim 9, wherein the female mammal is a human.

11. The method of claim 1, wherein the inhibitor of BRD9 is BI-7273.

12. The method of claim 2, wherein the inhibitor of BRD9 is VZ185.

* * * * *